United States Patent
Yan et al.

(10) Patent No.: US 10,485,739 B2
(45) Date of Patent: *Nov. 26, 2019

(54) HIGH STRENGTH MICROCAPSULES

(71) Applicant: ENCAPSYS, LLC, Appleton, WI (US)

(72) Inventors: Nianxi Yan, Appleton, WI (US); Biao Duan, Appleton, WI (US); Linsheng Feng, Appleton, WI (US)

(73) Assignee: ENCAPSYS LLC, Appleton, WI (US)

( * ) Notice: Subject to any disclaimer, the term of this patent is extended or adjusted under 35 U.S.C. 154(b) by 177 days.

This patent is subject to a terminal disclaimer.

(21) Appl. No.: 14/884,671

(22) Filed: Oct. 15, 2015

(65) Prior Publication Data

US 2016/0106635 A1 Apr. 21, 2016

Related U.S. Application Data

(60) Provisional application No. 62/199,340, filed on Jul. 31, 2015, provisional application No. 62/117,604, filed on Feb. 18, 2015, provisional application No. 62/064,906, filed on Oct. 16, 2014.

(51) Int. Cl.
| | |
|---|---|
| *A61K 8/11* | (2006.01) |
| *A61K 9/50* | (2006.01) |
| *B01J 13/16* | (2006.01) |
| *A61L 15/46* | (2006.01) |
| *A61L 15/60* | (2006.01) |
| *A61Q 5/02* | (2006.01) |
| *A61Q 15/00* | (2006.01) |
| *A61Q 19/10* | (2006.01) |
| *C11B 9/00* | (2006.01) |
| *C11D 3/00* | (2006.01) |
| *C11D 3/50* | (2006.01) |
| *C11D 17/00* | (2006.01) |
| *C11D 17/06* | (2006.01) |
| *A61Q 19/00* | (2006.01) |
| *A61K 8/81* | (2006.01) |
| *C11D 11/00* | (2006.01) |

(52) U.S. Cl.
CPC .............. *A61K 8/11* (2013.01); *A61K 8/8129* (2013.01); *A61K 9/5026* (2013.01); *A61K 9/5089* (2013.01); *A61L 15/46* (2013.01); *A61L 15/60* (2013.01); *A61Q 5/02* (2013.01); *A61Q 15/00* (2013.01); *A61Q 19/00* (2013.01); *A61Q 19/10* (2013.01); *C11B 9/00* (2013.01); *C11D 3/001* (2013.01); *C11D 3/0015* (2013.01); *C11D 3/505* (2013.01); *C11D 11/0017* (2013.01); *C11D 11/0023* (2013.01); *C11D 17/0013* (2013.01); *C11D 17/0039* (2013.01); *C11D 17/06* (2013.01); *A61K 2800/10* (2013.01); *A61K 2800/412* (2013.01); *A61K 2800/56* (2013.01)

(58) Field of Classification Search
CPC .......... A61K 2800/10; A61K 2800/412; A61K 2800/56; A61K 8/11; A61K 9/5026; A61K 9/5089; A61L 15/46; A61L 15/60; A61Q 15/00; A61Q 19/00; A61Q 19/10; A61Q 5/02; C11B 9/00; C11D 11/0017; C11D 11/0023; C11D 17/0013; C11D 17/0039; C11D 17/06; C11D 3/001; C11D 3/0015; C11D 3/505
See application file for complete search history.

(56) References Cited

U.S. PATENT DOCUMENTS

| | | |
|---|---|---|
| 3,772,215 A | 11/1973 | Gould |
| 4,100,103 A | 7/1978 | Foris et al. |
| 4,396,670 A | 8/1983 | Sinclair |
| 4,406,816 A | 9/1983 | Sliwka |
| 4,552,811 A | 11/1985 | Brown et al. |
| 4,675,249 A | 6/1987 | Bowman |
| 4,753,968 A | 6/1988 | Shioi et al. |
| 4,760,108 A | 7/1988 | Asano et al. |
| 4,908,271 A | 3/1990 | Kasai et al. |
| 4,977,060 A | 12/1990 | Liang et al. |
| 5,061,410 A | 10/1991 | Sakamoto et al. |
| 5,071,706 A | 12/1991 | Soper |
| 5,110,883 A | 5/1992 | Gartner |
| 5,114,824 A | 5/1992 | Tan et al. |
| 5,292,835 A * | 3/1994 | Jahns ........................ B01J 13/18 428/402.2 |
| 5,456,852 A | 10/1995 | Isiguro |
| 5,596,051 A * | 1/1997 | Jahns ..................... A01N 25/28 428/402.2 |
| 5,990,202 A | 11/1999 | Nguyen et al. |
| 6,057,384 A | 5/2000 | Nguyen et al. |

(Continued)

FOREIGN PATENT DOCUMENTS

| | | |
|---|---|---|
| CA | 2714639 A1 | 8/2009 |
| CN | 102899168 B | 10/2013 |

(Continued)

OTHER PUBLICATIONS

Fogelson et al. Phys. Rev. E Stat. Nonlin. Soft. Matter. Phys. 2010; 81(5 Pt 1):051922. (Year: 2010).*

(Continued)

*Primary Examiner* — Robert A Wax
*Assistant Examiner* — Olga V. Tcherkasskaya
(74) *Attorney, Agent, or Firm* — IP&L Solutions; Edward K Welch, II

(57) ABSTRACT

High strength, high integrity microcapsules containing a hydrophobic core material wherein said microcapsule walls are formed of copolymers of select monomers through a multistep oil-in-water emulsification polymerization process.

42 Claims, 1 Drawing Sheet

(56) References Cited

U.S. PATENT DOCUMENTS

| | | | |
|---|---|---|---|
| 6,200,681 B1 | 3/2001 | Jahns et al. | |
| 6,261,483 B1 | 7/2001 | Frank et al. | |
| 6,544,926 B1 | 4/2003 | Bodmer et al. | |
| 6,716,526 B2 | 4/2004 | Weston et al. | |
| 6,869,923 B1 | 3/2005 | Cunningham et al. | |
| 7,550,200 B2 | 6/2009 | Hart et al. | |
| 7,736,695 B2 * | 6/2010 | Schwantes | B01J 13/16 427/213.3 |
| 7,803,422 B2 | 9/2010 | Schwantes et al. | |
| 7,932,191 B2 | 4/2011 | Dungworth et al. | |
| 7,938,897 B2 | 5/2011 | Hart et al. | |
| 7,947,370 B2 | 5/2011 | Jobmann et al. | |
| 8,067,089 B2 | 11/2011 | Schwantes | |
| 8,071,214 B2 | 12/2011 | Schwantes | |
| 8,455,098 B2 | 6/2013 | Schwantes et al. | |
| 8,551,935 B2 | 10/2013 | Smets et al. | |
| 8,715,544 B2 | 5/2014 | Schwantes | |
| 8,759,275 B2 | 6/2014 | Smets et al. | |
| 8,784,984 B2 | 7/2014 | Grey | |
| 8,796,381 B2 | 8/2014 | Schwantes et al. | |
| 9,714,396 B2 | 7/2017 | Feng et al. | |
| 9,714,397 B2 | 7/2017 | Feng et al. | |
| 9,993,401 B2 | 6/2018 | Barnett et al. | |
| 9,999,579 B2 | 6/2018 | Feng et al. | |
| 2003/0118822 A1 | 6/2003 | Jahns et al. | |
| 2004/0071746 A1 | 4/2004 | Popplewell et al. | |
| 2004/0265589 A1 | 12/2004 | Yamada et al. | |
| 2005/0003980 A1 | 1/2005 | Baker et al. | |
| 2006/0039934 A1 | 2/2006 | Ness et al. | |
| 2006/0102656 A1 | 5/2006 | Troost et al. | |
| 2006/0263518 A1 * | 11/2006 | Schwantes | B01J 13/16 427/213.3 |
| 2006/0276356 A1 | 12/2006 | Panandiker et al. | |
| 2006/0281834 A1 | 12/2006 | Lee et al. | |
| 2007/0138673 A1 | 6/2007 | Lee et al. | |
| 2007/0275866 A1 | 11/2007 | Dykstra | |
| 2008/0227888 A1 | 9/2008 | Jobmann et al. | |
| 2009/0274905 A1 | 11/2009 | Schwantes | |
| 2010/0286018 A1 | 11/2010 | Hentze et al. | |
| 2011/0169900 A1 | 7/2011 | Annable et al. | |
| 2011/0268778 A1 | 11/2011 | Dihora et al. | |
| 2011/0269657 A1 | 11/2011 | Dihora et al. | |
| 2011/0269658 A1 | 11/2011 | Dihora et al. | |
| 2011/0294715 A1 | 12/2011 | Smets et al. | |
| 2013/0137626 A1 | 5/2013 | Last | |
| 2013/0157863 A1 * | 6/2013 | Hahn | C08L 39/00 504/359 |
| 2013/0313734 A1 | 11/2013 | Yao et al. | |
| 2014/0037703 A1 | 2/2014 | Dihora et al. | |
| 2017/0165627 A1 | 6/2017 | Duan et al. | |
| 2017/0216161 A1 | 8/2017 | Yan et al. | |
| 2017/0281985 A1 | 10/2017 | Feng et al. | |
| 2017/0281986 A1 | 10/2017 | Feng et al. | |
| 2017/0283735 A1 | 10/2017 | Feng et al. | |
| 2017/0283736 A1 | 10/2017 | Feng et al. | |

FOREIGN PATENT DOCUMENTS

| | | |
|---|---|---|
| EP | 1719554 A2 | 11/2006 |
| EP | 2257440 B1 | 8/2015 |
| JP | 48-084086 | 11/1973 |
| JP | 2004113840 A | 4/2004 |
| JP | 2007-534855 A | 11/2007 |
| JP | 2013-525565 A | 6/2013 |
| JP | 2013-531694 A | 8/2013 |
| JP | 2013-538882 A | 10/2013 |
| JP | 2014-051670 A | 3/2014 |
| RU | 2095836 C1 | 10/1997 |
| RU | 2095836 C1 | 11/1997 |
| WO | 2009121831 A1 | 10/2009 |
| WO | 20100387071 A1 | 4/2010 |
| WO | 2012075293 A2 | 6/2012 |
| WO | 2015016367 A1 | 2/2015 |
| WO | 2015016368 A1 | 2/2015 |
| WO | 2015016369 A1 | 2/2015 |

OTHER PUBLICATIONS

International Search Report and Written Opinion for PCT/US2015/055905 (equiv. to claimed priority document U.S. Appl. No. 62/199,340).

* cited by examiner

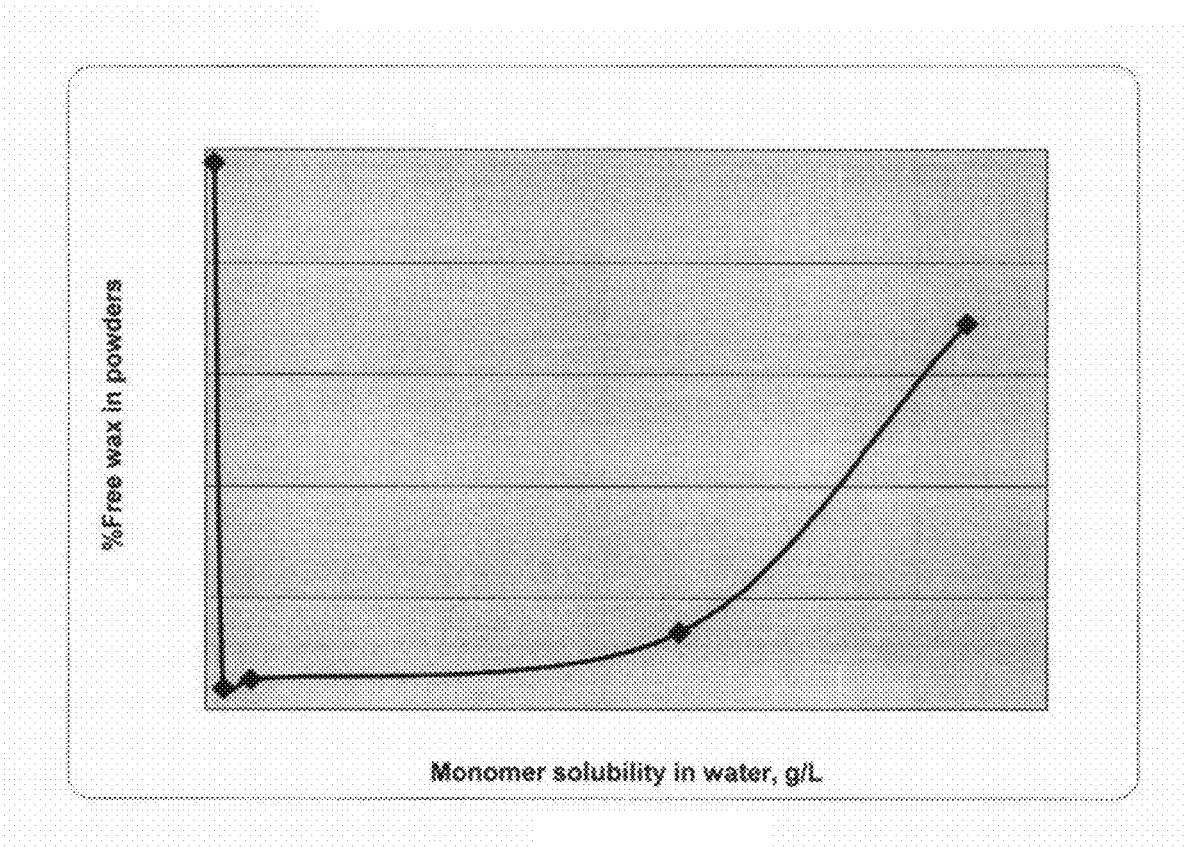

HIGH STRENGTH MICROCAPSULES

RELATED APPLICATIONS

The present application claims the benefit of prior filed U.S. Provisional Application No. 62/064,906 filed Oct. 16, 2014 entitled "Controlled Release Microcapsules"; U.S. Provisional Application No. 62/117,604 filed Feb. 18, 2015 entitled "Controlled Release Dual Walled Microcapsules"; and U.S. Provisional Application No. 62/199,340 filed Jul. 31, 2015 entitled "High Strength Microcapsules", the contents of all of which are hereby incorporated herein in their entirety by reference.

FIELD

The present disclosure relates to high strength microcapsules formed by an oil in water microencapsulation process employing an oil phase composition comprising a hydrophobic core material, especially a hydrophobic wax or a hydrophobic liquid, most especially a hydrophobic phase change material, and one or more ethylenically unsaturated monomers which are wholly or partially soluble or dispersible in the core material and an aqueous or water phase composition as the continuous phase comprising water and one or more ethylenically unsaturated monomers which are wholly or partially water soluble or water dispersible: the wall forming monomers of each of the oil phase composition and the water phase composition having certain hydrophilic/hydrophobic characteristics. Preferably the shell of the microcapsules is formed from a plurality of monomers, at least one of which is generally hydrophobic and is contained in the oil phase composition and at least one of which is moderately hydrophilic and is contained in the water phase composition. Most preferably the shell is formed, in whole or in part, from oligomers/prepolymers of the specified monomers of each phase composition.

The present disclosure also relates to a method of making high strength microcapsules from a plurality of ethylenically unsaturated monomers of certain hydrophilic/hydrophobic characteristics which method involves (i) the creation of an oil-in-water emulsion comprising a core phase composition comprising a core material and at least one hydrophobic monomer which is wholly or partially soluble or dispersible in the core material and an aqueous phase composition comprising water and at least one poor to moderately hydrophilic monomer which is wholly or partially water soluble or water dispersible and (ii) the formation of a shell wall through the polymerization of the monomers of each of the oil phase and the water phase at the interface of the oil phase and the water phase. Preferably, the disclosed method involves the use of at least two initiators, one in the oil phase and one in the water phase, each of which is activated at different temperatures and/or by different conditions and is capable of polymerizing the monomers of their respective phase. More preferably, the disclosed method involves the use of three or, most preferably, four initiators, at least two of which are activated by different temperatures/conditions and/or have different decomposition rates under the same activation conditions. Most preferably the method employs four initiators, preferably two in each phase, thereby enabling one to stage or sequence the shell formation whereby all or at least a portion of each of the wall forming monomers of each phase are oligomerized/prepolymerized prior to effecting actual polymerization and shell wall formation.

BACKGROUND

Microcapsules and microencapsulation technology are old and well known and their commercial applications varied. Microcapsules have played a significant role in various print technologies where a paper or other like substrate is coated with microcapsules containing ink or an ink-forming or inducing ingredient which microcapsules release the ingredient, generating an image, when fractured by pressure, as by a printing press or a stylus. Microcapsules have also played a significant role in various adhesive and sealant technologies including the encapsulation of solvents for solvent swellable/tackified preapplied adhesives whereby fracture of the microcapsules releases the solvent which softens or tackifies the adhesive to enable bonding and which re-hardened upon evaporation of the solvent. In other adhesive and sealant applications, the microcapsules contain one or more components of a curable or polymerizable adhesive or sealant composition which, upon release, leads to the cure or polymerization of the adhesive or sealant. In all of these early applications, functionality and efficacy, especially for long term storage and utility, is dependent upon the integrity of the microcapsule walls where the sought after integrity pertains to both strength, so as to avoid premature fracture, as well as impermeability, so as to prevent leakage and/or passage of the contents of the microcapsule through the microcapsule walls while also have easily attained break points to allow them to perform their function when intended by, e.g., simply screwing parts coated with coatings containing the microcapsules together.

Evolution of microencapsulation technology has led to many new commercial applications for encapsulated material, including applications that require microcapsules that fracture more readily, with less pressure, but not prematurely. Other applications require microcapsules that specifically allow for a controlled, slow release or permeation of the contents from within the microcapsules without the need to actually fracture the same. For example, perfume containing microcapsules are oftentimes applied to advertising inserts in magazines so that the reader can sample the smell of the perfume. Here strength is needed to avoid premature fracturing of the microcapsules due to the weight and handling of the magazine; yet, the microcapsules need ease of fracture so that the reader can simply scratch the treated area to release the contents of the microcapsule. At the same time, it is desirable to allow for some release of the contents, even without fracturing, to induce the reader to want to scratch the sample to get a more accurate sense of the smell.

Microcapsules are also finding increasing utility in laundering and fabric treatments: an application that requires both strength and defined release or break points. For example, a number of products exist wherein microcapsules of various ingredients, including perfumes, are applied to strips of a fabric material and added to the dryer wherein the tumbling action and/or heat of the dryer causes the microcapsules to fracture and/or become more permeable, releasing the ingredients which, in a volatilized state, permeate and deposit upon the contents of the dryer. This methodology applies that "fresh out of the dryer" smell, but is short lived as the perfume continues to volatilize from the treated fabric. Other products exist whereby microcapsules containing perfumes, odor controlling or masking materials, and other ingredients are applied directly or indirectly to the fabric, especially apparel, to provide a longer lived freshness to the same. Here, the integrity of the microcapsules is such that the microcapsules will not readily break during washing and handling, but will break during normal use and wearing of the garment which allows for the continued release of the contents of the microcapsules.

Despite the historical need for a break or fracturing of microcapsules, new potential applications are developing where capsule strength, specifically high strength, is becoming more and more critical. In these applications and intended applications, the microcapsules must be able to withstand conditions of high pressure, including pressures up to 100 psi, even 200 psi, or more as well as high temperatures, e.g., in excess of 150° C., even 200° C., without fracture and without an increase in the permeability of the shell wall, at least not until specific trigger events are attained which allow for such fracture or increased permeability. Still other applications require microcapsules that are not intended to break or release their contents at all. These demands are especially necessary for microcapsules containing phase change materials. For example, microcapsules containing phase change materials are being incorporated into fabrics so as to allow the fabric to draw heat away from the body. Most often these fabrics are incorporated into sporting garments and must withstand harsh wear due to physical exertion by the wearer, repeated washings with strong cleaning materials, etc., all without fracturing the microcapsules containing the phase change material. Other uses for microcapsules containing phase change materials include medical devices, construction materials, bedding, refrigerated transport, energy storage, cooling fluids, absorptive chillers such as for circuitry, solar devices, and applications where temperature moderation is desired. Where the microcapsule core is phase change material, uses can include such encapsulated materials in mattresses, pillows, bedding, textiles, sporting equipment, medical devices, building products, construction products. HVAC, renewable energy, clothing, athletic surfaces, electronics, automotive, aviation, shoes, beauty care, laundry, and solar energy.

Despite all the advances and improvements, there is still a need for improved specialty microcapsules that provide a suitable mix of containment or release/permeability characteristics and physical properties, especially high strength properties, for today's demanding applications. This is especially so in the area of perfumes and other odiferous ingredients, particularly in relation to fabric, textile and garment treatment, where controlled release and longevity as well as capsule strength and integrity are necessary.

Various methods and shell wall forming compositions have been proposed in the art in an effort to make microcapsules capable of withstanding certain harsher conditions, particularly higher temperatures. For instance, Sinclair (U.S. Pat. No. 4,396,670) encapsulated hydrophobic liquids using aminoplast resin capsules prepared from melamine formaldehyde pre-condensate; however, these become more permeable at elevated temperatures and may release formaldehyde. Jahns et. al. (U.S. Pat. No. 6,200,681) encapsulated latent heat storage materials in a shell formed by free radical polymerization of a monomer mixture comprising 30-100% of one or more $C_1$-$C_{24}$ alkyl esters of (meth)acrylic acid, 0-80% of a water insoluble or low solubility bi- or polyfunctional monomer and 0-40% of other monomers; however, the specific microcapsules described do not possess sufficient strength and will enable too much loss of core material at higher temperature. Weston et. al. (U.S. Pat. No. 6,716,526) prepare microcapsules having a shell comprising a copolymer formed from a monomer blend of 30-90% methacrylic acid, 10-70% of an alkyl ester of (meth)acrylic acid whose homopolymer has a Tg in excess of 60° C. and 0-40% other ethylenically unsaturated monomer. Although an improvement in that the permeability is improved even at high temperatures, these too lack the desired strength characteristics. Building on Weston et. al., Grey (U.S. Pat. No. 8,784,984) microencapsulates hydrophobic core materials in a polymer shell comprising the reaction product of a monomer mixture containing 1-95% of at least one hydrophobic mono-functional ethylenically unsaturated monomer, 5-99% of at least one polyfunctional ethylenically unsaturated monomer, and 0-60% of other mono-functional monomers wherein a hydrophobic polymer is incorporated into the monomer mixture prior to the polymerization thereof.

Despite the advances, the need still exists for improved microcapsules for hydrophobic materials and, perhaps more importantly, a more convenient and simpler method for their production. Most especially there is still a need for high integrity microcapsules that will withstand the forces and environments associated with their intended use, particularly in the encapsulation of phase change materials, without rupture or compromising the integrity of the microcapsule walls.

SUMMARY

According to the present disclosure, high strength microcapsules suitable for the encapsulation of hydrophobic core materials, especially phase change materials, are formed through an oil-in-water microencapsulation process in which the hydrophobic material is encapsulated in a polymer shell comprising the reaction product of one or more ethylenically unsaturated monomers which is wholly or partially soluble in the core material (the "core monomers"), and the reaction product of one or more ethylenically unsaturated monomers which is wholly or partially soluble in the aqueous or water continuous phase and has certain hydrophilic/hydrophobic characteristics (the "water phase monomers"): each of said reaction products also comprising a copolymer material derived from core monomers and water phase monomers and/or oligomers and/or prepolymers thereof, to the extent they are copolymerizable. Specifically, the core monomers are such that while wholly or partially soluble in the core material in their monomer state, as they oligomerize/prepolymerize they become less and less soluble in the core material, less lipophilic, to the extent they are lipophilic, and/or less hydrophobic whereby they begin to/tend to migrate within the oil phase composition to the interface between the oil phase and the water or continuous phase. The core monomers may be a single monomer or a mixture of monomers: though as a matter of convenience and cost, a single monomer is preferred. Additionally, the core monomers may be mono-, di- or polyfunctional monomers; though it is preferable that the core monomer is a difunctional monomer or comprises a predominant amount, i.e., 50 mole % or more, of a difunctional monomer. The water phase monomers, on the other hand, must include one or more monomers that manifest, at most, poor to moderate hydrophilic properties and/or whose oligomers/prepolymers manifest poor or limited solubility (particularly as compare to the monomer) in the water phase, whereby the oligomers/prepolymers of the water phase monomers are less hydrophilic and/or are less soluble in the water phase composition and, in a similar fashion to the prepolymers of the core monomers, begin to/tend to migrate within the water or continuous phase to the interface between the oil phase and the water or continuous phase. The water phase monomers generally comprise 1-100 wt %, preferably 30-100 wt %, of at least one ethylenically unsaturated monomer, most especially a difunctional monomer, manifesting poor to moderately hydrophilic properties; 0-99 wt %, preferably, 0-70 wt %, of at least one polyfunctional ethylenically unsaturated monomer, and 0-60 wt %, preferably 0-30 wt %, of other mono-functional monomers. Preferably the at least one water phase monomer manifesting poor to moderately hydrophilic properties is a difunctional monomer or comprises a predominant amount, i.e., 50 mole % or more, of a difunctional monomer.

According to the present disclosure there is also provided a method of making high strength microcapsules whose core material is a hydrophobic material, most preferably a hydrophobic phase change material, which method involves (i) preparing a oil phase composition comprising the hydrophobic core material and one or more ethylenically unsaturated monomers that are wholly or partially soluble in the core material, preferably one or more hydrophobic monomers, (ii) creating a dispersion of the oil phase composition in a water or water-based continuous phase composition comprising water and one or more ethylenically unsaturated monomers, all or a portion of which are poorly to moderately hydrophilic, and (iii) effecting the polymerization of the monomers of each phase, sequentially or concurrently or both, with or without first effecting an oligomerization/prepolymerization of one or both of the core phase monomers and the water phase monomers, and allowing the polymerization to continue until the microcapsules are formed. Preferably, the polymerization and, hence, formation of the capsule or shell wall occurs in a sequential manner with at least one of the core phase monomers and the water phase monomer, preferably both, undergoing a two-step polymerization whereby olgomerization/prepolymerization of some or all of the different core phase monomers and/or different water phase monomers and/or all or a portion of each of said core phase monomers and/or said water phase monomers is initiated and maintained for a period of time in their respective phases to form their respective oligomers/prepolymers after which full polymerization of the oligomers/prepolymers and any remaining monomer occurs at the interface of the oil and continuous phases during the wall forming stage of the process. Once a seed capsule is formed and the capsule wall continues to build, the capsule wall achieves a state where the oil phase and water phase are isolated from one another by the capsule wall. Thereafter, the oligomers/prepolymers and remaining monomers of each of the oil phase composition and the water phase composition continue to build upon the wall as it forms: the core phase monomers building on the inner surface of the shell and the water phase monomers building upon the outer surface of the shell. Though somewhat dependent upon the reaction conditions and selection of monomers and their relative reactivity, particularly under the conditions of free radical polymerization, it is believed that wall formation involves, at least to some extent, the copolymerization of the core monomers and/or their oligomers/prepolymers with the water phase monomers and/or their oligomers/prepolymers, particularly during the early stages of shell wall formation at which point the monomers/oligomers-prepolymers of each phase are readily accessible to one another at the oil phase/water phase interface.

Shell formation is achieved through the use of at least two initiators, at least one initiator in each of the core phase and the water phase. Preferably the process employs at least two initiators and a two-step polymerization process in at least one phase for effecting oligomerization/prepolymerization of at least a portion of the monomers of that phase before effecting full polymerization of the wall forming materials of both phases. Most preferably, the process employs four initiators, two in each phase, wherein the initiators in each phase are initiated or activated by different conditions and/or have a different rate of activation under the same conditions. In this way, the oligomers/prepolymer of each shell forming monomer composition may be generated in each phase and a period of time allowed to lapse before activation of the second initiator in each phase which then causes the full polymerization of the oligomers/prepolymers and any remaining monomer and rapid shell wall formation. It is also to be appreciated that the initiators in one phase may be initiated or activated by the same or similar conditions as the initiators in the other phase whereby oligomerization/prepolymerization and/or full polymerization in each phase is effected concurrently, or nearly so, by the same or similar conditions. While it is preferred that the second initiator in each phase be effected concurrently, the first initiator, that which effects oligomerization prepolymerization, may be effected by different conditions and/or the same conditions as the second initiator, preferably different conditions. Additionally, oligomerization/prepolymerization of the core monomer may be initiated prior to, concurrent with or subsequent to emulsification of the oil phase composition in the water phase composition. Similarly, oligomerization/-prepolymerization of the water phase monomer may occur prior to, concurrent with or subsequent to the emulsification of the oil phase composition in the continuous phase where the water phase composition or both the oil phase composition and the water phase composition comprise a first initiator and a second initiator.

DESCRIPTION OF THE FIGURES

FIG. 1 presents a plot of the correlation between the amount of free wax extractable from a given microcapsule and the water solubility of the water phase monomer(s) used in making that microcapsule from Example 2 herein.

DETAILED DESCRIPTION

For the purpose of this disclosure it is to be appreciated that all patents, patent publications and other publications mentioned herein are hereby incorporated herein in their entirety by reference. Additionally, for the purpose of this disclosure and the appended claims the term "core monomer" refers to that wall forming monomer or monomer mixture that is wholly or partially soluble or dispersible in the oil phase composition and is incorporated into the oil phase composition prior to the emulsification or dispersion thereof in the continuous or water phase. The term "water phase monomer" refers to that wall forming monomer or monomer mixture that is wholly or partially soluble or dispersible in the water phase composition and is contained in the water or continuous phase. The phrase "poor to moderately hydrophilic" means that the monomer or other referenced component, as allowed, is insufficiently hydrophilic such that it will not form a gel as it oligomerizes/prepolymerizes in the water phase and, preferably, is sufficiently hydrophobic, but not so hydrophobic, such that oligomers/prepolymers thereof will tend to migrate to the water/oil phase interface rather than form discrete particles or beads of the polymerized polymer in the water phase. Generally, a poor to moderately hydrophilic monomer is one that has a solubility of less than about 50 grams per liter (g/L), or even less than 30 g/L, or preferably from 0.01 g/L to about 50 g/L, or even from 0.01 g/L to 25 g/L, or even from 0.2 g/L to 30 g/L, or even from 0.05 to 25 g/L as measured in deionized water at 20° C. In following, it is to be understood that reference to a monomer, or another material, being soluble or disperable in a given material or composition means that the named monomer is wholly or partially soluble or dispersible therein on its own or such solubility or dispersability may be as a result of the addition of suitable emulsifies and/or solubilizers and/or as a result of elevating the temperature of the mixture and/or adjusting the pH to enhance solubility and/or dispersability. Further, as used herein and in the claims, the term "difunctional;" when used in relation to the requisite water phase monomers and core monomers refers to the presence of two ethylenically unsaturated polymerizable groups in the given monomer. Finally, as used in the specification and claims, the term "(meth)acrylate" refers to the acrylate as well as the methacrylate: when just the acrylate is intended to be exemplified, it will be so presented, e.g., isobornyl acrylate, and when just the methacrylate is intended to be exemplified, it will be so presented, e.g., isobornyl methacrylate. Hence, isobornyl (meth)acrylate refers to both isobornyl acrylate and isobornyl methacrylate. Similarly, a di(meth)acrylate may have two acrylate groups, two methacrylate groups or one acrylate group and one methacrylate group.

Although described below in greater specificity, the critical elements of the present teaching pertain to the selection of wall forming monomers and the sequencing and/or stepwise formation of the shell wall itself. Generally speaking, suitable poor to moderately hydrophilic water phase monomers are characterized as having one or more acrylate or methacrylate groups or other hydrophilic groups such as amino, urethane, alcohol and/or ether groups and a hydrophobic or non-hydrophilic hydrocarbon or hetero-hydrocarbon portion wherein the hydrocarbon portion is generally large enough such that, as the monomer polymerizes, the so formed oligomer/prepolymer becomes less soluble in the water phase and/or tends to manifest less hydrophilicity and/or tend to increase in hydrophobicity or lipophilicity than the monomer whereby their oligomers and prepolymers tend to migrate to the interface of the oil phase and the water phase, typically as a result of a lessening of attractiveness or increased repellency to the water phase and/or an increased attractiveness or drawing of the oligomer/prepolymer to the oil phase. The hydrocarbon or heterohydrocarbon portion of the water phase monomers may be a saturated or unsaturated hydrocarbon moiety such as an alkyl, alkenyl, alkylene or alkenylene group or a heteroalkyl, heteroalkenyl, heteroalkylene or heteroalkenylene group: hydrocarbon referring to moieties consisting essentially of carbon and hydrogen atoms and hetero referring to the presence of atoms other than, though in addition to, hydrogen and carbon (hetero atoms), most typically oxygen, nitrogen, sulfur and/or a halogen. Where such hetero atoms are present, they typically comprise less than 60 wt %, preferably, less than 40 wt %, more preferably less than 20 wt %, most preferably less than 10 wt % of the given hydrocarbon moiety of which they form a part and may be present in the main chain or as substituents thereto, e.g., an ether group or an hydroxy group, respectively. It is also to be appreciated that any of these hydrocarbon and/or heterohydrocarbon moieties may comprise or include cyclic structures and/or branched structures provided that the monomer manifest the requisite poor to moderately hydrophilic character as described herein, and provided that the resulting oligomer/prepolymer of the monomer is not insufficiently hydrophobic as described herein above. Preferred hydrocarbon and heterohydrocarbon portions of the monomer generally have from 1 to 8 carbon atoms and most preferably have from 1 to 3 carbon atoms, especially desired are those monomers having one or more methyl, ethyl, and propyl groups.

Preferably, the hydrophobic portion of the monomer can be a saturated hydrocarbon moiety such as;

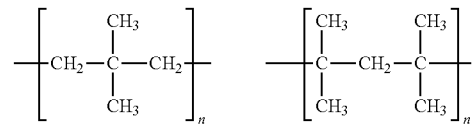

or even an unsaturated hydrocarbon moiety such as

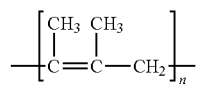

where n is an integer of 1 or greater, preferably 1 to 20. Of course the foregoing structures could also be modified with various hetero atoms, as will be appreciated by those skilled in the art. Furthermore, it is to be appreciated that combinations of the forgoing monomers, combinations of analogous heterohydrocarbon monomers as well as combinations of hydrocarbon and heterohydrocarbon monomers can also be advantageously used.

Suitable core monomers will comprise the same general make-up as the water phase monomers, indeed, there will be some (though certainly not all nor many) monomers that may be used in either phase; however, the core monomers are such that as they oligomerize and prepolymerize they become less soluble in the core material and/or they become less hydrophobic, more hydrophilic and/or less lipophilic or, in any event, their affinity for water increases and/or their affinity for the oil phase decreases, whereby they tend to migrate towards the interface of the oil phase composition and the water phase rather than form a gel or discrete particles of the polymerized monomer in the core phase composition. Thus, in considering the structures and limitations of the water phase monomers above, for purposes of identifying further suitable core monomers, the characteristics required of the core monomers may simply be substituted for the recitation of the characteristics of the water phase monomers in the foregoing discussion. Furthermore, while certain monomers may be used in either the water phase or the core phase, and while the same monomer may be present in both phases, it is especially preferred, if not critical, that where the same monomer is in both phases, at least one of the water phase and the core phase have a second monomer or a multi-step process is employed, i.e., oligomerization followed by polymerization. Most preferably, each of the water phase and the core phase has different monomers. However, if a common monomer is present in both phases, then, as noted above, at least one other monomer is present in at least one of the phases and, most preferably, the common monomer represents less than 50 mole % of the monomer of at least one of those phases.

According to a first embodiment of the present teaching there are provided high strength microcapsules having an encapsulated hydrophobic core material, especially a phase change material, which are formed through an oil-in-water microencapsulation process in which the hydrophobic core material is encapsulated in a polymer shell comprising the reaction product of one or more ethylenically unsaturated monomers which is wholly or partially soluble in the oil phase composition, and the reaction product of one or more ethylenically unsaturated monomers which is wholly or partially soluble in the water phase composition and has certain hydrophilic/hydrophobic characteristics, said reaction products also comprising copolymers of the core monomers and water phase monomers and/or their oligomers and/or prepolymers, to the extent said monomers, oligomers and/or prepolymers are copolymerizable. As noted hereinabove and below, the core monomers are such that while wholly or partially soluble in the oil phase composition in their monomer state, as they oligomerize/prepolymerize they become less and less soluble in the oil phase composition, less lipophilic (to the extent they are lipophilic), and/or less hydrophobic whereby they begin to/tend to migrate within the oil phase composition to the interface between the oil phase and the water or continuous phase. The water phase monomers, on the other hand, must include one or more monomers that manifest, at most, poor to moderate hydrophilic properties and/or whose oligomers/prepolymers manifest poor or limited solubility (particularly as compared to the monomer) in the water phase, whereby the oligomers/prepolymers of the water phase monomers are less hydrophilic and/or are less soluble in the water phase and, in a similar fashion to the prepolymers of the core monomers, begin to/tend to migrate within the water or continuous phase to the interface between the oil phase and the water or continuous phase.

Although copolymerization is contemplated, at least in certain embodiments, it is to be appreciated that selection of the core monomers and water phase monomers and/or a staggered polymerization or strict sequential polymerization of each may not allow for or prevent or mitigate copolymerization as between the monomers and/or oligomers/prepolymers of each phase. In the case where initiation of polymerization of the monomers and/or oligomers/prepolymers of one phase is staggered or delayed relative to initiation of polymerization of the monomers and/or oligomers/prepolymers of the other phase, but prior to the first material achieving isolation of the water phase from the core phase, and the monomers of each phase a not or not substantially copolymerizable and/or conditions do not favor copolymerization, the shell wall at the interface will generally comprise an interpenetrating network of the polymer of one phase with the polymer of the other phase. The degree or extent of the formation of an interpenetrating network and/or the thickness of the cross-sectional region of the shell wall comprising the interpenetrating network will depend, in part, upon the extent of the stagger or delay. Where the polymerization of the wall forming material of the second phase is shortly after initiation of polymerization of the wall forming material of the first phase, the degree of interpenetrating network is high and the region of interpenetration network is thick as compared to the same system where initiation of polymerization of the second wall forming material is considerably later. Furthermore, it is to be appreciated that the degree and extent of interpenetrating network formation will also depend, in part, upon the ability of the monomers to pass and/or protrude through the interface of the oil phase and water phase. In contrast where initiation of the second wall forming material is after formation of a seed capsule and/or following isolation of the two phases by the capsule wall arising from the first wall forming material the capsule wall will be more in the form of a two layered microcapsule wall or shell, the core monomer forming the inner layer of the shell and the water phase monomer forming the outer layer of the shell. In this instance, where monomers of each phase are copolymerizable with each other, the monomers/oligomers/prepolymers of the second wall forming material may copolymerize with functional groups of the first wall forming material on the surface of the shell wall available to the monomers/oligomers/prepolymers of the second wall forming. Otherwise, in these instances, the interface between the two shell layers will comprise polymer chains of the first wall forming material embedded in, with or without interpenetration, the initial polymer layer(s) of the second wall forming material as the latter polymerizes upon the shell of the first wall forming material. It is also contemplated that the shell may comprise, in whole or in part, discrete domains of one polymer in the other.

Most preferably, the core monomers and the water phase monomers and/or their respective oligomers/prepolymers will be capable of and undergo at least some degree of copolymerization. The extent of copolymerization and the resultant copolymers that are formed and become integrated into and/or form the shell wall will depend upon a number of factors including their relative reactivity, the amounts and relative amounts by which each is present in their respective phase and the extent to which they are present at the interface and/or are caused to migrate to the interface of the water and oil phase, the selection and activation of the initiators, the delay or stagger, if any, in initiation of the polymerization of the wall forming materials of the two phases, etc. Here, the mid-region of the microcapsule wall will comprise interwoven and/or an interpenetrating network of copolymer chains of the core and water phase monomers as well as polymer chains formed wholly of monomers of each phase. However, once the initial wall or shell is formed and the monomer of one phase is no longer accessible to the monomer of the other phase and/or cross-transfer of the monomer of one phase to the other is no longer possible, the respective build-up of the shell or microcapsule wall on the inside of the microcapsule is wholly due to and derived from the core phase monomer while that on the outside of the shell is wholly due to and derived from the water phase monomer. Hence, the chemical structure or make-up of the shell or microcapsule wall if one were to look at the cross-section of the same, will markedly vary from the inner surface to the exterior surface with the original interface point having the most diversity of monomer make-up and each surface having the least amount of diversity, if any, relative to the monomer make-up: the exterior surface being wholly or substantially so made up of water phase monomer and the interior surface being wholly or substantially made up of core phase monomer. In this regard, diversity refers to the amount of monomer from both phases, irrespective of the number of different monomers in each phase. Hence, the composition of the shell wall becomes more wholly made up of core phase monomer as one moves form the interface point to the inner core and more wholly made up on water phase monomer as one moves from the interface point to the outer shell surface. Of course, it is to be understood that the microcapsule or shell wall may also have embedded therein discrete domains of emulsifier and other aids used in making the microcapsules that become entrapped and, hence, embedded, in the polymer as it polymerizes.

The hydrophobic core of the microcapsules of the present teaching are derived from an oil phase composition comprising a hydrophobic core material, at least one core monomer and at least one initiator for initiating and/or effecting polymerization of the core monomer.

Hydrophobic Core Material

The hydrophobic core material may be any of a number of different materials depending upon the intended utility of the microcapsules. Typical core materials include UV absorbers. UV reflectors, pigments, dyes, colorants, scale inhibitors, corrosion inhibitors, antioxidants, pour point depressants, waxes, deposition inhibitors, dispersants, flame retardants, biocides, active dye tracer materials, odor control agents, natural oils, flavor and perfumes oils, crop protection agents, phase change materials and the like. Specific examples of suitable hydrophobic core materials include:

- aliphatic hydrocarbon compounds such as saturated or unsaturated $C_{10}$-$C_{40}$ hydrocarbons which are branched or preferably linear, e.g. n-tetradecane, n-pentadecane, n-hexadecane, n-heptadecane, n-octadecane, n-nonadecane, n-eicosane, n-heneicosane, n-docosane, n-tricosane, n-tetracosane, n-pentaco-sane, n-hexacosane, n-heptacosane, n-octacosane, and also cyclic hydrocarbons, e.g. cyclohexane, cyclooctane, cyclodecane;
- aromatic hydrocarbon compounds such as benzene, napthalene, biphenyl, o- or n-terphenyl, $C_1$-$C_4$ alkyl-substituted aromatic hydrocarbons such as dodecylbenzene, tetradecylbenzene, hexadecylbenzene, hexylnaphthalene or decylnaphthalene;
- saturated or unsaturated $C_6$-$C_{30}$ fatty acids such as lauric acid, stearic acid, oleic acid or behenic acid, preferably eutectic mixtures of decanoic acid with, for example, myristic, palmitic or lauric acid;
- fatty alcohols such as lauryl, stearyl, oleyl, myristyl, cetyl alcohol, mixtures such as coconut fatty alcohol and also oxo alcohols which are obtained by hydroformylation of alpha-olefins and further reactions;
- $C_6$-$C_{30}$ fatty amines such as decylamine, dodecylamine, tetradecylamine or hexadecylamine;
- esters such as $C_1$-$C_{10}$ alkyl esters of fatty acids, e.g. propyl palmitate, methyl stearate or methyl palmitate, and preferably their eutectic mixtures, or methyl cinnamate;
- natural and synthetic waxes such as montan waxes, montan ester waxes, carnauba wax, polyethylene wax, oxidized waxes, polyvinyl ether wax, ethylene-vinyl acetate wax or hard waxes obtained from the Fischer-Tropsch process;
- halogenated hydrocarbons such as chloroparaffins, bromooctadecane, bromopentadecane, bromononadecane, bromoeicosane, and bromodocosane.

Most especially the microcapsule according to the present teachings have a phase change material as the core material. Suitable phase change materials are typically known hydrocarbons that melt at a temperature of between −30° C. and 150° C. Generally the substance is a wax or an oil and preferably has a melting point at between 20° C. and 80° C., often around 40° C. Desirably the phase change substance may be a $C_8$-$C_{40}$ alkane or cycloalkane. Suitable phase change materials include all isomers of the alkanes or cycloalkanes. In addition it may also be desirably to use mixtures of these alkanes and/or cycloalkanes. The phase change material may be for instance any of the compounds selected from n-octadecane, n-tetradecane, n-pentadecane, n-heptadecane, n-octadecane, n-nonadecane, n-docosane, n-tricosane, n-pentacosane, n-hexacosane, cyclohexane, cyclooctane, cyclodecane and also isomers and/or mixtures thereof. Other phase change materials include aromatic hydrocarbons such as benzene, naphthalene, etc.; fatty acids such as lauric acid, stearic acid, etc.; alcohols such as lauryl alcohol, stearyl alcohol; and ester compounds such alkyl myristate, alkyl palmitate, alkyl stearate, etc., including, specifically, methyl stearate, methyl cinnamate, etc.

Another preferred core material consists essentially of a hydrophobic liquid, preferably an oil, or a hydrophobic wax which is a non-polymeric material, and most preferably a phase change material. Although the preferred hydrophobic oils and waxes are essentially non-polymeric, it is contemplated that these materials may contain smaller amounts, generally less than 10%, preferably less than 5% (e.g., 0.5 to 2%), by total weight of core of polymeric additives. Particularly desirable polymeric additives are those that modify the properties of the phase change material. For example, it is known that the temperature at which a phase change material melts on absorbing heat can be significantly different from the temperature at which it solidifies when losing heat. Alternatively, or in addition thereto, especially where the hydrophobic liquid or wax is a phase change material used for thermal storage, the core phase composition may further comprise select nucleating agents, which may also be a polymeric additive, that are found to prevent supercooling of hydrophobic liquids or waxes into which they are incorporated. Especially desirable polymeric additives and nucleating agents are those substances or compounds that will bring the melting and solidifying temperatures of the phase change material closer together. The use of such polymeric additives and/or nucleating agents is particularly desirable for encapsulated phase change materials to be used in various domestic applications or for garments.

Suitable nucleating agents are well known and include metal powders and claim powders. Especially preferred nucleating are those disclosed in Isiguro (U.S. Pat. No. 5,456,852) which is incorporated herein by reference. Generally speaking these nucleating agents have a melting point that is typically 20° C. to 110° C., preferably 30° C. to 100° C., higher than that of the phase change material into which it is incorporated. Suitable exemplary nucleating agents include aliphatic hydrocarbon compounds, aromatic compounds, esters (including fats and oils), fatty acids, alcohols and amides, including, specifically, but not limited thereto, cetyl alcohol, stearyl alcohol, eicosanol, myristic acid, palmitic acid, behenic acid, stearic acid amide, ethylenebisoleic acid amide, methylolbehenic acid amide and N-phenyl-N'-stearylurea, as well as combinations of two or more thereof. When the phase change compound is a nonpolar compound such as an aliphatic hydrocarbon or an aromatic hydrocarbon, preferable examples of the nucleating agent are fatty acids, alcohols and amides which have a higher polarity than does the nonpolar compound. Generally speaking the nucleating agent is used in an amount of from 0.5 to 40 weight %, preferably 1 to 35 weight %, relative to the amount or weight of the phase change material.

Alternatively, the phase change material may be a substance other than a hydrocarbon. For example, the phase change material could be an inorganic substance that absorbs and desorbs latent heat during a liquefying and solidifying phase transition and/or during dissolving/crystalization transition. Such inorganic compounds include for instance sodium sulphate decahydrate or calcium chloride hexahydrate as well as other inorganic compounds containing a large amount of water of crystallization, for example, sodium hydrogenphosphate dodecahydrate, sodium thiosulfate pentahydrate, and nickel nitrate hexahydrate. Thus the inorganic phase change material may be any inorganic substance that can absorb or desorb thermal energy during a transition at a particular temperature.

In following, the inorganic phase change material may be in the form of finely dispersed crystals which are dispersed throughout the core matrix which comprises a hydrophobic liquid or wax. In one form, the inorganic phase change material is dispersed throughout a solid hydrophobic substance such as a wax. In another form, crystals of the inorganic phase change material may be dispersed in a hydrophobic liquid or wax which remains substantially liquid, preferably a hydrocarbon liquid or wax. During a phase change these crystals become liquid droplets dispersed throughout the liquid. In order to prevent coalescence of these dispersed liquid droplets, it is advantageous to include a suitable surfactant, such as a water-in-oil emulsifier into the hydrophobic liquid. In yet another iteration of this embodiment where the core material comprises an inorganic phase change material dispersed throughout a matrix of a hydrophobic liquid or wax, the hydrophobic liquid or wax is itself a phase change material. In this preferred embodiment the hydrocarbon and inorganic materials may both absorb or desorb heat. Still, the hydrocarbon may not be a phase change material and may just serve as a carrier and/or process aid.

Although the discussion above with respect to the use of nucleating agents with phase change materials is presented with respect to certain hydrocarbon oils and waxes, it is to be appreciated that such nucleating agents, at the stated levels, are also suitably used with any phase change materials, including the aforementioned inorganic materials, to address supercooling and the like.

Core Monomer

The second component of the oil phase composition is the core monomer. As disclosed above, the core monomer comprises one or more ethylenically unsaturated monomers, preferably free-radically polymerizable ethylenically unsaturated monomers, that are wholly or partially soluble or dispersible in the oil phase composition, especially the core material, and whose oligomers/prepolymers become less soluble and/or less lipophilic and/or less hydrophobic (preferably more hydrophilic) as they oligomerize/prepolymerize whereby the oligomers and/or prepolymers tend to migrate through the oil phase composition to the interface of the oil phase composition and the water or continuous phase. Preferably, the core monomers are hydrophobic monomers, by which is meant a monomer with a water solubility of not more than about 25 g/L, preferably not more than 10 g/L, more preferably not more than 5 g/L as measured in deionized water at 20° C. In certain embodiments the hydrophobic monomers will have water solubility of no more than 1 g/L water, preferably not more than 0.1 g/L as measured in deionized water at 20° C.

The preferred core monomers are those difunctional monomers having the requisite characteristics defined above alone or in combination with other core monomers provided that at least 50 mole % of the core monomers are difunctional. Monomers which do not meet the requirements of the core monomers may also be present and may copolymerize with the requisite core monomer so long as the overall properties of the oligomers/prepolymers is retained. Generally speaking, such other monomers, if present, will be present at less than 50 mole %, preferably less than 25 mole % of the monomer in the core phase. Suitable difunctional core monomers include, but are not limited to, ethylene glycol di(meth)acrylate; 1,3-butylene glycol di(meth)acrylate; 1,4-butylene glycol di(meth)acrylate; propylene glycol di(meth)acrylate; divinyl; divinyl benzene; vinyl methacrylate; allyl (meth)acrylate; diallyl maleate; diallyl phthalate; diallyl fumarate; triallyl cyanurate; (meth)acryl polyesters of polyhydroxylated compounds; divinyl esters of polycarboxylic acids; diallyl esters of polycarboxylic acids; diallyl terephthalate; N,N'-methylene diacrylamide; hexamethylene bis maleimide; diallyl succinate; divinyl ether; the divinyl ethers of ethylene glycol or diethylene glycol; n-methytol acrylamide; n-isobutoxymethyl acrylamide; hexanediol diacrylate; neopentyl glycol diacrylate; divinyl benzene; triethylene glycol di(meth)acrylate; the butylene glycol di(meth)acrylates; tetraethylene glycol di(meth)acrylate; polyethylene glycol di(meth)acrylate; ethylene glycol di(meth)acrylate; diethylene glycol di(meth)acrylate; 1,6 hexanediol di(meth)acrylate; neopentyl glycol diacrylate; tripropylene glycol diacrylate; ethoxylated bisphenol A di(meth)acrylate; dipropylene glycol diacrylate; alkoxylated hexanediol diacrylate; alkoxylated cyclohexane dimethanol diacrylate; propoxylated neopentyl glycol diacrylate; allyl methacrylate; bis-phenol A di(meth)acrylate; and the like.

While the difunctional core monomers are preferred, mono- and poly-functional monomers are suitable as well, as well as combinations thereof and combinations of such monomers with difunctional monomers. Exemplary monofunctional monomers include, but are not limited to, vinyl 2-ethylhexanoate, vinyl laurate, vinyl stearate, vinyl alkyl or aryl ethers with ($C_9$-$C_{30}$) alkyl groups such as stearyl vinyl ether; ($C_6$-$C_{30}$) alkyl esters of (meth-)acrylic acid, such as hexyl (meth)acrylate, heptyl (meth)acrylate, octyl (meth)acrylate, isooctyl acrylate, isononyl acrylate, decyl (meth)acrylate, isodecyl (meth)acrylate, dodecyl (meth)acrylate, 2-ethythexyl (meth)acrylate, benzyl (meth)acrylate, lauryl (meth)acrylate, oleyl (meth)acrylate, palmityl (meth)acrylate, and stearyl (meth)acrylate; unsaturated vinyl esters of (meth)acrylic acid such as those derived from fatty acids and fatty alcohols; monomers derived from cholesterol; olefinic monomers such as 1-butene, 2-butene, 1-pentene, 1-hexene, 1-octene, isobutylene and isoprene; and the like. Exemplary polyfunctional monomers include, but are not limited to aliphatic or aromatic urethane acrylates, such as hexafunctional aromatic urethane (meth)acrylates; ethoxylated aliphatic difunctional urethane (meth)acrylates; aliphatic or aromatic urethane (meth)acrylates, such as tetra-functional aromatic (meth)acrylates; epoxy acrylates; epoxymethacrylates; glyceryl tri(meth)acrylate, trimethylolpropane tri(meth)acrylate; pentaerythritol tetra(meth)-acrytate; ethoxylated trimethylolpropane tri(meth)acrylate; propoxylated trimethylolpropane tri(meth)acrylate; propoxylated glyceryl tri(meth)acrylate; ditrimethylolpropane tetra(meth)acrylate; dipentaerythritol pentaacrylate; ethoxylated pentaerythritol tetraacrylate; and the like.

The amount of core monomer present in the oil phase composition may vary, but is generally within the range of from about 5-25 wt %, preferably from about 10-20 wt %, based on the total weight of the oil phase composition. Lower concentrations may be used but too low an amount of the core monomer results in a lessening in the physical properties attained. Higher amounts could also be used but are not needed and, in any event, the more wall material, the less the core material. Hence, it is desirable, as will be noted below, to optimize the amount of the core material while minimizing the amount of shell wall material.

Core Initiator

The last critical component of the oil phase composition is the one or more core initiators that are suitable for effecting oligomerization/prepolymerization and/or polymerization of the core monomer. Preferably, the core initiator comprises two free radical initiators each of which is initiated or activated by different conditions or, if by the same conditions, by different intensities of that condition. For example, if the core initiators are both activated by heat, then each will have a primary activation temperature that is different from the other, preferably, the activation temperatures will differ by at least 5° C., more preferably by at least 10° C., most preferably by at least 15° C. Here the concept of primary activation temperature or primary activation condition refers to that condition under which a given initiator achieves a 10 hour half-life. Selection of the initiator will depend upon the mode of activation and the monomer to be polymerized. In this regard, although it may be possible to use an actinic radiation activated initiator, at least in the oligomerization/prepolymerization stage, it is most desirable that the core initiator is a heat activated initiator. Similarly, the quantity of the activator to be incorporated into the oil phase composition will depend, in part, upon the amount of core monomer present and/or the decomposition rate at the anticipated reaction conditions. All of these factors are well known and generally set forth in the suppliers' guidelines and product specifications and, in any event can be determined by simple, direct experimentation.

Water/Continuous Phase

The second composition critical for the formation of the microcapsules of the present teaching is the water or aqueous phase composition which serves as the continuous phase of the reaction mix in which the microcapsules are formed and which contributes the second component of the shell wall to the microcapsules. The water or aqueous phase composition comprises water, a wall forming composition comprising one or more polymerizable ethylenically unsaturated monomers, preferably free radically polymerizable ethylenically unsaturated monomers, and at least one initiator, especially a free radical initiator, for the oligomerization/prepolymerization and/or polymerization of the ethylenically unsaturated monomer.

Water Phase Monomer

The key component of the water phase composition is the water phase monomer which comprises one or more polymerizable ethylenically unsaturated monomers, preferably free-radically polymerizable ethylenically unsaturated monomers, that manifest, at most, poor to moderate hydrophilic properties. The water phase monomer generally comprises 1-100 wt %, preferably 30-100 wt %, of at least one ethylenically unsaturated monomer manifesting poor to moderately hydrophilic properties; 0-99 wt %, preferably, 0-70 wt %, of at least one polyfunctional ethylenically unsaturated monomer, and 0-60 wt %, preferably 0-30 wt %, of other mono-functional monomers. Preferably the "at least one monomer manifesting poor to moderately hydrophilic properties" is a difunctional monomer or comprises a predominant amount, i.e., 50 mole % or more, of a difunctional monomer.

As noted above, where a second water phase composition is employed the second water phase composition preferably comprises one or more water soluble or dispersible (meth) acrylate monomers and/or oligomers/prepolymers; otherwise they will typically be in the single water phase composition. Those skilled in the art will readily recognize and appreciate that certain of the core monomers will have some water solubility or water dispersability, particularly in the presence of a suitable emulsifier and or solubilizer and/or at elevated temperature and/or adjusted pH, and may be used as or as a portion of the water phase monomer; however, it is preferred that the water phase monomer be different from the core phase monomer. Monomers that may be used as both a core monomer and a water phase monomer generally are amphiphilic, having constituents or groups that make them both hydrophilic and hydrophobic: the degree of hydrophilicity and/or hydrophobicity (or even lipophilicity) will be determinative of the extent of their use in one phase or the other.

The water phase monomers generally comprise 1-100 wt %, preferably 30-100 wt %, of at least one ethylenically unsaturated monomer manifesting poor to moderately hydrophilic properties; 0-99 wt %, preferably, 0-70 wt %, of at least one polyfunctional ethylenically unsaturated monomer, and 0-60 wt %, preferably 0-30 wt %, of other mono-functional monomers. Preferably the at least one monomer manifesting poor to moderately hydrophilic properties is a difunctional monomer or comprises a predominant amount, i.e., 50 mole % or more, of a difunctional monomer. As noted, other monomers may be present, particularly those that may copolymerize with the requisite water phase monomers, provided that if such other monomers do not themselves manifest or possess the requisite characteristics of the water phase monomers, then their selection and/or the amount of their presence is such that the oligomer/prepolymer arising from the oligomerization/prepolymerization retains the properties required of said oligomers/prepolymers, i.e., reduced solubility and/or hydrophilicity.

Exemplary ethylenically unsaturated monomer manifesting poor to moderately hydrophilic properties include, but are not limited to, amine modified polyether (meth)acrylate oligomers, hexafunctional aromatic urethane (meth)acrylate oligomers, hydroxyethyl (meth)acrylate, hydroxypropyl (meth)acrylate, methyl methacrylate, butanediol di(meth) acrylate, hexanediol di(meth)acrylate, ethoxylated bisphenol-A diacrylate, ethoxylated bisphenol-A dimethacrylate, isobornyl (meth)acrylate, pentaerythritol tri(meth)acrylate, pentaerythritol tetra(meth)acrylate, penta(meth)acrylate ester, diethylene glycol di(meth)acrylate, dipropylene glycol di(meth)acrylate, triethylene glycol di(meth)acrylate, tripropylene glycol di(meth)acrylate, neopentyl glycol di(meth) acrylate, trimethyltopropane tri(meth)acrytate, methoxy polyethylene glycol mono(meth)acrylate, ethoxylated trimethylolpropane tri(meth)acrylate, and ethoxylated pentaerythritol tetra(meth)acrylate, difunctional aliphatic epoxy (meth)acrylates, polyethylene glycol di(meth)acrylate, polypropylene glycol di(meth)acrylate, alkoxylated mono- or multi-functional (meth)acrylate ester, polyester (meth)acrylate oligomers, amine modified polyether (meth)acrylate oligomers and the like. Especially preferred water soluble or water dispersible (meth)acrylates are those having few hydrophilic groups, i.e., few amino, urethane, alcohol and/or ether groups.

Other monomers, e.g., mono-functional monomer and polyfunctional monomers that will co-polymerize with the aforementioned poor to moderately hydrophilic monomers are well known and widely used in free-radical encapsulation processes. Further exemplification is not deemed necessary.

The amount of water phase monomer employed in the water phase composition is dependent, at least in part, on the amount of core phase monomer present in the core phase composition. Generally speaking, the ratio by weight of the water phase monomer to the oil or core phase monomer is preferably in the range of from about 1:3 to about 1:50 or more, preferably from about 1:6 to 1:50. Generally, such weight ratios will relate to the presence of less than 20 wt %, preferably less than 10 wt % of the water phase monomer based on the water phase composition. Although no lower level is given, it is to be appreciated that sufficient monomer must be present to form a satisfactory wall and to enable a somewhat rapid cell wall formation. In this regard, if the concentration of the water phase monomer is too low, the encapsulation process is drawn out since it takes too long for sufficient monomer or oligomer/prepolymer to reach the interface of the oil phase composition and the water phase.

Hence it is likely that the concentration of the water phase monomer is at least 0.5 wt %, more likely at least 1% or more. Nevertheless, it is also to be noted that lower, though acceptable, concentrations of water phase monomer are desired as higher concentrations, especially those near or in excess of 20 wt %, tend to form gels or, at least, have a greater risk of forming a gel.

Another factor that is controlling the amount of water phase monomer incorporated in the water phase composition is the amount of core phase composition present in the emulsion and the desired thickness of the shell walls. In this regard, the weight ratio of oil phase composition to water phase monomer is from 50:50 to 98:2, respectively. An especially preferred microcapsule will have from 70 to 90% core and 30-10% shell, more preferably from 75 to 85% core, with an especially preferred microcapsule comprising about 82% core and about 18% shell.

Water Phase Initiator

The last critical component of the water phase composition is the one or more water phase initiators that are suitable for effecting oligomerization/prepolymerization and/or polymerization of the water phase monomer. Preferably, like the core initiator, the water phase initiator comprises two free radical initiators each of which is initiated or activated by different conditions or, if by the same conditions, by different intensities of that condition. Again, for example, if the core initiators are both activate by heat, then each will have a primary activation temperature that is different from the other, preferably, the activation temperatures will differ by at least 5° C., more preferably at least 10° C., most preferably by at least 15° C.; wherein the primary activation temperature or primary activation condition refers to that condition under which a given initiator achieves a 10 hour half-life. Selection of the water phase initiator will depend upon the mode of activation and the monomer to be polymerized. In this regard, while the water phase initiator may be actinic radiation, (e.g., UV light), activated, like the core initiators, the water phase initiators are preferably heat activated. Similarly, the quantity of the water phase activator to be incorporated into the water phase composition will depend, in part, upon the amount of water phase monomer present and/or the decomposition rate of the water phase activator under the given reaction conditions. All of these factors are well known and generally set forth in the suppliers' guidelines and product specifications and, in any event can be determined by simple, direct experimentation.

Generally, the water phase initiators are different from the core phase initiators since the later are not generally soluble in water and vice versa. Nonetheless, in selecting the initiators it is oftentimes desirable, though not necessary, that the initial initiator for each of the core monomer and the water phase monomer have the same or similar primary activation conditions. This is particularly so where four initiators are employed so that the oligomers/prepolymers of each monomer composition is formed at the same or generally the same point in the encapsulation process whereby both oligomers/prepolymers congregate at the interface of the oil phase composition and the water phase. Similarly, though not necessary, it is desirable that the second initiator contained in each phase has the same or similar primary activation conditions or are activated concurrently to optimize shell wall formation.

Processing Aids

Emulsifier

Optionally, though preferably, the water phase composition or, in the case of microcapsules prepared from two or more water phase compositions, one or both of said water phase compositions will contain an emulsifier to aid in the creation of the dispersion or emulsification of the oil phase composition in the continuous water phase. Similarly, where dual water phase wall forming materials are employed an emulsifier is employed to disperse the oil phase composition in that water phase. Less critical, but again, preferably, an emulsifier, preferably a non-ionic emulsifier, is added to one or both water phase compositions to aid in the dispersion and/or solubility of the poor to moderately hydrophilic water phase monomer in that water phase composition.

Emulsifiers of all types are suitable for use in the practice of the present process though it is to be appreciated, and those skilled in the art will readily recognize that different systems, e.g., different core monomer and/or core materials, will be better suited with one or more classes of emulsifiers than others. Specifically, while the present teachings are applicable to anionic, cationic, non-ionic and amphoteric emulsifiers generally, preferred emulsifiers are the cationic and non-ionic emulsifiers, particularly those having polyalkylether units, especially polyethylene oxide units, with degrees of polymerization of the alkylene ether unit of greater than about 6. Preferred emulsifiers are those which significantly reduce the interfacial tension between the continuous water phase and dispersed oil phase composition, and thereby reduce the tendency for droplet coalescence. In this regard, generally the emulsifiers for use in the first water phase for aiding in the oil in water emulsion or dispersion will have HLB values of from 11 to 17. While emulsifiers of the same HLB value may also be used in the second water phase, those emulsifiers that are used to enhance the solubility and/or dispersability of the water phase monomer in the second water phase will generally have HLB values of 16 to 20. Of course, emulsifiers/surfactants of lower and higher HLB values that achieve the same objective as noted are also included.

Exemplary emulsifiers include, but are not limited to polyvinyl alcohols, especially those that are partially hydrolyzed; cellulose derivatives such as ethyl hydroxyethyl cellulose, 2-hydroxyethyl cellulose, hydroxybutyl methylcellulose, hydroxypropyl methylcellulose, etc.; gums such as acacia gum and xantham gum; poly(meth)acrylic acids and derivatives; and poly(styrene-co-maleic acid) and derivatives and the like. Most preferably, the emulsifier/emulsion stabilizer is a polyvinyl alcohol, particularly a polyvinyl alcohol that has been derived from polyvinyl acetate, wherein between 85 and 95%, preferably 88 to 90% of the vinyl acetate groups have been hydrolyzed to vinyl alcohol units.

Additional exemplary anionic surfactants and classes of anionic surfactants suitable for use in the practice of the present invention include: sulfonates; sulfates; sulfosuccinates; sarcosinates; alcohol sulfates; alcohol ether sulfates; alkylaryl ether sulfates; alkylaryl sulfonates such as alkylbenzene sulfonates and alkylnaphthalene sulfonates and salts thereof; alkyl sulfonates; mono- or di-phosphate esters of polyalkoxylated alkyl alcohols or alkylphenols; mono- or di-sulfosuccinate esters of $C_{12}$ to $C_{15}$ alkanols or polyalkoxylated $C_{12}$ to $C_{15}$ alkanols; ether carboxylates, especially alcohol ether carboxylates; phenolic ether carboxylates; polybasic acid esters of ethoxylated polyoxyalkylene glycols consisting of oxybutylene or the residue of tetrahydrofuran; sutfoalkylamides and salts thereof such as N-methyl-N-oleoyltaurate Na salt; polyoxyalkylene alkylphenol carboxylates; polyoxyalkylene alcohol carboxylates; alkyl polyglycosidelalkenyl succinic anhydride condensation products; alkyl ester sulfates; naphthalene sulfonates; naphthalene formaldehyde condensates; alkyl sulfonamides;

sufonated aliphatic polyesters; sulfate esters of styrylphenyl alkoxylates; and sulfonate esters of styrylphenyl alkoxylates and their corresponding sodium, potassium, calcium, magnesium, zinc, ammonium, alkylammonium, diethanolammonium, or triethanolammonium salts; salts of ligninsulfonic acid such as the sodium, potassium, magnesium, calcium or ammonium salt; polyarylphenol polyalkoxyether sulfates and polyarylphenol polyalkoxyether phosphates; and sulfated alkyl phenol ethoxylates and phosphated alkyl phenol ethoxylates; sodium lauryl sulfate; sodium laureth sulfate; ammonium lauryl sulfate; ammonium laureth sulfate; sodium methyl cocoyl taurate; sodium lauroyl sarcosinate; sodium cocoyl sarcosinate; potassium coco hydrolyzed collagen; TEA (triethanolamine) lauryl sulfate; TEA (Triethanolamine) laureth sulfate; lauryl or cocoyl sarcosine; disodium oleamide sulfosuccinate; disodium laureth sulfosuccinate; disodium dioctyl sulfosuccinate; N-methyl-N-oleoyltaurate Na salt; tristyrylphenol sulphate; ethoxylated lignin sulfonate; ethoxylated nonylphenol phosphate ester calcium alkylbenzene sulfonate; ethoxylated tridecyl-alcohol phosphate ester, dialkyl sulfosuccinates; perfluoro ($C_6$-$C_{18}$)alkyl phosphonic acids; perfluoro($C_6$-$C_{18}$)alkylphosphinic acids; perfluoro($C_3$-$C_{20}$)alkyl esters of carboxylic acids; alkenyl succinic acid diglucamides; alkenyl succinic acid alkoxylates; sodium dialkyl sulfosuccinates; and alkenyl succinic acid alkylpolyglykosides. Further exemplification of suitable anionic emulsifiers include, but are not limited to, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesuifonate, sodium dialkylsulfosuccinates, dioctyl sulfosuccinate, sodium dilaurylsulfosuccinate, poly(styrene sulfonate) sodium salt, alkylene-maleic anhydride copolymers such as isobutylene-maleic anhydride copolymer, or ethylene maleic anhydride copolymer gum arabic, sodium alginate, carboxymethylcellulose, cellulose sulfate and pectin, poly(styrene sulfonate), pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; maleic anhydride copolymers (including hydrolyzates thereof), polyacrylic acid, polymethacrylic acid, acrylic acid alkyl acrylate copolymers such as acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

Exemplary amphoteric and cationic emulsifiers include alkylpolyglycosides; betaines; sulfobetaines; glycinates; alkanol amides of $C_8$ to $C_{18}$ fatty acids and $C_8$ to $C_{18}$ fatty amine polyalkoxylates; $C_1$ to $C_{18}$ alkyldimethylbenzylammonium chlorides; coconut alkyldimethylaminoacetic acids: phosphate esters of $C_8$ to $C_{18}$ fatty amine polyalkoxylates; alkylpolyglycosides (APG) obtainable from an acid-catalyzed Fischer reaction of starch or glucose syrups with fatty alcohols, in particular $C_8$ to $C_{18}$ alcohols, especially the $C_8$ to $C_{10}$ and $C_{12}$ to $C_{14}$ alkylpolyglycosides having a degree of polymerization of 1.3 to 1.6, in particular 1.4 or 1.5. Additional cationic emulsifiers include quaternary ammonium compounds with a long-chain aliphatic radical, e.g. distearyldiammonium chloride, and fatty amines. Among the cationic emulsifiers which may be mentioned are alkyldimethylbenzylammonium halides, alkyldimethylethyl ammonium halides, etc. specific cationic emulsifiers include palmitamidopropyl trimonium chloride, distearyl dimonium chloride, cetyltrimethylammonium chloride, and polyethyleneimine. Additional amphoteric emulsifiers include alkylaminoalkane carboxylic acids betaines, sulphobetaines, imidazoline derivatives, lauroamphoglycinate, sodium cocoaminopropionate, and the zwitterionic emulsifier cocoamidopropyl betaine.

Suitable non-ionic emulsifiers are characterized as having at least one non-ionic hydrophilic functional group. Preferred non-ionic hydrophilic functional groups are alcohols and amides and combinations thereof. Examples of non-ionic emulsifiers include: mono and diglycerides; polyarylphenol polyethoxy ethers; polyalkylphenol polyethoxy ethers; polyglycol ether derivatives of saturated fatty acids; polyglycol ether derivatives of unsaturated fatty acids; polyglycol ether derivatives of aliphatic alcohols; polyglycol ether derivatives of cycloaliphatic alcohols; fatty acid esters of polyoxyethylene sorbitan; alkoxylated vegetable oils; alkoxylated acetylenic diols; polyalkoxylated alkylphenols; fatty acid alkoxylates; sorbitan alkoxylates; sorbitol esters; $C_8$ to $C_{22}$ alkyl or alkenyl polyglycosides; polyalkoxy styrylaryl ethers; amine oxides especially alkylamine oxides; block copolymer ethers; polyalkoxylated fatty glyceride; polyalkylene glycol ethers; linear aliphatic or aromatic polyesters; organo silicones; polyaryl phenols; sorbitol ester alkoxylates; and mono- and diesters of ethylene glycol and mixtures thereof; ethoxylated tristyrylphenol; ethoxylated fatty alcohol; ethoxylated lauryl alcohol; ethoxylated castor oil; and ethoxylated nonylphenol; alkoxylated alcohols, amines or acids; amides of fatty acids such as stearamide, lauramide diethanolamide, and lauramide monoethanolamide; long chain fatty alcohols such as cetyl alcohol and stearyl alcohol; glycerol esters such as glyceryl laurate; polyoxyalkylene glycols and alkyl and aryl ethers of polyoxyalkylene glycols such as polyoxyethylene glycol nonylphenyl ether and polypropylene glycol stearyl ether. Polyethylene glycol oligomers and alkyl or aryl ethers or esters of oligomeric polyethylene glycol are preferred. Also preferred as non-ionic emulsifiers are polyvinyl alcohol, polyvinyl acetate, copolymers of polyvinyl alcohol and polyvinylacetate, carboxylated or partially hydrolyzed polyvinyl alcohol, methyl cellulose, various latex materials, stearates, lecithins, and various surfactants. It is known that polyvinyl alcohol is typically prepared by the partial or complete hydrolysis of polyvinyl acetate. Accordingly, by reference to polyvinyl alcohol we intend to include both completely and partially hydrolyzed polyvinyl acetate. With respect to the latter, it is preferred that the polyvinyl acetate be at least 50 mole % hydrolyzed, more preferably, at least 75 mole % hydrolyzed.

Where the emulsifier is a polymeric emulsifier, especially one having or derived from an acrylic ester, e.g., a polyacrylate, the molecular weight is generally at least 10,000, preferably at least 20,000, most preferably 30,000 or more. Additionally, the amount of emulsifier is typically from about 0.1 to about 40% by weight, more preferably from about 0.2 to about 15 percent, most preferably from about 0.5 to about 10 percent by weight based on the total weight of the formulation. It is to be appreciated that certain acrylic polymers and copolymers may perform both as an emulsifier as well as a polymerizable and/or non-polymerizable component in forming the microcapsule wall. With respect to the latter, the polymeric emulsifier, particularly those in the nature of higher molecular weight polymers, are trapped and/or incorporated into the polymer wall as it is formed. This is especially likely where the nature of the water phase changes and the solubilized polymer comes out of solution.

Other stabilizing substances that may be used, alone or in combination with the aforementioned materials, include ionic monomers. Typical cationic monomers include dialkyl amino alkyl acrylate or methacrylate including quaternary ammonium or acid addition salts and dialkyl amino alkyl acrylamide or methacrylamide including quaternary ammonium or acid addition salts. Typical anionic monomers include ethylenically unsaturated carboxylic or sulphonic monomers such as acrylic acid, methacrylic acid, itaconic acid, allyl sulphonic acid, vinyl sulphonic acid especially alkali metal or ammonium salts. Particularly preferred anionic monomers are ethylenically unsaturated sulphonic acids and salts thereof, especially 2-acrylamido-2-methyl propane sulphonic acid, and salts thereof.

The water phase compositions and the core phase compositions may further contain other ingredients conventional in the art including, e.g., chain transfer agents and/or agents which help control the molecular weight/degree of polymerization of the wall forming monomer, thereby aiding in the movement of the oligomer/prepolymer through the respective oil phase and water phase compositions. In this regard, optionally, though preferably, the water phase, particularly the second water phase composition, further includes at least one chain transfer agent and/or agent which aids in movement of the oligomer/prepolymer. Suitable chain transfer agents include, but are not limited to, lower alkyl alcohols having from 1 to 5 carbon atoms, mercaptoethanol, mercaptopropanol, thioglycolic acid, isooctylmercaptoproprionate, tert-nonylmercaptan, pentaerythritol tetrakis(3-mercaptoproprionate), dodecylmercaptan, formic acid, halogenated hydrocarbons, such as bromoethane, bromotrichloromethane, or carbon tetrachloride, and the sulfate, bisulfate, hydrosulfate, phosphate, monohydrogen phosphate, dihydrogen phosphate, toluene sulfonate, and benzoate salts of sodium and potassium, especially sodium hypophosphite and sodium bisulfate. If present, the chain transfer agents are preferably used in amounts ranging from 0.01 to 5%, preferably from 0.5 to 3%, by weight with respect to the monomers and/or oligomers employed.

The microcapsules according to the present teaching are made in a multi-step process as described below. For convenience, the process is presented in the preferred mode which involves two water phase components and a single core phase composition. Nonetheless, those skilled in the art will readily appreciate that the water phase composition may be prepared as a single composition to which the core phase composition is added or a three or more component composition where various ingredients are preferably isolated from one another until desired so as to avoid undue or undesired activation of the water phase activators and/or oligomerization/prepolymerization/polymerization of the water phase monomers.

In a first step a first water phase composition (WP1) comprising water and, preferably, an emulsifier and/or surfactant, is prepared by combining the two ingredients in a reaction vessel. Emulsifiers and/or stabilizers are desired in that they aid in the emulsification of the core phase composition as well as in stabilizing the same so as to avoid coalescence of the droplets. The volume of the first water phase component (WP1) is such as to simplify the formation of the emulsion of the core phase composition. If too little WP1 is employed, then it is difficult to attain a stable emulsion of the desired droplet size of the core phase composition as the droplets will tend to coalesce. On the other hand, if too much WP1 is used or if a single water phase composition were used, then again it is difficult to form the desired droplet size as one is having to needlessly emulsify in a much larger volume. In this regard, it maybe difficult, if not impossible, to generate sufficient shear in the mixture to produce droplets of the desired size.

Additionally, the second water phase composition (WP2) is prepared comprising water, the water phase monomer, and the water phase initiator(s). Again, though not required, it is desirable to include an emulsifier and/or surfactant in WP2. Here it is preferred to first incorporate the water phase monomer into a solution of the water and the emulsifier/surfactant, if present. It is also desirable to elevate the temperature to aid in the solubilization and/or dispersion of the monomer in the water phase. Thereafter, the water phase initiator is added to the mixture; however, if the temperature of the mixture had been elevated to aid in getting the water phase monomer into solution/suspension, then the mixture should be cooled or allowed to cool to a temperature that is safely below the lowest activation temperature of the one or more water phase initiators.

As noted previously, either of the WP1 or WP2 or both may contain other ingredients of the water phase composition; however, if there is any concern that these other ingredients will adversely affect the water phase monomer or another component of WP1 or adversely affect the water phase initiator, e.g., cause premature activation, or other ingredients in WP2, then those ingredients will be incorporated into the other water phase component or in yet a third water phase component (WP3). Generally, it is not necessary to employ a WP3; though it is mentioned as a possibility if needed.

The oil phase composition is formed by combining the core phase monomer and the core material. Most preferably this is conducted under moderate increased temperature so as to facilitate the solubilization or suspension of the monomer and other ingredients that may be present, including nucleating agents, in the core material: this is particularly so if the core material is a solid or wax or a high viscosity material. One may also add other ingredients such as surfactants and the like to aid in the solubilization/suspension of the core phase monomer in the core material. Once a stable solution or suspension of the core monomer in the core material is prepared, the core phase initiator is then added to the combination and the composition mixed to ensure good dispersion of the core phase initiator. Once again, if the temperature of the mixture had been elevated to aid in getting the core phase monomer into solution/suspension, then the mixture should be cooled or allowed to cool to a temperature that is safely below the lowest key activation temperature of the one or more core phase initiators. It is to be appreciated that certain initiators may have more of a bell curve type initiation response and, in those instances, it may not be possible or necessary to decrease the temperature below the lower end of that bell curve; rather, it is to be understood that a low level of activation and, hence, oligomerization/-prepolymerization of the core monomer in the oil phase composition is possible and allowable prior to emulsification without adversely affecting performance of the microcapsules of the present teaching. Indeed, it may be desirable to wholly or at least partially oligomerize/prepolymerize the core monomer before the emulsification step. Here, the conditions for effecting the initiator for said oligomerization/prepolymerization are preferably removed or reversed prior to emulsification to prevent a premature activation of the monomer in water phase. For example, if the temperature of the oil phase composition is elevated to initiate oligomerization/prepolymerization, it is best to cool the resultant oil phase composition before adding it to the water phase composition.

Once a stable oil phase composition is attained, it is added to and mixed with the WP1 composition in the reactor vessel. The mixture is milled until the desired droplet size of oil phase composition is attained. Thereafter the second water phase composition (WP2) is added to the reactor. The mixture is then mixed and the temperature raised to the primary activation temperature of the first water phase and core phase initiators. In this regard, it is desirable to select first initiators whose primary activation temperature is the same or fairly close to one another, generally within 5° C. of each other, more preferably within 2° C. of each other. On the other hand, it is to be appreciated that the activation temperatures of the two first initiators may be more widely separated and that difference may be advantageously exploited when, due to selection of monomers and/or core material, it is desirable to initiate oligomerization or prepolymerization of one of the water phase monomer or core phase monomer before the other. For instance, if the viscosity of the oil phase composition is such that migration of the oligomer/prepolymer of the core phase monomer is slow, one may wish to initiate oligomerization/prepolymerization of the core phase monomer prior to initiation oligomerization/prepolymerization of the water phase monomer. Conversely, if the droplets of core material are very small and the volume of the water phase high with a relatively low concentration of water phase monomer, it may be desirable to initiate oligomerization/prepolymerization of the water phase monomer prior to initiating oligomerization/prepolymerization of the core phase monomer. Not wishing to be bound by theory, the objective here is to ensure adequate levels of oligomer/prepolymer of both the core phase monomer and the water phase monomer at the interface of the oil phase composition and the water phase composition prior to initiating full polymerization and/or wall formation, or at least substantial wall formation.

Regardless, once oligomerization/prepolymerization of the core phase monomer and the water phase monomer is initiated, it is allowed to continue to allow for all or substantially all of the monomers to oligomerize/prepolymerize, generally from 3 to 5 hours. Once completed, the temperature of the reaction vessel is raised again to the activation temperature of the second core phase and water phase initiators. Again, it is desirable to select second initiators whose primary activation temperature is the same or fairly close to one another, generally within 5° C. of each other, more preferably within 2° C. of each other. Again, activation temperatures may be more widely differentiated, but such is not necessary (unless due to requirements of the monomers themselves) since it is desirable to have the shell wall build from the core phase and from the water phase concurrently. The higher temperatures of the second core phase and water phase initiators drive the cross-linking of the monomer/oligomer/prepolymer to form a strong polymer composition. Here, the higher temperature is maintained until the capsules are fully formed, generally from about 5 to 8 hours.

Although not critical to the basic embodiment of the present teaching, the rate of temperature increase in the activation of the initiators can also influence the ultimate performance and characteristics of the resultant microcapsules. In this regard it is preferred that temperature increases be performed over an extended period of time, preferably over a period of 25 to 40 minutes, more preferably about 30 minutes. The rate of increase during that period may vary from about 20° C. per hour to about 40° C. per hour. Of course these are general ranges and the same may be somewhat lower or somewhat higher depending upon the selected materials and the activation temperatures of the initiators.

Unless otherwise indicated, all ratios, percents, and proportions herein are on the basis of weight, and all measurements are in the metric system. Having described the present process in general and specific terms, attention is now directed to the following specific examples which demonstrate the marked benefit of the present process and of the microcapsules resulting therefrom.

EXAMPLES

A plurality of microencapsulation processes were performed as set forth below. The key ingredients employed are listed in Table 1. In order to test the properties of the formed microcapsules, they were subjected to a plurality of tests as follows.

TABLE 1

| Monomers | Chemistry | Solubility in water (g/L @ 25° C.) |
|---|---|---|
| SR206 | Ethylene glycol dimethacrylate | 2.4 |
| SR247 | Neopentyl glycol diacrylate | 0.94 |
| SR602 | Ethoxylated (10) bisphenol A diacrylate | |
| SR601 | Ethoxylated (4) bisphenol A diacrylate | 0.45 |
| SR256 | 2-(2-ethoxyethoxy) ethyl acrylate | 25.33 |
| SR259 | Polyethylene glycol 200 diacrylate | 40.68 |
| SR399 | DIPENTAERYTHRITOL PENTAACRYLATE | |
| SR349 | Ethoxylated (3) bisphenol A diacrylate | |
| SR9035 | 15-mole, ethoxylated, trimethylolpropane triacrylate | Water soluble |
| SR9038 | ethoxylated (30) bisphenol A diacrylate | Water soluble |
| SR344 | Polyethylene glycol 400 diacrylate | Water soluble |
| SR610 | polyethylene glycol (600) diacrylate | Water soluble |
| SR295 | PENTAERYTHRITOL TETRAACRYLATE | 4.23 |
| MMA | Methyl methacrylate | |
| V-50 | 2,2'-azobis(2-amidinopropane) hydrochloride - 10 hour ½ life at 56° C. | |
| Vazo-67 | 2,2'-azobis(2-methylbutyronitrile) - 10 hour ½ life at 67° C. | |
| VA-086 | 2,2'-Azobis[2-methyl-N-(2-hydroxyethyl)propionamide] - 10 hour ½ life at 86° C. | |
| Vazo-88 | 1,1'-Azobis(cyclohexanecarbonitrile) - 10 hour ½ life at 88° C. | |
| $Na_2SO_4$ | Sodium sulfate | |
| KPS | Potassium persulfate | |
| BPO | Benzyl peroxide | |
| Polywax™ M90 Wax | Alkanes | |
| PVA523 | Polyvinyl alcohol, partially hydrolyzed | |

Monomers SR206, SR247, SR295, SR256, SR259, SR344, SR349, SR399, SR601, SR602, SR610, SR9035 and SR9038 were supplied by Sartomer Americas (502 Thomas Jones Way, Exton, PA 19341, USA).
MMA, KPS and BPO were purchased from Sigma-Aldrich (3050 Spruce Street, Saint Louis, Missouri 63103, USA).
V-50 and VA-086 were supplied by Wako Chemicals USA, Inc. (1600 Bellwood Road, Richmond, VA 23237, USA).
Vazo-67 and Vazo-88 were supplied by E. I. du Pont de Nemours and Company, Wilmington, DE 19880.
PVA523 was purchased from Sekisui Specialty Chemicals America. LLC (1501 L B J Freeway, Suite 530, Dallas, TX 75234, USA), and sodium sulfate was supplied by Hydrite Chemical Co. (Oshkosh, WI 54902, USA).
Polywax™ M90 Wax was supplied by Baker Hughes, Inc., 12645 W. Airport Blvd., Suger Land, TX 77478

Free Wax

Samples of the microcapsule powders were obtained by drying the slurry in a Buchi Mini Spray Dryer B-290. The amount of free wax in the powders was determined by GC analysis using hexane wash. Approximately 0.2 grams of the dried capsules were combined with 10 ml of hexane in a 20 ml scintillation vial and capped tightly and placed on a vortex mixer for 5 seconds before being pipetted into an autosampler vial and analyze by Agilent 7890N GC with Chem Station Software. Column: Phenomenex's ZB-1HT Inferno column @10M, 0.32 mm, 0.25 µm, 100%-dimethylpolysiloxane phase or equivalent. Temp: 50° C. for 1 minute then heat to 270° C. @10° C./min. Injector 270° C. with Split Ration of 10:1. Detector: 320° C., 2 µl injection. The % free wax was calculated by dividing the mg of free wax measured by the sample weight (mg) and multiplying by 100. Free wax is an indicator of the permeability and/or strength of the capsule: a permeable and/or weak wall will show higher levels of free wax.

TGA Analysis

TGA analysis was performed at a temperature ramp up rate of 10° C./min in the TGA Q500 thermal gravimetric analyzer from TA Instruments. The temperature at 10% and 20% weight loss was recorded.

DSC (Differential Scanning Calorimetry) Analysis

Thermal properties of the encapsulated phase change materials are analyzed with DSC Q2000 from TA Instruments with a temperature ramp up rate of 1° C./min. The melting point, latent heat, supercooling %, and ΔT (temperature difference between melting peak and cooling peak) are recorded.

Monomer Solubility in Water

Solubility of the monomers in water is determined by combining 5 g of monomer and 5 g of deionized water in a sealed 20 ml vial for 30 min, after which the sample is allowed to sit at room temperature for 24 hours to establish equilibrium and phase separation of monomer from water. The water phase was then removed and analyzed to determine the monomer concentration GC/MS (7890B GC with a 5977A MSD Mass Spectrophotometer), both from Agilent. Inlet temperature at 270 C. Ramp starting at 100° C. to 320° C. at 10 degrees per min. The mass spec was scanning from a molecular weight of 30-500. The GC column was a Agilent DB-SMS 30M×0.250 mm.

Example 1

A microcapsule according to the present teaching was prepared using a two-part water phase and a single core phase. The composition/make up of each phase was as presented in Table 2.

TABLE 2

|  | Ingredients | Amount (g) |
|---|---|---|
| Water Phase I | Deionized Water | 186 |
|  | PVA523 (5%) | 124 |
| Capsule Core (IP) | Octadecane | 166.00 |
|  | Polywax ™ M90 wax | 1.66 |
|  | SR206 | 29.30 |
|  | Vazo-67 | 0.293 |
|  | Vazo-88 | 0.200 |
| Water Phase 2 | DI Water | 50 |
|  | PVA523(5%) | 33.3 |
|  | SR247 | 5.00 |
|  | V-50 | 0.50 |
|  | VA-086 | 0.20 |
|  | Total = | 596.45 |

As a first step in the preparation of the Example 1 microcapsules, a 5% PVA 523 stock solution was prepared by dissolving polyvinyl alcohol in deionized water at 85° C. for 30 minutes. Thereafter the first water phase component (WP1) was prepared by combining water with the stock PVA solution in a main reactor, mixing the same and elevating and holding the temperature at 55° C. Next, the second water phase component (WP2) was prepared by combining and mixing the stock PVA solution with water in a mixing tank at ambient temperature. Thereafter, the SR247 was added and mixed vigorously to form a suspension thereof in the stock PVA/water solution, following which the water phase initiators were added. The core phase composition was prepared by first dissolving Polywax™ M90 wax in octadecane at 70° C. for 10 minutes with mixing following which the SR206 monomer was added. The mixture was cooled to 55° C. and the oil soluble initiators added and the temperature maintained at 55° C. for 30 minutes.

In preparation for the encapsulation process, the main reactor was purged with pure nitrogen following which the core phase composition was added and the combined mixture milled until the desired droplet size was attained. Thereafter, the second water phase component (WP2) was added to the main reactor and the temperature of the mixture elevated to 75° C. over a 30 minute period and held at that temperature for an additional 4 hours. Thereafter, the temperature was further elevated to 85° C. over a 30 minute period and held at that temperature for an additional 6 hours. Following this processing, the reactor mix was allowed to cool to ambient temperature resulting in a slurry of the desired microcapsules.

Example 2

A series of microcapsules both according to the present teachings and comparative examples, showing the closest art, were prepared according to the same general methodology as presented in Example 1. The formulation of the water phase components and core phase composition were as presented in Table 3. Table 3 also presents the results attained therewith with respect to free wax and TGA as well as general observations made of the mixture and resultant product. Samples A-D are comparative examples and demonstrate a microcapsule whose shell wall is a copolymer, but wherein the copolymer is formed solely from multiple monomers in the core phase. This contrasts with the microcapsules made according to the present teachings wherein monomers contributed by both the core phase and the water phase are required. These comparative microcapsules did not manifest the strength and integrity sought and attained by those of the present teaching. Comparative examples E and F demonstrate microcapsules formed of the requisite core monomer, but again, without a water phase monomer. Again, the formed microcapsules do not attain the necessary physical properties. Comparative examples EE thru HH demonstrate the production of microcapsules according to the general process of the presently claimed method except that readily soluble water phase monomers are used rather than the requisite poor to moderately hydrophilic monomers. As indicated, all of these samples resulted in gelation of the water phase. The remaining examples all manifest various iterations of the method and resultant microcapsules according to the present teaching. As seen, variations in water phase monomer, initiator, one-step v, two-step formation, etc. all affected the resultant properties of the so formed microcapsules; however, all of the so formed microcapsules manifested consistent properties of strength and integrity. Finally, a comparison of comparative example E with example Z demonstrates the importance of the monomer coming from both phases as here the microcapsule wall is formed from the same monomer except that in example Z the monomer is contributed from both phases which allows building of the shell wall from both within as well as on its outer surface. Based on these results, it is also to be noted that microcapsule integrity, especially integrity as evidenced by free wax, manifested a direct correlation to the solubility of the water phase monomer as shown in FIG. 1.

TABLE 3

| Sample ID | Core Monomer - 30 g | Water Phase Monomer | Oil-phase initiators Vazo-67 g | Vazo-88 g | Water-phase initiators V-50 g | VA-086 g | Other | Na$_2$SO$_3$ | % Free Wax, Powders | TGA at 10%/20% w. loss), C | Observation |
|---|---|---|---|---|---|---|---|---|---|---|---|
| A | 95% SR206/ 5% SR256 | n/a | 0.3 | 0 | 0.0 | 0 | — | 0 | 5.46 | 182/230 | |
| B | 95% SR206/ 5% SR256 | n/a | 0.3 | 0 | 0.3 | 0 | — | 0 | 1.56 | 207/222 | thickened up |
| C | 95% SR206/ 5% SR256 | n/a | 0.3 | 0 | 0 | 0 | 0.3 g KPS | 0 | 2.97 | 199/222 | |
| D | 95% SR206/ 5% SR256 | n/a | 0.3 | 0 | 0 | 0 | 0.3 g BPO | 0 | 5.48 | | |
| E | SR206 | n/a | 0.3 | 0 | 0.1 | 0 | — | 0 | 1.76 | 203/221 | thickened up |
| F | SR206 | n/a | 0.3 | 0.2 | 0.1 | 0.2 | — | 0 | 2.05 | 202/220 | no thickening |
| G | SR206 | SR259, 5 g | 0.3 | 0.2 | 0.1 | 0.2 | — | 4 g | 3.27 | 197/223 | thickened up |
| H | SR206 | SR259, 5 g | 0.3 | 0.2 | 0.0 | 0.2 | — | 4 g | 7.65 | 193/220 | no thickening |
| I | SR206 | SR247, 5 g | 0.3 | 0.2 | 0.0 | 0.2 | — | 4 g | 4.31 | 178/200 | no thickening, no agglomeration |
| J | SR206 | SR247, 5 g | 0.3 | 0.2 | 0.1 | 0.2 | — | 4 g | 0.99 | 187/234 | no thickening, no agglomeration. |
| K | SR206 | SR247, 5 g | 0.3 | 0.2 | 0 | 0.2 | 0.3 g BPO | 4 g | 3.77 | 205/239 | no thickening, no agglomeration. |
| L | SR206 | SR247, 5 g | 0.3 | 0.2 | 0.1 | 0.2 | — | 0 | 0.38 | 214/233 | no thickening, no agglomeration |
| M | SR206 | SR247, 10 g | 0.3 | 0.2 | 0.1 | 0.2 | — | 0 | 0.50 | 214/235 | no thickening, no agglomeration |
| N | SR206 | SR247, 5 g | 0.3 | 0.2 | 0.1 | 0.2 | — | 0 | 0.53 | 213/233 | no thickening, no agglomeration |
| O | SR206 | SR247, 5 g | 0.3 | 0.2 | 0.0 | 0.2 | — | 0 | 3.43 | 203/239 | no thickening, no agglomeration |
| P | SR206 | SR247, 5 g | 0.3 | 0.2 | 0 | 0.2 | 0.3 g BPO | 0 | 2.62 | 208/240 | no thickening, no agglomeration |
| Q | SR206 | SR247, 5 g | 0.3 | 0.2 | 0.1 | 0.2 | — | 0 | 2.47 | 197/221 | one step process |
| R | SR206 | SR247, 5 g | 0.3 | 0 | 0.1 | 0.2 | — | 0 | 1.03 | 207/230 | |
| S | SR206 | SR247, 5 g | 0.3 | 0.2 | 0.1 | 0 | — | 0 | 0.89 | 207/230 | |
| T | SR206 | SR247, 5 g | 0.3 | 0.2 | 0.1 | 0.2 | | | 1.23 | 211/231 | 40% Solids a few aggregations <500u, dried ok |
| U | SR206 | SR247, 5 g | 0.3 | 0.2 | 0.1 | 0.2 | | | 1.05 | 208/230 | 40% Solids, one step, a few aggregations <400u, dried ok |
| V | 33% SR206/ 67% MMA | SR247, 5 g | 0.3 | 0.2 | 0.1 | 0.2 | | | 1.89 | 190/206 | |
| W | 67% SR206/ 33% MMA | SR247, 5 g | 0.3 | 0.2 | 0.1 | 0.2 | | | 0.68 | 188/211 | |
| X | 90% SR206/ 10% MMA | SR247, 5 g | 0.3 | 0.2 | 0.1 | 0.2 | | | 0.41 | 196/217 | |
| Y | SR206 | SR247, 20 g | 0.3 | 0.2 | 0.1 | 0.2 | | | 1.34 | | thickened up, agglomeration. |
| Z | SR206 | SR206, 5 g | 0.3 | 0.2 | 0.1 | 0.2 | | | 0.54 | 217/223 | |
| AA | SR206 | SR256, 5 g | 0.3 | 0.2 | 0.1 | 0.2 | | | 1.39 | 209/222 | |
| BB | SR206 | SR259, 5 g | 0.3 | 0.2 | 0.1 | 0.2 | | | 6.92 | 183/214 | |
| CC | SR206 | SR399, 5 g | 0.3 | 0.2 | 0.1 | 0.2 | | | 1.23 | 220/227 | |
| DD | SR206 | SR349, 5 g | 0.3 | 0.2 | 0.1 | 0.2 | | | 1.90 | 198/220 | |
| EE | SR206 | SR9035, 5 g | 0.3 | 0.2 | 0.0 | 0.2 | | | Water-soluble monomers in water phase, Batch gelled. | | |
| FF | SR206 | SR9038, 5 g | 0.3 | 0.2 | 0.0 | 0.2 | | | Water-soluble monomers in water phase, Batch gelled. | | |
| GG | SR206 | SR344, 5 g | 0.3 | 0.2 | 0.0 | 0.2 | | | Water-soluble monomers in water phase, Batch gelled. | | |
| HH | SR206 | SR610, 5 g | 0.3 | 0 | 0.0 | 0 | | | Water-soluble monomers in water phase, Batch gelled. | | |

Example 3

Microcapsules containing phase change materials according to the present invention are prepared using a process with a two-part water phase and a single core phase.

As a first step in the preparation of the Example 3 microcapsules, a 5% PVA 523 stock solution is prepared by dissolving polyvinyl alcohol in deionized water at 85° C. for 30 minutes. Thereafter the first water phase component (WP1) is prepared by combining 186 g deionized water with 124 g stock PVA solution in a main reactor, mixing the same and elevating and holding the temperature at 55° C. Next, the second water phase component (WP2) is prepared by combining and mixing 33.3 g stock PVA solution with 50 g deionized water in a 250 ml beaker at ambient temperature. Thereafter, 7 g SR247 is added and mixed vigorously to form a suspension thereof in the stock PVA/water solution, following which the water phase initiators V-50 and VA-086 are added.

The core phase composition is prepared in a reactor by first dissolving 1.66 g Polywax™ M90 Wax in 166 g octadecane at 70° C. for 10 minutes with mixing following which 29.3 g SR206 monomer is added. The mixture is cooled to 55° C. and the oil soluble initiators, 0.5 g V-50 and 0.2 g VA-086, are added. Temperature of the reactor is maintained at 55° C. for another 30 minutes.

In preparation for the encapsulation process, the main reactor is purged with pure nitrogen following which the core phase composition is added and the combined mixture milled until the desired droplet size is attained. Thereafter, the second water phase component (WP2) is added to the main reactor and the temperature of the mixture elevated to 75° C. over a 30 minute period and held at that temperature for an additional 4 hours. Thereafter, the temperature is further elevated to 85° C. over a 30 minute period and held at that temperature for an additional 6 hours. Following this processing, the reactor mix is allowed to cool to ambient temperature resulting in slurry of the desired microcapsules.

The resulting microcapsules were isolated and subjected to a number of physical tests to assess their physical properties and attributes. The results thereof are presented in Table 4.

Commercial Applications

The microcapsules formed according to the present teachings have a number of commercial applications. For convenience, before addressing specific application, the following definitions are presented as they pertain to the discussion on commercial applications.

TABLE 4

| | |
|---|---|
| Microcapsule Size, micron | 4.83 |
| Free Wax, % | 0.45 |
| TGA at 10% weight loss, ° C. | 215 |
| TGA at 20% weight loss, ° C. | 240 |
| Latent Heat, J/g | 188 |
| Supercooling, % | 25 |
| Melting Point, ° C. | 36.5 |
| ΔT, ° C. | 1.6 |

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to fine fragrances (e.g. perfumes, colognes eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein "cleaning and/or treatment compositions" means products comprising fluid laundry detergents, fabric enhancers, laundry and/or rinse additives, fluid dishwashing detergents, fluid hard surface cleaning and/or treatment compositions, fluid toilet bowl cleaners that may or may not be contained in a unit dose delivery product all for consumer, agricultural, industrial or institutional use.

The term "absorbent article" is used herein in a very broad sense including any article able to receive and/or absorb and/or contain and/or retain fluids and/or exudates, especially bodily fluids/bodily exudates. Exemplary absorbent articles in the context of the present invention are disposable absorbent articles. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical disposable absorbent articles according to the present invention are diapers, surgical and wound dressings, breast and perspiration pads, incontinence pads and pants, bed pads as well as absorbent articles for feminine hygiene like sanitary napkins, panty liners, tampons, interlabial devices or the like. Absorbent articles suitable for use in the present invention include any type of structures, from a single absorbent layer to more complex multi-layer structures. Certain absorbent articles include a fluid pervious topsheet, a backsheet, which may be fluid impervious and/or may be water vapor and/or gas pervious, and an absorbent element comprised there between, often also referred to as "absorbent core" or simply "core".

The term "Sanitary tissue product" or "tissue product" as used herein means a wiping implement for post-urinary and/or post-bowel movement cleaning (toilet tissue products), for otorhinolaryngological discharges (facial tissue products) and/or multi-functional absorbent and cleaning uses (absorbent towels such as paper towel products and/or wipe products). The sanitary tissue products of the present invention may comprise one or more fibrous structures and/or finished fibrous structures, traditionally, but not necessarily, comprising cellulose fibers.

The term "tissue-towel paper product" refers to products comprising paper tissue or paper towel technology in general, including, but not limited to, conventional felt-pressed or conventional wet-pressed tissue paper, pattern densified tissue paper, starch substrates, and high bulk, uncompacted tissue paper. Non-limiting examples of tissue-towel paper products include towels, facial tissue, bath tissue, table napkins, and the like.

"Personal care composition" refers to compositions intended for topical application to skin or hair and can be, for example, in the form of a liquid, semi-liquid cream, lotion, gel, or solid. Examples of personal care compositions can include, but are not limited to, bar soaps, shampoos, conditioning shampoos, body washes, moisturizing body washes, shower gels, skin cleansers, cleansing milks, in-shower body moisturizers, pet shampoos, shaving preparations, etc.

"Bar soap" refers to compositions intended for topical application to a surface such as skin or hair to remove, for example, dirt, oil, and the like. The bar soaps can be rinse-off formulations, in which the product is applied topically to the skin or hair and then subsequently rinsed within minutes from the skin or hair with water. The product could also be wiped off using a substrate. Bar soaps can be in the form of a solid (e.g., non-flowing) bar soap intended for topical application to skin. The bar soap can also be in the form of a soft solid which is compliant to the body. The bar soap additionally can be wrapped in a substrate which remains on the bar during use.

"Rinse-off" means the intended product usage includes application to skin and/or hair followed by rinsing and/or wiping the product from the skin and/or hair within a few seconds to minutes of the application step.

"Ambient" refers to surrounding conditions at about one atmosphere of pressure, 50% relative humidity and about 25° C.

"Anhydrous" refers to compositions and/or components which are substantially free of added or free water.

"Antiperspirant composition" refers to antiperspirant compositions, deodorant compositions, and the like. For example, antiperspirant creams, gels, soft solid sticks, body sprays, and aerosols.

"Soft solid" refers to a composition with a static yield stress of about 200 Pa to about 1,300 Pa. The term "solid" includes granular, powder, bar and tablet product forms.

The term "fluid" includes liquid, gel, paste and gas product forms.

The term "situs" includes paper products, fabrics, garments, hard surfaces, hair and skin.

The term "substantially free of" refers to about 2% or less, about 1% or less, or about 0.1% or less of a stated ingredient. "Free of" refers to no detectable amount of the stated ingredient or thing.

As used herein, the terms "a" and "an" mean "at least one".

As used herein, the terms "include", "includes" and "including" are meant to be non-limiting.

Unless specifically stated otherwise, the test methods disclosed in the Test Methods Section of the present application should be used to determine the respective values of the parameters of Applicants' inventions.

Unless otherwise noted, in discussing the commercial applications below, all component or composition levels are in reference to the active portion of that component or composition, and are exclusive of impurities, for example, residual solvents or by-products, which may be present in commercially available sources of such components or compositions.

Similarly, all percentages and ratios are calculated by weight unless otherwise indicated and are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Consumer Products

A method of making a consumer product comprising combining a consumer product ingredient and microcapsules made by a method comprising (a) forming a dispersion of a hydrophobic oil phase composition comprising a hydrophobic material and one or more polymerizable ethylenically unsaturated monomers, the core monomer, that are wholly or partially soluble in the hydrophobic material in a water or water-based solution, the continuous phase, said continuous phase comprising water and at least one or more ethylenically unsaturated polymerizable monomers, the water phase monomer, all or a portion of which are poorly to moderately hydrophilic, (b) subjecting the dispersion to one or more conditions that initiate or effectuate the polymerization of the water phase and core monomers, (c) maintaining the dispersion under such conditions as effectuate polymerization of the monomers until such time as the full capsule walls are formed and, optionally, thereafter (d) isolating the formed microcapsules from the continuous phase, is disclosed.

In one aspect of said method, prior to or concurrent with step (a), the oil phase composition is subjected to such conditions as will induce oligomerization/pre-polymerization of the monomer in the oil phase composition.

In one aspect of said method, the emulsion is subjected to conditions that induce or promote the movement of the polymerizable monomers and/or an oligomer/prepolymer of said core monomers and/or water phase monomers within the core material and within the continuous phase, respectively, to the interface of the oil phase composition and the aqueous phase concurrent with the polymerization thereof.

In one aspect of said method, said conditions of said movement is effected by the oligomerization or pre-polymerization of the monomer.

In one aspect of said method, step (b) comprises a two or more step polymerization processes wherein in a first step at least one of the core monomer and the water phase monomer or both in the oil phase composition or water phase composition, respectively, is subjected to conditions that initiate or effectuate the oligomerization or pre-polymerization of the said monomer and in a second or subsequent step the dispersion is subjected to one or more conditions that initiates or effectuates the full polymerization of the polymerizable monomers including the oligomers/prepolymers and any remaining monomer of the oligomerization/pre-polymerization step.

In one aspect of said method, the monomers of both the oil phase composition and the water phase composition are subjected to conditions that effectuate the oligomerization or prepolymerization of the monomers in each of said phases.

In one aspect of said method, the conditions which effect oligomerization and/or prepolymerization of the monomers of each phase is the same and said oligomerization or pre-polymerization occurs concurrently in each phase.

In one aspect of said method, the conditions which effect oligomerization and/or pre-polymerization are different and occur in sequence.

In one aspect of said method, following completion of the oligomerization/pre-polymerization step, the dispersion is subjected to such conditions as will initiate or effectuate the full polymerization of the monomers, including the already formed oligomers and prepolymers, and building of the microcapsule wall or shell at the interface of the oil phase composition and the continuous phase.

In one aspect of said method, the microcapsules are formed in a sequential manner with at least one of the core phase and water phase monomer, preferably both, undergoing a two-step polymerization whereby oligomerization/pre-polymerization of each monomer material is initiated and maintained for a period of time in their respective phases and full polymerization of each occurs subsequently at the interface of the oil phase composition and continuous phase, with the oligomers/pre-polymers continuing to build upon the wall as it forms: the core phase monomers building on the inner surface of the shell and the water phase monomers building upon the outer surface of the shell.

In one aspect of said method, each of the oil phase composition and the water phase composition contains at least one initiator for effecting or initiating the polymerization of the monomers of each phase.

In one aspect of said method, at least two initiators are present in the oil phase composition or the water phase composition or both if the monomer of said oil phase composition, said water phase composition or both, respectively, is to be subjected to oligomerization/pre-polymerization.

In one aspect of said method, the two step shell formation is achieved through the use of four initiators, two in each phase, each initiator in each phase being initiated or activated by different conditions and/or having a different rate of activation under the same conditions, whereby the first of each pair of initiators is initiated or activated to effect formation of the oligomers/pre-polymer of each shell forming monomer and a period of time allowed to lapse before activation of the second initiator in each phase which then causes the full polymerization of the oligomers/pre-polymers and rapid shell wall formation.

In one aspect of said method, the first of each pair of initiators in each phase is activated by the same or similar conditions and each of second of each pair of initiators in each phase is activated by the same or similar conditions.

In one aspect of said method, the monomers of each of the oil phase composition and the water phase composition are capable of copolymerization.

In one aspect of said method, a sufficient amount of said microcapsules is combined with said at least one consumer product ingredient to provide, based on total consumer product weight, said consumer product with from 0.001% about to about 25%, preferably from about 0.01% to about 10%, more preferably from about 0.05% to about 5%, most preferably from about 0.1% to about 0.5% of said microcapsules.

A consumer product produced by any preceding method is disclosed

Benefit Agents That Can Serve as Core Material for Microcapsules

Useful core materials include perfume raw materials, sensates, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers and anti-foaming agents, UV protection agents for fabrics and skin, sun fade inhibitors, anti-allergenic agents, enzymes, water proofing agents, fabric comfort agents, shrinkage resistance agents, stretch resistance agents, stretch recovery agents, skin care agents, glycerin, and natural actives such as aloe vera, vitamin E, shea butter, cocoa butter, and the like, brighteners, antibacterial actives, antiperspirant actives, cationic polymers, dyes and mixtures thereof. In one aspect, said perfume raw material is selected from the group consisting of alcohols, ketones, aldehydes, esters, ethers, nitriles alkenes. In one aspect the core material comprises a perfume. In one aspect, said perfume comprises perfume raw materials selected from the group consisting of alcohols, ketones, aldehydes, esters, ethers, nitriles alkenes and mixtures thereof. In one aspect, said perfume may comprise a perfume raw material selected from the group consisting of perfume raw materials having a boiling point (B.P.) lower than about 250° C. and a C log P lower than about 3, perfume raw materials having a B.P. of greater than about 250° C. and a C log P of greater than about 3, perfume raw materials having a B.P. of greater than about 250° C. and a C log P lower than about 3, perfume raw materials having a B.P. lower than about 250° C. and a C log P greater than about 3 and mixtures thereof. Perfume raw materials having a boiling point B.P. lower than about 250° C. and a C log P lower than about 3 are known as Quadrant I perfume raw materials, perfume raw materials having a B.P. of greater than about 250° C. and a C log P of greater than about 3 are known as Quadrant IV perfume raw materials, perfume raw materials having a B.P. of greater than about 250° C. and a C log P lower than about 3 are known as Quadrant II perfume raw materials, perfume raw materials having a B.P. lower than about 250*C and a C log P greater than about 3 are known as a Quadrant III perfume raw materials. In one aspect, said perfume comprises a perfume raw material having B.P. of lower than about 250° C. In one aspect, said perfume comprises a perfume raw material selected from the group consisting of Quadrant I, II, III perfume raw materials and mixtures thereof. In one aspect, said perfume comprises a Quadrant III perfume raw material. Suitable Quadrant I, II, III and IV perfume raw materials are disclosed in U.S. Pat. No. 6,869,923 B1.

In one aspect, said perfume comprises a Quadrant IV perfume raw material. While not being bound by theory, it is believed that such Quadrant IV perfume raw materials can improve perfume odor "balance". Said perfume may comprise, based on total perfume weight, less than about 30%, less than about 20%, or even less than about 15% of said Quadrant IV perfume raw material.

Additional Consumer Product Specifics

Additional consumer product specifics are found below. Such disclosure is also intended to cover the process of making the disclosed consumer products wherein said process comprises combing the materials as disclosed to form the described consumer product.

Cleaning and/or Treatment Compositions and Methods of Use

Preferably, said consumer product is a cleaning and/or treatment composition having a viscosity of from about 10 mPa·s to about 50,000 mPa·s, preferably from about 50 mPa·s to about 2000 mPa·s, most preferably from about 75 mPa·s to about 400 mPa·s, a pH from about 3 to about 10, preferably from about 4 to about 8, most preferably from about 5 to about 8, said composition comprising, based on total cleaning and/or treatment composition weight with from 0.001% about to about 25%, preferably from about 0.01% to about 10%, more preferably from about 0.05% to about 5%, most preferably from about 0.1% to about 0.5% of the microcapsules disclosed here in.

As the viscosity range of the cleaning and/or treatment composition is tightened, it is easier to suspend certain materials such as polymers and waxes.

Preferably said cleaning and/or treatment composition comprises:
(a) a surfactant selected from the group consisting of nonionic surfactants, anionic surfactants, cationic surfactants, ampholytic surfactants, zwitterionic surfactants, semi-polar nonionic surfactants and mixtures thereof;
(b) a solvent wherein the solvent is preferably selected from the group consisting of hydrogenated castor oil, glycols, alcohols, and mixtures thereof;
(c) a fabric softener active wherein the fabric softener active is preferably selected from the group consisting of a quaternary ammonium compound, an amine and mixtures thereof, preferably said quaternary ammonium compound is selected from the group consisting of bis-(2-hydroxypropyl)-dimethylammonium methylsulphate fatty acid ester, 1,2-di(acyloxy)-3-trimethylammoniopropane chloride, N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl)N-(2 hydroxyethyl)N-methyl ammonium methylsulfate, 1,2 di-(stearoyl-oxy) 3 trimethyl ammoniumpropane chloride, dicanoladimethylammonium chloride, di(hard)tallowdimethylammonium chloride, dicanoladimethylammonium methylsulfate, 1-methyl-1-stearoylamidoethyl-2-stearoylimidazolinium methylsulfate, 1-tallowylamidoethyl-2-tallowylimidazoline, dipalmethyl hydroxyethylammoinum methosulfate and mixtures thereof, and
(d) mixtures of (a) through (c).

Preferably said cleaning and/or treatment composition, comprises an adjunct ingredient selected from the group consisting of builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, carriers, structurants, hydrotropes, processing aids, solvents in addition to said solubilizing agent, a fabric softener active selected from the group consisting of a silicone polymer, a polysaccharide, a clay, a fatty ester, a dispersible polyolefin, a polymer latex and mixtures thereof, pigments, and mixtures thereof, preferably said composition comprises an organic acid, preferably citric acid and/or lactic acid, hydrogenated castor oil, ethoxylated polyethleneimines, preferably PEI 600 EO 20 and/or PEI 600, an enzyme, preferably a cold water amylase, cold water protease and/or xylogluconase.

In one aspect of Applicants' cleaning and/or treatment composition, said cleaning and/or treatment composition comprises a fabric softener active selected from the group consisting of a quaternary ammonium compound, a silicone polymer, a polysaccharide, a clay, an amine, a fatty ester, a dispersible polyolefin, a polymer latex and mixtures thereof, preferably
(a) said quaternary ammonium compound comprises an alkyl quaternary ammonium compound, preferably said alkyl quaternary ammonium compound is selected from the group consisting of a monoalkyl quaternary ammonium compound, a dialkyl quaternary ammonium compound, a trialkyl quaternary ammonium compound and mixtures thereof;
(b) said silicone polymer is selected from the group consisting of cyclic silicones, polydimethylsiloxanes, aminosilicones, cationic silicones, silicone polyethers, silicone resins, silicone urethanes, and mixtures thereof;
(c) said polysaccharide comprises a cationic starch;
(d) said clay comprises a smectite clay;
(e) said dispersible polyolefin is selected from the group consisting of polyethylene, polypropylene and mixtures thereof; and
(f) said fatty ester is selected from the group consisting of a polyglycerol ester, a sucrose ester, a glycerol ester and mixtures thereof.

In one aspect of Applicants' cleaning and/or treatment composition, said cleaning and/or treatment composition comprises a fabric softener active comprising a material selected from the group consisting of monoesterquats, diesterquats, triesterquats, and mixtures thereof, preferably, said monoesterquats and diesterquats are selected from the group consisting of bis-(2-hydroxypropyl)-dimethylammonium methylsulfate fatty acid ester and isomers of bis-(2-hydroxypropyl)-dimethylammonium methylsulfate fatty acid ester and/or mixtures thereof, 1,2-di(acyloxy)-3-trimethylammoniopropane chloride, N,N-bis(stearoyl-oxy-ethyl)-N,N-dimethyl ammonium chloride, N,N-bis(tallowoyl-oxy-ethyl)-N,N-dimethyl ammonium chloride, N,N-bis(stearoyl-oxy-ethyl)-N-(2-hydroxyethyl)-N-methyl ammonium methylsulfate, N,N-bis-(stearoyl-2-hydroxypropyl)-N,N-dimethylammonium methylsulfate, N,N-bis-(tallowoyl-2-hydroxypropyl)-N,N-dimethylammonium methyisulfate, N,N-bis-(palmitoyl-2-hydroxypropyl)-N,N-dimethylammonium methylsulfate, N,N-bis-(stearoyl-2-hydroxypropyl)-N,N-dimethylammonium chloride, 1,2-di-(stearoyl-oxy)-3-trimethyl ammoniumpropane chloride, dicanoladimethylammonium chloride, di(hard)tallowdimethylammonium chloride, dicanoladimethylammonium methylsulfate, 1-methyl-1-stearoylamidoethyl-2-stearoylimidazolinium methylsulfate, 1-tallowylamidoethyl-2-tallowylimidazoline, dipalmytmethyl hydroxyethyltammoinum methylsulfate and mixtures thereof.

In one aspect of Applicants' cleaning and/or treatment composition, said composition comprises a quaternary ammonium compound and a silicone polymer, preferably said composition comprises from 0.001% to 10%, from 0.1% to 8%, more preferably from 0.5% to 5%, of said silicone polymer.

In one aspect of Applicants' cleaning and/or treatment composition, said fabric softening active has an Iodine Value of between 0-140, preferably 5-100, more preferably 10-80, even more preferably, 15-70, most preferably 18-25 or when said fabric softening active comprises a partially hydrogenated fatty acid quaternary ammonium compound said fabric softening active most preferably has a Iodine Value of 25-60.

In one aspect of Applicants' cleaning and/or treatment composition, said cleaning and/or treatment composition is a soluble unit-dose product said soluble unit dose product comprising one or more cleaning and/or treatment compositions contained within one or more chambers said chambers being formed from one or more films, preferably said one or more films comprise PVA film.

The compositions of the present invention may be used in any conventional manner.

In short, they may be used in the same manner as products that are designed and produced by conventional methods and processes. For example, compositions of the present invention can be used to treat a situs inter alia a surface or fabric. Typically at least a portion of the situs is contacted with an aspect of Applicants' composition, in neat form or diluted in a wash liquor, and then the situs is optionally washed and/or rinsed. For purposes of the present invention, washing includes but is not limited to, scrubbing, and mechanical agitation. The fabric may comprise any fabric capable of being laundered in normal consumer use conditions. When the wash solvent is water, the water temperature typically ranges from about 5° C. to about 90° C. and, when the situs comprises a fabric, the water to fabric mass ratio is typically from about 1:1 to about 100:1.

The cleaning and/or treatment compositions of the present invention may be used as liquid fabric enhancers wherein they are applied to a fabric and the fabric is then dried via line drying and/or drying the an automatic dryer.

In one aspect, a method of controlling malodors comprising: contacting a situs comprising a malodor and/or a situs that will become malodorous with a cleaning and/or treatment composition selected from the group consisting of Applicants' cleaning and/or treatment compositions and mixtures thereof, is disclosed.

In one aspect of Applicants' method, said situs comprises a fabric and said contacting step comprises contacting said fabric with a sufficient amount of Applicants' cleaning and/or treatment compositions to provide said fabric with at least 0.0025 mg of benefit agent, such as perfume, per kg of fabric, preferably from about 0.0025 mg of benefit agent/kg of fabric to about 50 mg of malodor reduction material/kg of fabric, more preferably from about 0.25 mg of benefit agent/kg of fabric to about 25 mg of benefit agent/kg of fabric, most preferably from about 0.5 of benefit agent/kg of fabric to about 10 mg of benefit agent/kg of fabric of said sum of malodor reduction materials.

Solid Consumer Products and Methods of Use

Preferably said consumer product is a powder, granule, flake, bar or bead, said consumer product comprising, based on total product weight:
(a) with from 0.001% about to about 25%, preferably from about 0.01% to about 10%, more preferably from about 0.05% to about 5%, most preferably from about 0.1% to about 0.5% of the microcapsules disclosed here in;

(b) a carrier that is a solid at 25° C., preferably said solid carrier is selected from the group consisting of clays, sugars, salts, silicates, zeolites, citric acid, maleic acid, succinic acid, benzoic acid, urea and polyethylene oxide and mixtures thereof; preferably said carriers is present at a level of:
  (i) from about 20% to about 95%, more preferably about 30% to about 90%, even more preferably about 45% to about 90%, and most preferably about 60% to about 88%; or
  (ii) from about 1% to about 60%, more preferably about 2% to about 50%, even more preferably about 3% to about 45% and most preferably, about 4% to about 40%; and
(c) optionally, 0.5% to about 50% of an enzyme stable polymer, preferably said enzyme stable polymer is selected from the group consisting of polyacrylate polymers, polyamine polymer, acrylate/maleate copolymer, a polysaccharide, and mixtures thereof, preferably said polysaccharide is selected from the group consisting of carboxy methyl cellulose, cationic hydroxy ethyl cellulose and mixtures thereof.

In one aspect of said product, said product comprises a perfume.

In one aspect of said product, said product comprising an additional material that is an adjunct ingredient selected from the group consisting of surfactants, builders, chelating agents, dye transfer inhibiting agents, dispersants, enzymes, and enzyme stabilizers, catalytic materials, bleach activators, a fabric softener active, hydrogen peroxide, sources of hydrogen peroxide, preformed peracids, polymeric dispersing agents, day soil removal/anti-redeposition agents, brighteners, suds suppressors, dyes, hueing dyes, perfumes, perfume delivery systems, structure elasticizing agents, carriers, structurants, hydrotropes, processing aids, solvents, pigments and mixtures thereof.

The compositions of the present invention may be used in any conventional manner. In short, they may be used in the same manner as products that are designed and produced by conventional methods and processes. For example, compositions of the present invention can be used to treat a situs inter alia a surface or fabric. Typically at least a portion of the situs is contacted with an aspect of Applicants' composition, in neat form or diluted in a wash liquor, and then the situs is optionally washed and/or rinsed. For purposes of the present invention, washing includes but is not limited to, scrubbing, and mechanical agitation. The fabric may comprise any fabric capable of being laundered in normal consumer use conditions. When the wash solvent is water, the water temperature typically ranges from about 5° C. to about 90° C. and, when the situs comprises a fabric, the water to fabric mass ratio is typically from about 1:1 to about 100:1.

The compositions of the present invention may be used as fabric enhancers wherein they are applied to a fabric and the fabric is then dried via line drying and/or drying the an automatic dryer.

A method of freshening comprising: contacting a situs comprising with a product selected from the group consisting of the products described herein and mixtures thereof, is disclosed.

Freshening Compositions, Methods of Use and Delivery Systems

Preferably, said consumer product is a freshening composition having a viscosity of from about 1 mPa·s to about 50,000 mPa·s, preferably from about 1 mPa·s to about 2000 mPa·s, most preferably from about 1 mPa·s to about 400 mPa·s, a pH from about 3 to about 10, preferably from about 4 to about 8, most preferably from about 5 to about 8, said freshening composition comprising, based on total freshening composition weight:
  (a) with from 0.001% about to about 25%, preferably from about 0.01% to about 10%, more preferably from about 0.05% to about 5%, most preferably from about 0.1% to about 0.5% of the microcapsules disclosed here in; and
  (b) from about 0.01% to about 3%, preferably from about 0.4% to about 1%, more preferably from about 0.1% to about 0.5%, most preferably from about 0.1% to about 0.3% of solublizing agent, preferably said solublizing agent is selected from the group consisting of a surfactant, a solvent and mixtures thereof,
    (i) preferably said surfactant comprises a non-ionic surfactant;
    (ii) preferably said solvent comprises an alcohol, a polyol and mixtures thereof;
  (c) optionally, an adjunct ingredient.

As the viscosity is lowered you obtain improved sprayability and improved penetration into fabric.

In one aspect of said freshening composition, said composition comprises an adjunct ingredient selected from the group consisting of isoalkanes comprising at least 12 carbon atoms, a compound comprising a quaternary amine moiety, lubricants, additional solvents, glycols, alcohols, silicones, preservatives, anti-microbial agents, pH modifiers, a carrier, insect repellants, metallic salts, cyclodextrins, functional polymers, anti-foaming agents, antioxidants, oxidizing agents, chelants and mixtures thereof: preferably lubricants wherein the lubricants preferably comprise hydrocarbons, more preferably hydrocarbons that comprise two or more branches or compounds comprising a quaternary amine moiety comprising at least 10 carbon atoms.

A device comprising Applicants' freshening compositions, said device being preferably selected from the group consisting of trigger sprayers, manual aerosol sprayers, automatic aerosol sprayers, wick containing devices, fan devices, and thermal drop-on-demand devices, is disclosed.

A method of freshening comprising: contacting a situs with a composition selected from the group consisting of the freshening compositions disclosed herein and mixtures thereof is disclosed.

In one aspect of said method, said contacting step comprises contacting said situs with a sufficient amount of the compositions disclosed herein to provide said situs with, from about 0.1 milligrams (mg) to about 10,000 mg, preferably from about 1 mg to about 5,000 mg most preferably from about 5 mg to about 1000 mg of a benefit agent, preferably a perfume, per square meter of projected surface area of said situs.

The composition of the present invention may be used with a hard surface cleaner, as is commonly used to clean countertops, tables and floors. A suitable floor cleaning liquid is sold by the instant assignee in a replaceable reservoir under the name WetJet. The cleaning solution may particularly be made according to the teachings of commonly assigned U.S. Pat. No. 6,814,088. The reservoir may be used with and dispensed from a floor cleaning implement, in conjunction with a disposable floor sheet. A suitable spray implement is also sold under the name WetJet. A suitable reservoir and fitment therefore may be made according to the teachings of commonly assigned U.S. Pat. Nos. 6,386,392 and/or 7,172,099. If desired the floor cleaning implement may dispense steam, according to the teachings of jointly assigned US 2013/0319463. Alternatively a refillable reservoir may be utilized.

If desired the composition of the present invention may be used with a pre-moistened sheet. If the cleaning sheet is pre-moistened, it is preferably pre-moistened with a liquid which provides for cleaning of the target surface, such as a floor, but yet does not require a post-cleaning rinsing operation. The cleaning sheet may be loaded with at least 1, 1.5 or 2 grams of cleaning solution per gram of dry substrate, but typically not more than 5 grams per gram. The cleaning solution may comprise a surfactant, such as APG surfactant which minimizes streaking since there is typically not a rinsing operation, according to the teachings of U.S. Pat. No. 6,716,805.

The composition of the present invention may be used for raised hard surfaces, as is sold under the names Mr. Clean and Mr. Proper. The composition may be dispensed from a trigger sprayer or aerosol sprayer, as are well known in the art. An aerosol sprayer dispenses the composition using propellant pressure, while a trigger sprayer dispenses the composition by pumping the composition under manual actuation. A suitable aerosol dispenser may have a dip tube or bag on valve, according to US 2015/0108163 and/or US 2011/0303766. A suitable trigger sprayer is found in U.S. Pat. No. 8,322,631.

The present freshening composition may be used in a device for the delivery of a volatile material to the atmosphere or on inanimate surfaces (e.g. fabric surfaces as a fabric refresher). Such device may be configured in a variety of ways. For example, the device may be configured for use as an energized air freshener (i.e. powered by electricity; or chemical reactions, such as catalyst fuel systems; or solar powered; or the like). Exemplary energized air freshening devices include a powered delivery assistance means which may include a heating element, fan assembly, or the like. More particularly, the device may be an electrical wall-plug air freshener as described in U.S. Pat. No. 7,223,361; a battery (including rechargeable battery) powered air freshener having a heating and/or fan element. In energized devices, the volatile material delivery engine may be placed next to the powered delivery assistance means to diffuse the volatile perfume material. The volatile perfume material may be formulated to optimally diffuse with the delivery assistance means.

Alternatively, the device may be configured for use as a non-energized air freshener. An exemplary non-energized air freshener includes a reservoir and, optionally, capillary or wicking means or an emanating surface, to help volatile materials passively diffuse into the air (i.e. without an energized means). A more specific example includes a delivery engine having a liquid reservoir for containing a volatile material and a microporous membrane enclosing the liquid reservoir as disclosed in U.S. Pat. Nos. 8,709,337 and 8,931,711.

The device may also be configured for use as an aerosol sprayer or a non-aerosol air sprayer including traditional trigger sprayers as well as trigger sprayer having a pre-compression and/or buffer system for fluid therein. In this embodiment, the delivery engine can deliver volatile materials upon user demand or programmed to automatically deliver volatile materials to the atmosphere.

The apparatus may also be configured for use with an air purifying system to deliver both purified air and volatile materials to the atmosphere. Non-limiting examples include air purifying systems using ionization and/or filtration technology for use in small spaces (e.g. bedrooms, bathrooms, automobiles, etc.), and whole house central air conditioning/heating systems (e.g. HVAC).

Article and Method of Use

Preferably said consumer product is an article comprising
(a) a substrate, preferably a flexible substrate, more preferably a flexible substrate that is a sheet; preferably said substrate comprises a fabric softening active, preferably said fabric softening active coats all or a portion of said substrate; and
(b) based on total article weight with from 0.001% about to about 25%, preferably from about 0.01% to about 10%, more preferably from about 0.05% to about 5%, most preferably from about 0.1% to about 0.5% of the microcapsules disclosed here in.

Preferably said article has a weight ratio of fabric softener active to dry substrate ranging from about 10:1 to about 0.5:1, preferably from about 5:1 to about 1:1, preferably said fabric softener active is selected from the group consisting of a quaternary ammonium compound, a silicone polymer, a polysaccharide, a day, an amine, a fatty ester, a dispersible polyolefin, a polymer latex and mixtures thereof.

In one aspect, said article has a weight ratio of fabric softener active to dry substrate ranging from about 10:1 to about 0.5:1, preferably from about 5:1 to about 1:1, preferably said fabric softener active is selected from the group consisting of
(a) a cationic fabric softener active, preferably a quaternary-ammonium fabric softener active, more preferably a di(long alkyl chain)dimethylammonium ($C_1$-$C_4$ alkyl) sulfate or chloride, preferably the methyl sulfate; an ester quaternary ammonium compound, an ester amine precursor of an ester quaternary ammonium compound, and mixtures thereof, preferably a diester quaternary ammonium salt;
(b) a carboxylic acid salt of a tertiary amine and/or ester amine;
(c) a nonionic fabric softener material, preferably fatty acid partial esters of polyhydric alcohols, or anhydrides thereof, wherein the alcohol or anhydride contains from about 2 to about 18 and preferably from about 2 to about 8 carbon atoms, and each fatty acid moiety contains from about 8 to about 30 and preferably from about 12 to about 20 carbon atoms;
(d) alkanolamides;
(e) fatty acids; and
(f) mixtures of the foregoing.

Preferably, said article comprises, based on total article weight, from 1% to 99% by weight, preferably from about 1% to about 80%, more preferably from about 20% to about 70%, most preferably from about 25% to about 60% of a fabric softening active.

Preferably said article comprises a quaternary ammonium compound selected from the group consisting of bis-(2-hydroxypropyl)-dimethylammonium methylsulphate fatty acid ester, 1,2-di(acyloxy)-3-trimethylammoniopropane chloride, N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl)N-(2 hydroxyethyl)N-methyl ammonium methylsulfate, 1,2 di(stearoyl-oxy) 3 trimethyl ammoniumpropane chloride, dicanoladimethylammonium chloride, di(hard)tallowdimethylammonium chloride, dicanoladimethylammonium methylsulfate, 1-methyl-1-stearoylamidoethyl-2-stearoylimidazolinium methylsulfate, 1-tallowylamidoethyl-2-tallowylimidazoline, dipalmethyl hydroxyethylammoinum methosulfate and mixtures thereof.

In one aspect of said article, said article comprises a fabric softening active having an Iodine Value of between 0-140, preferably 5-100, more preferably 10-80, even more preferably, 15-70, most preferably 18-25.

In one aspect of said article, said article comprises an adjunct ingredient selected from the group consisting of surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, day soil removal/anti-redeposition agents, brighteners, suds suppressors, dyes, hueing dyes, perfumes, perfume delivery systems, structure elasticizing agents, carriers, structurants, hydrotropes, processing aids, solvents, pigments anti-oxidants, colorants, preservatives, optical brighteners, opacifiers, stabilizers such as guar gum and polyethylene glycol, anti-shrinkage agents, anti-wrinkle agents, soil release agents, fabric crisping agents, reductive agents, spotting agents, germicides, fungicides, anti-corrosion agents, antifoam agents, Color Care Agents including Chlorine Scavengers, Dye Transfer Inhibitors, Dye Fixatives Chelants and Anti-Abrasion Agents Perfume, PMC's, Cyclodextrin Perfume Complexes, Free Cyclodextrin, Pro-Perfumes; Antioxidants and mixtures thereof.

A method of controlling softening and/or freshening comprising: contacting a situs comprising one or more of the articles Applicants' disclose herein, is disclosed.

In one aspect of said method, said situs comprises a fabric and said contacting step comprises contacting said fabric with a sufficient amount of Applicants' article containing to provide said fabric with a level of perfume of at least 0.0025 mg of perfume/kg of fabric, preferably from about 0.00025 mg of perfume/kg of fabric to about 25 mg of perfume/kg of fabric, more preferably from about 0.025 mg of perfume/kg of fabric to about 20 mg of perfume/kg of fabric, most preferably from about 0.25 of perfume/kg of fabric to about 10 mg of malodor reduction material/kg of fabric of said sum of malodor reduction materials.

One aspect of the present invention relates to fabric conditioning compositions which are delivered to fabric via dryer-added substrate that effectively releases the composition in an automatic laundry (clothes) dryer. Such dispensing means can be designed for single usage or for multiple uses. The dispensing means can also be a "carrier material" that releases the fabric conditioning composition and then is dispersed and/or exhausted from the dryer. When the dispensing means is a flexible substrate, e.g., in sheet configuration, the fabric conditioning composition is releasably affixed on the substrate to provide a weight ratio of conditioning composition to dry substrate ranging from about 10:1 to about 0.5:1, preferably from about 5:1 to about 1:1. To insure release, preferred flexible sheets withstand the dryer environment without decomposing or changing shape, e.g. combusting, creating off odors, or shrinking with heat or moisture. Substrates especially useful herein are rayon and/or polyester non-woven fabrics.

Non-limiting examples of the substrates useful herein are cellulosic rayon and/or polyester non-woven fabrics having basis weights of from about 0.4 oz./yd$^2$ to about 1 oz./yd$^2$, preferably from about 0.5 oz./yd$^2$ to about 0.8 oz./yd$^2$, more preferably from about 0.5 oz./yd$^2$ to about 0.6 oz./yd$^2$. These substrates are typically prepared using, e.g., rayon and/or polyester fibers having deniers of from about 1 to about 8, preferably from about 3 to about 6, and more preferably about 4 to 6 or mixtures of different deniers. Typically, the fiber is a continuous filament or a 3/16 inch to 2 inch fiber segment that is laid down, in a pattern that results in a multiplicity of layers and intersections between overlayed portions of the filament or fiber, on a belt, preferably foraminous, and then the fiber intersections are glued and/or fused into fiber-to-fiber bonds by a combination of an adhesive binder, and/or heat and/or pressure. As non-limiting examples, the substrate may be spun-bonded, melt-bonded, or point bonded or combinations of bonding processes may be chosen. The substrate breaking strength and elasticity in the machine and cross direction is sufficient to enable the substrate to be conveyed through a coating process. The porosity of the substrate article is sufficient to enable air flow through the substrate to promote conditioning active release and prevent dryer vent blinding. The substrate may also have a plurality of rectilinear slits extended along one dimension of the substrate.

The dispensing means will normally carry an effective amount of fabric conditioning composition. Such effective amount typically provides sufficient softness, antistatic effect and/or perfume deposition for at least one treatment of a minimum load in an automatic laundry dryer. Amounts of the fabric conditioning composition irrespective of load size for a single article can vary from about 0.1 g to about 100 g, preferably from about 0.1 g to about 20 g, most preferably from about 0.1 g to about 10 g. Amounts of fabric treatment composition for multiple uses, e.g., up to about 30, can be used.

Absorbent Article, Polybag or Paper Carton and Methods of Use

Preferably said consumer product is an article selected from an absorbent article, polybag or paper carton, said article comprising, based on total article weight, with from 0.001% about to about 25%, preferably from about 0.01% to about 10%, more preferably from about 0.05% to about 5%, most preferably from about 0.1% to about 0.5% of the microcapsules of the present invention.

Preferably said article is an absorbent article, preferably said absorbent article is a sanitary paper product, said sanitary paper product comprising one or more layers of conventional felt-pressed tissue paper, conventional wet-pressed tissue paper, pattern densified tissue paper, starch substrates, high bulk, un-compacted tissue paper and mixtures thereof.

Preferably said absorbent article comprises an absorbent core, and optionally a backsheet, topsheet, acquisition layer or outer wrapper, wherein said microcapsules are disposed on the absorbent core or between one or more of the optional layers.

In one aspect of said article, said absorbent article is contained in a polybag or paper carton.

In one aspect of said article, said microcapsules are disposed on said polybag or paper carton, and/or on said absorbent article.

Preferably said article is an absorbent article comprises a lotion.

Preferably, said absorbent article comprises one or more adjunct ingredients selected from the group consisting of surfactants, inks, dyes, mineral oils, petrolatum, polysiloxanes, cyclodextrins, clays, silicates, aluminates, vitamins, isoflavones, flavones, metal oxides, short chain organic acids ($C_1$-$C_8$), triglycerides ($C_8$-$C_{22}$), and antioxidants.

In one aspect, a method of providing a benefit agent, preferably perfume, comprising: incorporating said microcapsules in or on an article, preferably an absorbent article, polybag and/or paper carton, is disclosed.

A non-limiting list of suppliers of suitable absorbent articles, polybags, and cartons that can be used in the manufacture of Applicants' articles is as follows: Procter & Gamble of Cincinnati, Ohio, USA; International Paper Products of Memphis, Tenn. USA; and Kimberly Clark, of Irving, Tex. USA. Suitable equipment and processes for making absorbent articles can be obtained from Famec-canica Group of Pescara, Italy. Suitable equipment and processes for adding the malodor reduction materials to said articles can be obtained from Nordson of Duluth Ga., USA.

Personal Care Compositions and Methods of Use

Preferably said consumer product is a personal care composition comprising, based on total composition weight,
(a) with from 0.001% about to about 10%, preferably from about 0.1% to about 5%, more preferably from about 0.5% to about 4%, most preferably from about 1% to about 3% of the microcapsules disclosed here in;
(b) from about 0.1% to about 99%, preferably from about 1% to about 80%, more preferably from about 5% to about 70%, most preferably from about 10% to about 50% of a solvent, preferably said solvent is selected from, water, glycerin, and mixtures thereof; and
(c) from about 0% to about 50%, preferably from about 0% to about 40%, more preferably from about 0.1% to about 30%, most preferably from about 0.1% to about 15% of a material selected from the group consisting of a structurant, a humectant, a surfactant, an antimicrobial, and mixtures thereof.

Preferably, said personal care composition comprises one or more neat perfume raw materials—the total of said neat perfume raw materials being the sum of such neat perfume raw materials based on weight of each neat perfume raw materials.

Preferably, said sum total of neat perfume raw materials has an average Log P, based on weight percent of each perfume raw material in said sum total of neat perfume raw materials, of from about 2.5 to about 8, preferably from about 3 to about 8, more preferably from about 3.5 to about 7, most preferably, each of said neat perfume raw materials in said sum total of neat perfume raw materials. This range of Log P will allow the perfume to deposit on the skin and not wash away in the water phase during use Preferably said personal care composition, comprises less than 10%, preferably less than 5%, more preferably less than 1% of said one or more perfume raw materials, based on total combined weight of said one or more perfume raw materials comprise an ionone moiety.

Preferably said personal care composition comprises a total of, based on total personal care composition weight, of from about 3% to 30% of a surfactant, and, optionally, a miscellar phase and/or lamellar phase.

Preferably said personal care composition, said composition comprises a total, based on total personal care composition weight, of from about 0.1% to about 50% of a material selected from structurants, humectants, fatty acids, inorganic salts, antimicrobial agents, antimicrobial agents actives and mixtures thereof.

Preferably said personal care composition comprises an adjunct ingredient selected from the group consisting of clay mineral powders, pearl pigments, organic powders, emulsifiers, distributing agents, pharmaceutical active, topical active, preservatives, surfactants and mixtures thereof.

A method of freshening comprising: contacting a situs with a personal care composition selected from the group consisting of the personal care compositions disclosed herein is disclosed.

In one aspect of said method, said situs comprises the body or head of hair and said contacting step comprises contacting said body or hair containing a malodor with a sufficient amount of Applicants' personal care composition to provide said body or hair with a level of encapsulated benefit agent, preferably perfume, of at least 0.0001 mg of encapsulated benefit agent per body or head of hair, preferably from about 0.0001 mg of encapsulated benefit agent per body or head of hair to about 1 mg of encapsulated benefit agent per body or head of hair, more preferably from about 0.001 mg of encapsulated benefit agent per body or head of hair about 0.5 mg of encapsulated benefit agent per body or head of hair, most preferably from about 0.01 of encapsulated benefit agent per body or head of hair to about 0.2 mg of encapsulated benefit agent per body or head of hair.

Antiperspirant and/or Deodorant Compositions and Methods of Use

Preferably said consumer product is an antiperspirant and/or deodorant composition comprising, based on total composition weight,
(a) with from 0.001% about to about 10%, preferably from about 0.1% to about 5%, more preferably from about 0.5% to about 4%, most preferably from about 1% to about 3% of the microcapsules disclosed here in;
(b) from about 0.1% to about 99%, preferably from about 1% to about 80%, more preferably from about 5% to about 55%, most preferably from about 10% to about 50% of a solvent, preferably said solvent is selected from cyclopentasiloxane, ethanol, water, propylene glycol, dipropylene glycol, and mixtures thereof;
(c) from about 0% to about 30%, preferably from about 0% to about 20%, more preferably from about 0.1% to about 4%, most preferably from about 0.1% to about 4% of a material selected from the group consisting of a structurant, a residue masker, an antimicrobial, and mixtures thereof is disclosed. The aforementioned solvent levels help disperse perfume into the APDO base to give even coverage when used Preferably said antiperspirant and/or deodorant composition, comprises one or more perfume raw materials.

Preferably each of said one or more perfume raw materials has a boiling point of from about 160° C. to about 400° C., preferably from about 180° C. to about 400° C.

Preferably less than 10%, preferably less than 5%, more preferably less than 1% of said one or more perfume raw materials, based on total combined weight of said one or more perfume raw materials comprise an ionone moiety.

Preferably, said antiperspirant and/or deodorant composition is an antiperspirant composition that comprises a total of, based on total antiperspirant composition weight, from about 1% to about 25% of an aluminum salt antiperspirant active.

Preferably said antiperspirant and/or deodorant composition, is an anhydrous antiperspirant composition, said anhydrous antiperspirant composition comprising a total of, based on total anhydrous antiperspirant composition weight, from about 1% to about 25% of an antiperspirant actives selected from the group consisting of astringent metallic salts, preferably inorganic and organic salts of aluminum, zirconium and zinc, as well as mixtures thereof, more preferably aluminum halides, aluminum chlorohydrate, aluminum hydroxyhalides, zirconyl oxyhalides, zirconyl hydroxyhalides, and mixtures thereof.

Preferably said antiperspirant and/or deodorant composition comprises an adjunct ingredient selected from the group consisting of clay mineral powders, pearl pigments, organic powders, emulsifiers, distributing agents, pharmaceutical active, topical active, preservatives, surfactants and mixtures thereof.

A method of controlling malodors comprising: contacting a situs comprising a malodor and/or a situs that may become malodorous with an antiperspirant or deodorant composition selected from the group consisting of the antiperspirant and/or deodorant composition disclosed herein, is disclosed.

In one aspect of said method, said situs is an underarm and said contacting step comprises contacting said underarm with a sufficient amount of Applicants' antiperspirant and/or deodorant composition containing said sum of malodor reduction materials to provide said underarm with a level of malodor reduction materials of at least 0.0001 mg of malodor reduction material per underarm, preferably from about 0.0001 mg of malodor reduction material per underarm to about 10 mg of malodor reduction material per underarm, more preferably from about 0.001 mg of malodor reduction material per underarm about 5 mg of malodor reduction material per underarm, most preferably from about 0.01 of malodor reduction material per underarm to about 0.2 mg of malodor reduction material per underarm.

Antiperspirant Compositions

Antiperspirant compositions can be formulated in many forms. For example an antiperspirant composition can be, without limitation, a roll on product, a body spray, a stick including soft solid sticks and invisible solids, or an aerosol. Each of the antiperspirant compositions described below can include perfume materials as described herein.

A. Roll-On and Clear Gel

A roll-on antiperspirant composition can comprise, for example, water, emollient, solubilizer, deodorant actives, antioxidants, preservatives, or combinations thereof. A clear gel antiperspirant composition can comprise, for example, water, emollient, solubilizer, deodorant actives, antioxidants, preservatives, ethanol, or combinations thereof.

Water—The roll-on composition can include water. Water can be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the deodorant composition.

Emollients—Roll-on compositions can comprise an emollient system including at least one emollient, but it could also be a combination of emollients. Suitable emollients are often liquid under ambient conditions. Depending on the type of product form desired, concentrations of the emollient(s) in the deodorant compositions can range from about 1% to about 95%, from about 5% to about 95%, from about 15% to about 75%, from about 1% to about 10%, from about 15% to about 45%, or from about 1% to about 30%, by weight of the deodorant composition.

Emollients suitable for use in the roll-on compositions include, but are not limited to, propylene glycol, polypropylene glycol (like dipropylene glycol, tripropylene glycol, etc.), diethylene glycol, triethylene glycol, PEG-4, PEG-8, 1,2 pentanediol, 1,2 hexanediol, hexylene glycol, glycerin, C2 to C20 monohydric alcohols, C2 to C40 dihydric or polyhydric alcohols, alkyl ethers of polyhydric and monohydric alcohols, volatile silicone emollients such as cyclopentasiloxane, nonvolatile silicone emollients such as dimethicone, mineral oils, polydecenes, petrolatum, and combinations thereof. One example of a suitable emollient comprises PPG-15 stearyl ether. Other examples of suitable emollients include dipropylene glycol and propylene glycol.

Deodorant Actives—Suitable deodorant actives can include any topical material that is known or otherwise effective in preventing or eliminating malodor associated with perspiration. Suitable deodorant actives may be selected from the group consisting of antimicrobial agents (e.g., bacteriocides, fungicides), malodor-absorbing material, and combinations thereof. For example, antimicrobial agents may comprise cetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof. The concentration of the optional deodorant active may range from about 0.001%, from about 0.01%, of about 0.1%, by weight of the composition to about 20%, to about 10%, to about 5%, or to about 1%, by weight of the composition.

Odor Entrappers—The composition can include an odor entrapper. Suitable odor entrappers for use herein include, for example, solubilized, water-soluble, uncomplexed cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. The unique shape and physical-chemical property of the cavity enable the cyclodextrin molecules to absorb (form inclusion complexes with) organic molecules or parts of organic molecules which can fit into the cavity. Many perfume molecules can fit into the cavity.

Cyclodextrin molecules are described in U.S. Pat. Nos. 5,714,137, and 5,942,217. Suitable levels of cyclodextrin are from about 0.1% to about 5%, alternatively from about 0.2% to about 4%, alternatively from about 0.3% to about 3%, alternatively from about 0.4% to about 2%, by weight of the composition.

Buffering Agent—The composition can include a buffering agent which may be alkaline, acidic or neutral. The buffer can be used in the composition for maintaining the desired pH. The composition may have a pH from about 3 to about 10, from about 4 to about 9, from about 5 to about 8, from about 6 to about 7, or it may have a pH of about 6.5. One unique feature of the polyvinyl amine malodor control polymers is its ability to maintain active nitrogen sites at high pH levels which can help enhance the antibacterial effect which comes, at least in part, from the nitrogen sites. Suitable buffering agents include, for example, hydrochloric acid, sodium hydroxide, potassium hydroxide, and combinations thereof.

The compositions can contain at least about 0%, alternatively at least about 0.001%, alternatively at least about 0.01%, by weight of the composition, of a buffering agent. The composition may also contain no more than about 1%, alternatively no more than about 0.75%, alternatively no more than about 0.5%, by weight of the composition, of a buffering agent.

Solubilizer—The composition can contain a solubilizer. A suitable solubilizer can be, for example, a surfactant, such as a no-foaming or low-foaming surfactant. Suitable surfactants are nonionic surfactants, cationic surfactants, amphoteric surfactants, zwitterionic surfactants, and mixtures thereof.

Suitable solubilizers include, for example, hydrogenated castor oil, polyoxyethylene 2 stearyl ether, polyoxyethylene 20 stearyl ether, and combinations thereof. One suitable hydrogenated castor oil that may be used in the present composition is polyoxyethylene hydrogenated castor oil.

When the solubilizing agent is present, it is typically present at a level of from about 0.01% to about 5%, alternatively from about 0.01% to about 3%, alternatively from about 0.05% to about 1%, alternatively from about 0.01% to about 0.05%, by weight of the composition.

Preservatives—The composition can include a preservative. The preservative is included in an amount sufficient to prevent spoilage or prevent growth of inadvertently added microorganisms for a specific period of time, but not sufficient enough to contribute to the odor neutralizing performance of the composition. In other words, the preservative is not being used as the antimicrobial compound to kill microorganisms on the surface onto which the composition is deposited in order to eliminate odors produced by microorganisms. Instead, it is being used to prevent spoilage of the composition in order to increase shelf-life.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diol materials, isothiazclinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxymethyl) urea, commonly known as diazolidinyl urea, available under the trade name Germall® II from Sutton Laboratories, Inc.; N,N"-methylenebis{N'-[1-(hydroxymethyl)-2,5-dioxo-4-imidazolidinyl]-urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hüls America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative can range from about 0.0001% to about 0.5%, alternatively from about 0.0002% to about 0.2%, alternatively from about 0.0003% to about 0.1%, by weight of the composition.

B. Body Spray

A body spray can contain, for example, a carrier, perfume, a deodorant active, odor entrappers, propellant, or combinations thereof. The body spray compositions can be applied as a liquid.

Carrier—A carrier suitable for use in a body spray can include, water, alcohol, or combinations thereof. The carrier may be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the composition. A suitable example of an alcohol can include ethanol.

Propellant—The compositions described herein can include a propellant. Some examples of propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 diflouroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42%, or any combination thereof, by weight of the total fill of materials stored within the container.

C. Invisible Solid

Invisible solid antiperspirant compositions as described herein can contain a primary structurant, an antiperspirant active, a perfume, and additional chassis ingredient(s). The antiperspirant composition can further comprise other optional ingredient(s). The compositions can be in the form of a solid stick. The compositions can have a product hardness of about 600 gram force or more. The compositions may be free of dipropylene glycol, added water, castor wax, or any combination thereof. The antiperspirant composition may be anhydrous. The antiperspirant composition may be free of added water.

Hardness—The invisible solid can have a product hardness of least about 600 gram·force, more specifically from about 600 gram·force to about 5,000 gram·force, still more specifically from about 750 gram·force to about 2,000 gram·force, and yet more specifically from about 800 gram·force to about 1,400 gram·force.

The term "product hardness" or "hardness" as used herein is a reflection of how much force is required to move a penetration cone a specified distance and at a controlled rate into an antiperspirant composition under the test conditions described herein below. Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the peak force required to move a standard 45-degree angle penetration cone through the composition for a distance of 10 mm at a speed of 2 mm/second. The standard cone is available from Texture Technology Corp., as part number TA-15, and has a total cone length of about 24.7 mm, angled cone length of about 18.3 mm, and a maximum diameter of the angled surface of the cone of about 15.5 mm. The cone is a smooth, stainless steel construction and weighs about 17.8 grams.

Primary Structurants—The invisible solid can comprise a suitable concentration of a primary structurant to help provide the antiperspirant with the desired viscosity, rheology, texture and/or product hardness, or to otherwise help suspend any dispersed solids or liquids within the composition.

The term "solid structurant" as used herein means any material known or otherwise effective in providing suspending, gelling, viscosifying, solidifying, and/or thickening properties to the composition or which otherwise provide structure to the final product form. These solid structurants include gelling agents, and polymeric or non-polymeric or inorganic thickening or viscosifying agents. Such materials will typically be solids under ambient conditions and include organic solids, crystalline or other gellants, inorganic particulates such as days or silicas, or combinations thereof.

The concentration and type of solid structurant selected for use in the antiperspirant compositions will vary depending upon the desired product hardness, rheology, and/or other related product characteristics. For most structurants suitable for use herein, the total structurant concentration ranges from about 5% to about 35%, more typically from about 10% to about 30%, or from about 7% to about 20%, by weight of the composition.

Non-limiting examples of suitable primary structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fischer-Tropsch waxes, and microcrystalline wax; polyethylenes with molecular weight of 200 to 1000 daltons; solid triglycerides; behenyl alcohol, or combinations thereof.

Other non-limiting examples of primary structurants suitable for use herein are described in U.S. Pat. Nos. 5,976,514 and 5,891,424, the descriptions of which are incorporated herein by reference.

Antiperspirant Active—The antiperspirant stick compositions can comprise a particulate antiperspirant active suitable for application to human skin. The concentration of antiperspirant active in the composition should be sufficient to provide the desired perspiration wetness and odor control from the antiperspirant stick formulation selected.

The antiperspirant stick compositions can comprise an antiperspirant active at concentrations of from about 0.5% to about 60%, and more specifically from about 5% to about 35%, by weight of the composition. These weight percentages are calculated on an anhydrous metal salt basis exclusive of water and any complexing agents such as, for example, glycine, and glycine salts. The antiperspirant active as formulated in the composition can be in the form of dispersed particulate solids having an average particle size or equivalent diameter of less than about 100 microns, more specifically less than about 20 microns, and even more specifically less than about 10 microns.

The antiperspirant active for use in the anhydrous antiperspirant compositions of the present invention can include any compound, composition or other material having antiperspirant activity. More specifically, the antiperspirant actives may include astringent metallic salts, especially inorganic and organic salts of aluminum, zirconium and zinc, as well as mixtures thereof. Even more specifically, the antiperspirant actives may include aluminum-containing and/or zirconium-containing salts or materials, such as, for example, aluminum halides, aluminum chlorohydrate, aluminum hydroxyhalides, zirconyl oxyhalides, zirconyl hydroxyhalides, and mixtures thereof.

Aluminum salts for use in the anhydrous antiperspirant stick compositions include those that conform to the formula:

$$Al_2(OH)_aCl_b \cdot xH_2O,$$

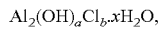

wherein a is from about 2 to about 5; the sum of a and b is about 6; x is from about 1 to about 6; and a, b, and x may have non-integer values. More specifically, aluminum chlorohydroxides referred to as "5/6 basic chlorohydroxide" can be used, wherein a=5, and "2/3 basic chlorohydroxide", wherein a=4. Processes for preparing aluminum salts are disclosed in U.S. Pat. Nos. 3,887,692; 3,904,741; U.S. Pat. No. 4,359,456; and British Patent Specification 2,048,229, the disclosures of which are incorporated herein by reference for the purpose of describing processes for preparing aluminum salts. Mixtures of aluminum salts are described in British Patent Specification 1,347,950, which description is also incorporated herein by reference.

Zirconium salts for use in the anhydrous antiperspirant stick compositions include those which conform to the formula:

$$ZrO(OH)_{2-a}Cl_a \cdot xH_2O,$$

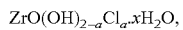

wherein a is from about 1.5 to about 1.87; x is from about 1 to about 7; and a and x may both have non-integer values. These zirconium salts are described in Belgian Patent 825,146, Schmitz, issued Aug. 4, 1975, which description is incorporated herein by reference. Zirconium salts that additionally contain aluminum and glycine, commonly known as "ZAG complexes," are believed to be especially beneficial. These ZAG complexes contain aluminum chlorohydroxide and zirconyl hydroxy chloride conforming to the above-described formulas. Such ZAG complexes are described in U.S. Pat. No. 3,792,068; Great Britain Patent Application 2,144,992; and U.S. Pat. No. 4,120,948, disclosures of which are incorporated herein by reference for the limited purpose of describing ZAG complexes.

Also suitable for use herein are enhanced efficacy aluminum.zirconium chlorohydrex-amino acid which typically has the empirical formula:

$$Al_nZr(OH)_{[3n+4-m(n+1)]}(Cl)_{[m(n+1)]} \cdot AA_q$$

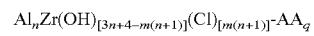

where n is 2.0 to 10.0, preferably 3.0 to 8.0; m is about 0.48 to about 1.11 (which corresponds to M:Cl approximately equal to 2.1-0.9), preferably about 0.56 to about 0.83 (which corresponds to M:Cl approximately equal to 1.8-1.2); q is about 0.8 to about 4.0, preferably about 1.0 to 2.0; and AA is an amino acid such as glycine, alanine, valine, serine, leucine, isoleucine, β-alanine, cysteine, β-amino-n-butyric acid, or γ-amino-n-butyric acid, preferably glycine. These salts also generally have some water of hydration associated with them, typically on the order of 1 to 5 moles per mole of salt (typically, about 1% to about 16%, more typically about 4% to about 13% by weight). These salts are generally referred to as aluminum-zirconium trichlorohydrex or tetrachlorohydrex when the Al:Zr ratio is between 2 and 6 and as aluminum-zirconium pentachlorohydrex or octachlorohydrex when the Al:Zr ratio is between 6 and 10. The term "aluminum-zirconium chlorohydrex" is intended to embrace all of these forms. The preferred aluminum-zirconium salt is aluminum-zirconium chlorohydrex-glycine. Additional examples of suitable high efficacy antiperspirant actives can include Aluminum Zirconium Pentachlrohydrex Glycine, Aluminum Zirconium Octachlorohydrex Glycine, or a combination thereof. These high efficacy actives are more fully described in U.S. App. Pub. No. 2007/0003499 by Shen et al. filed Jun. 30, 2005.

Additional Chassis Ingredients

Additional Structurant—The antiperspirant composition can further comprise an additional structurant. The additional structurant may be present in an amount from 1% to about 10%, by weight of the composition. The additional structurant(s) will likely be present at an amount less than the primary structurant. Non-limiting examples of suitable additional structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; and solid triglycerides; behenyl alcohol, or combinations thereof. Other non-limiting examples of additional structurants suitable for use herein are described in U.S. Pat. Nos. 5,976,514 and 5,891,424.

Solvent—The antiperspirant composition can comprise a solvent at concentrations ranging from about 20% to about 80%, and more specifically from about 30% to about 70%, by weight of the composition. The solvent can be a volatile silicone which may be cyclic or linear. "Volatile silicone" as used herein refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976), which descriptions are incorporated herein by reference. The volatile silicone can be a cyclic silicone having from 3 to 7, and more specifically from 5 to 6, silicon atoms, and still more specifically 5, like cyclopentasiloxane. These cyclic silicone materials will generally have viscosities of less than about 10 centistokes at 25° C. The volatile silicone can also be linear, suitable volatile linear silicone materials for use in the antiperspirant compositions include those represented by the formula:

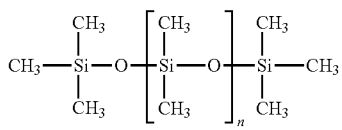

wherein n is from 1 to 7, and more specifically from 2 to 3. These linear silicone materials will generally have viscosities of less than about 5 centistokes at 25° C. Specific examples of volatile silicone solvents suitable for use in the antiperspirant compositions include, but are not limited to, Cyclomethicone 0-5; GE 7207 and GE 7158 (commercially available from General Electric Co.); Dow Corning 344; Dow Corning 345; Dow Corning 200; and DC1184 (commercially available from Dow Corning Corp.); and SWS-03314 (commercially available from SWS Silicones).

Non-Volatile Organic Fluids—Non-volatile organic fluids may be present, for example, in an amount of about 15% or less, by weight of the composition. Non-limiting examples of nonvolatile organic fluids include mineral oil, PPG-14 butyl ether, isopropyl myristate, petrolatum, butyl stearate, cetyl octanoate, butyl myristate, myristyl myristate, C12-15 alkylbenzoate (e.g., Finsolv™), octyldodecanol, isostearyl isostearate, octododecyl benzoate, isostearyl lactate, isostearyl palmitate, and isobutyl stearate.

Adjunct Ingredients—The anhydrous antiperspirant compositions can further comprise any optional material that is known for use in antiperspirant and deodorant compositions or other personal care products, or which is otherwise suitable for topical application to human skin. One example of optional materials are clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof. Talc, if used at higher levels can produce a significant amount of white residue which has been found to be a consumer negative for product acceptance. Therefore it is best to limit the composition to less than 10%, less than about 8%, less than about 6%, or less than about 3%, by weight of the composition. Nonlimiting examples of other optional materials include emulsifiers, distributing agents, antimicrobials, pharmaceutical or other topical active, preservatives, surfactants, and so forth. Examples of such optional materials are described in U.S. Pat. No. 4,049,792; U.S. Pat. Nos. 5,019,375; and 5,429,816; which descriptions are incorporated herein by reference.

D. Soft Solid

Soft solid composition can comprise volatile silicone, antiperspirant active, gellant, residue masking material, or combinations thereof. In addition, soft solids generally have a hardness value after dispensing of about 500 gram force or less.

Volatile Silicone Solvent—The soft solid can comprises a volatile silicone solvent at concentrations ranging from about 20% to about 80%, preferably from about 30% to about 70%, more preferably from about 45% to about 70%, by weight of the composition.

The volatile silicone of the solvent may be cyclic or linear. "Volatile silicone" as used herein refers to those silicone materials which have measurable vapor pressure under ambient conditions. Nonlimiting examples of suitable volatile silicones are described in Todd et al., "Volatile Silicone Fluids for Cosmetics", Cosmetics and Toiletries, 91:27-32 (1976), which descriptions are incorporated herein by reference. Preferred volatile silicone materials are those having from about 3 to about 7, preferably from about 4 to about 5, silicon atoms. Cyclic volatile silicones are preferred for use in the antiperspirant compositions herein, and include those represented by the formula:

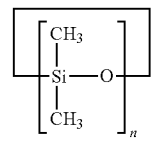

wherein n is from about 3 to about 7, preferably from about 4 to about 5, most preferably 5. These cyclic silicone materials will generally have viscosities of less than about 10 centistokes at 25° C. Linear volatile silicone materials suitable for use in the antiperspirant compositions include those represented by the formula:

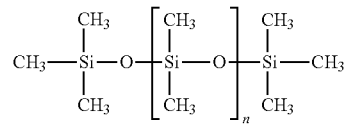

wherein n is from about 1 to about 7, preferably from about 2 to about 3. These linear silicone materials will generally have viscosities of less than about 5 centistokes at 25° C. Specific examples of volatile silicone solvents suitable for use in the antiperspirant compositions include, but are not limited to, Cyclomethicone D-5 (commercially available from G. E. Silicones), Dow Corning 344, Dow Corning 345 and Dow Corning 200 (commercially available from Dow Corning Corp.), GE 7207 and 7158 (commercially available from General Electric Co.) and SWS-03314 (commercially available from SWS Silicones Corp.).

Gellant Material—The soft solid can include a gellant material comprising fatty alcohols having from about 20 to about 60 carbon atoms, or combinations thereof, at concentrations ranging from about 0.1% to about 8% by weight of the composition. The gellant material, when combined with the volatile silicone solvent described hereinbefore, provides the composition with a physically stable structure within which the particulate antiperspirant materials are dispersed, and maintained as such over an extended period of time. Specifically, the gellant material can comprise saturated or unsaturated, substituted or unsubstituted, fatty alcohols or mixtures of fatty alcohols having from about 20 to about 60 carbons atoms, preferably from about 20 to about 40 carbon atoms. Preferred are combinations of the fatty alcohols. The fatty alcohol gellants are preferably saturated, unsubstituted monohydric alcohols or combinations thereof, which have a melting point of at less than about 110° C., more preferably from about 60° to about 110° C., even more preferably between about 100° C. and 110° C.

It has been found that this fatty alcohol-based gellant material, when combined with volatile silicone solvents provides a stable structure for maintaining a dispersion of particulate antiperspirant material in a topical formulation without the necessity of using conventional particulate thickening agents. This gellant material is especially useful in maintaining the physical stability of particulate dispersions containing higher concentrations of volatile silicone solvents.

It was also found that penetration force values for the antiperspirant compositions can be controlled by adjusting total fatty alcohol concentrations. In controlling penetration force values in this manner, there is no longer a need to use organic solvents or thickening agents to control penetration force values, which solvents or thickening agents often add cost to the formulation, introduce additional compatibility issues, and often contribute undesirable cosmetics such as prolonged stickiness, difficulty in ease of spreading, increased dry-down times and reduced dry feel after application.

Specific concentrations of the gellant materials can be selected according to the desired penetration force value. For roll-on formulations having a penetration force value of from about 20 gram·force to about 100 gram·force, gellant material concentrations preferably range from about 0.1% to about 3%, preferably from about 1.5% to about 3%, by weight of the antiperspirant composition. For other cream formulations, including those formulations suitable for use in cream applicator devices, which have a penetration force value of from about 100 gram·force to about 500 gram·force, gellant material concentrations preferably range from about 3% to about 8%, preferably from about 3% to about 6%, by weight of the antiperspirant composition.

Specific examples of fatty alcohol gellants for use in the antiperspirant compositions that are commercially available include, but are not limited to, Unilin® 425, Unilin® 350, Unilin®550 and Unilin® 700 (supplied by Petrolite)

Residue Masking Material—The soft solid compositions can further comprise a nonvolatile emollient as a residue masking material. Such materials and their use in antiperspirant products are well known in the antiperspirant art, and any such material may be incorporated into the composition of the present invention, provided that such optional material is compatible with the essential elements of the composition, or does not unduly impair product performance or cosmetics. Concentrations of the optional residue masking material can range from about 0.1% to about 40%, preferably from about 1% to about 10%, by weight of the antiperspirant composition. These optional materials can be liquid at ambient temperatures, and can be nonvolatile. The term "nonvolatile" as used in this context refers to materials which have a boiling point under atmospheric pressure of at least about 200° C. Non-limiting examples of suitable residue masking materials for use in the antiperspirant products include butyl stearate, diisopropyl adipate, petrolatum, nonvolatile silicones, octyldodecanol, phenyl trimethicone, isopropyl myristate, C12-15 ethanol benzoates and PPG-14 Butyl Ether. Residue masking materials are described, for example, in U.S. Pat. No. 4,985,238, which description is incorporated herein by reference.

Other Materials—The soft solid compositions can further comprise one, or more, other materials which modify the physical characteristics of the compositions or serve as additional "active" components when deposited on the skin. Many such materials are known in the antiperspirant art and can be used in the antiperspirant compositions herein, provided that such optional materials are compatible with the essential materials described herein, or do not otherwise unduly impair product performance. Non limiting examples of materials can include active components such as bacteriostats and fungiostats, and "non-active" components such as colorants, perfumes, cosmetic powders, emulsifiers, chelants, distributing agents, preservatives, and wash-off aids. Examples of such optional materials are described in U.S. Pat. No. 4,049,792; Canadian Patent 1,164,347; U.S. Pat. Nos. 5,019,375; and 5,429,816; which descriptions are incorporated herein by reference.

E. Aerosol

An aerosol composition can comprise a concentrate, a propellant, or a combination thereof. Alcohol is a predominant component of the concentrates provided herein. Useful alcohols include $C_1$-$C_3$ alcohols, with the preferred alcohol being ethanol. In certain examples, the alcohol is employed at a concentration level of from at least about 40%, 50% or 55% to about 80%, by weight of the concentrate.

An antiperspirant active is dissolved in the alcohol, at a level of from about 1% to about 15%, by weight of the concentrate. Various antiperspirant actives can be employed, including, for example, aluminum chloride, aluminum chlorohydrate, aluminum chlorohydrex, aluminum chlorohydrex PG, aluminum chlorohydrex PEG, aluminum dichlorohydrate, aluminum dichlorohydrex PG, aluminum dichlorohydrex PEG, aluminum sesquichlorohydrate, aluminum sesquichlorohydrex PG, aluminum sesquichlorohydrex PEG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorhydrate, aluminum zirconium trichlorohydrate, aluminum zirconium tetrachlorohydrate GLY, and aluminum zirconium trichlorohydrate GLY. In one example, aluminum chlorohydrex PG is the chosen antiperspirant active.

The antiperspirant concentrates can also include an oil or a mixture of two or more oils. Useful oils include, for example, volatile silicone oils and non-volatile organic oils. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976). The volatile silicone can be a cyclic silicone having from at least about 3 silicone atoms or from at least about 5 silicone atoms but no more than about 7 silicone atoms or no more than about 6 silicone atoms. For example, volatile silicones can be used which conform to the formula:

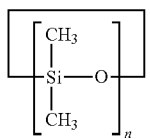

wherein n is from about 3 or from about 5 but no more than about 7 or no more than about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide): MASIL SF-V (available from Mazer) and combinations thereof. Suitable volatile silicone oils can also include linear silicone oils such as, for example, DC200 (1 cSt), DC200 (0.65 cSt), and DC2-1184, all of which are available from Dow Corning Corp. In certain examples, the volatile silicone oil can have a viscosity of less than 10 centistokes at 25° C.

Non-volatile organic, emollient oils can also be employed. A representative, non-limiting list of emollient oils includes CETIOL CC (dicaprylyl carbonate), CETIOL OE (dicaprylyl ether), CETIOL S (diethylhexylcyclohexane), and CETIOL B (dibutyl adipate), all of which are available from Cognis, and LEXFEEL 7 (neopentyl glycol diheptanoate) from Inolex. In certain examples, the organic emollient oils have a viscosity of less than 50 centistokes at 25° C. The term "organic emollient oil" as used herein means silicon-free emollient oils that are liquid at 25° C., and that are safe and light to skin and can be miscible with volatile silicone oils (as described above) and the antiperspirant active-alcohol solution in the concentration ranges described below.

The oil or mixture of oils is generally included in the concentrate formulas at a level of from about 5% to about 45%, by weight of the concentrate. This viscosity ranges noted above in connection with the different classes of oil can facilitate desired spray rates and patterns, and can help minimize nozzle clogging. To provide desired skin feel, minimal nozzle clogging, and good concentrate stability, the ratio of alcohol to volatile silicone oil is preferably greater than 1.0, 1.35, or 1.5. And in examples having both a volatile silicone oil and an organic emollient oil, the ratio of alcohol to total oil is preferably greater than or equal to about 0.90. The oils in certain examples are miscible with the alcohol and antiperspirant active solution. Although various levels of miscibility are acceptable, the oils are preferably miscible enough with the alcohol and antiperspirant active solution to yield a concentrate having a clear appearance.

The antiperspirant compositions can also include residue-masking agents and propellants as discussed above.

Additional Consumer Product Ingredients/Adjunct Materials

While not essential for the purposes of the present invention, the non-limiting list of consumer product ingredients/adjuncts illustrated hereinafter are suitable for use in the instant compositions and may be desirably incorporated in certain aspects of the invention, for example to assist or enhance cleaning performance, for treatment of the substrate to be cleaned, or to modify the aesthetics of the composition as is the case with perfumes, colorants, dyes or the like. The precise nature of these additional components, and levels of incorporation thereof, will depend on the physical form of the composition and the nature of the fabric treatment operation for which it is to be used.

Suitable adjunct materials include, but are not limited to, surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, carriers, structurants, hydrotropes, processing aids, solvents, pigments and/or fabric softener actives and clothes softening agents compatible with detergents, anti-bacterials, anti-microbials, and anti-fungals.

As stated, the adjunct ingredients are not essential to Applicants' compositions. Thus, certain aspects of Applicants' compositions do not contain one or more of the following adjuncts materials: surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems structure elasticizing agents, carriers, hydrotropes, processing aids, solvents, pigments and/or fabric softener actives, anti-bacterial/microbial. However, when one or more adjuncts are present, such one or more adjuncts may be present as detailed below.

Rheology Modifier—The liquid compositions of the present invention may comprise a rheology modifier. The rheology modifier may be selected from the group consisting of non-polymeric crystalline, hydroxy-functional materials, polymeric rheology modifiers which impart shear thinning characteristics to the aqueous liquid matrix of the composition. In one aspect, such rheology modifiers impart to the aqueous liquid composition a high shear viscosity, at 20 $sec^{-1}$ shear rate and at 21° C., of from 1 to 7000 cps and a viscosity at low shear (0.5 $sec^{-1}$ shear rate at 21° C.) of greater than 1000 cps, or even 1000 cps to 200,000 cps. In one aspect, for cleaning and treatment compositions, such rheology modifiers impart to the aqueous liquid composition a high shear viscosity, at 20 $sec^{-1}$ and at 21° C., of from 50 to 3000 cps and a viscosity at low shear (0.5 $sec^{-1}$ shear rate at 21° C.) of greater than 1000 cps, or even 1000 cps to 200,000 cps. Viscosity according to the present invention is measured using an AR 2000 rheometer from TA instruments using a plate steel spindle having a plate diameter of 40 mm and a gap size of 500 µm. The high shear viscosity at 20 sec$^{-1}$ and low shear viscosity at 0.5 sec$^{-1}$ can be obtained from a logarithmic shear rate sweep from 0.1 sec$^{-1}$ to 25 sec$^{-1}$ in 3 minutes time at 21° C. Crystalline hydroxyl functional materials are rheology modifiers which form thread-like structuring systems throughout the matrix of the composition upon in situ crystallization in the matrix. Polymeric rheology modifiers are preferably selected from polyacrylates, polymeric gums, other non-gum polysaccharides, and combinations of these polymeric materials. Generally the rheology modifier will comprise from 0.01% to 1% by weight, preferably from 0.05% to 0.75% by weight, more preferably from 0.1% to 0.5% by weight, of the compositions herein.

Structuring agents which are especially useful in the compositions of the present invention may comprise non-polymeric (except for conventional alkoxylation), crystalline hydroxy-functional materials which can form thread-like structuring systems throughout the liquid matrix when they are crystallized within the matrix in situ. Such materials can be generally characterized as crystalline, hydroxyl-containing fatty acids, fatty esters or fatty waxes. In one aspect, rheology modifiers include crystalline, hydroxyl-containing rheology modifiers include castor oil and its derivatives. In one aspect, rheology modifiers include hydrogenated castor oil derivatives such as hydrogenated castor oil and hydrogenated castor wax. Commercially available, castor oil-based, crystalline, hydroxyl-containing rheology modifiers include THIXCIN™ from Rheox, Inc. (now Elementis).

Other types of rheology modifiers, besides the non-polymeric, crystalline, hydroxyl-containing rheology modifiers described heretofore, may be utilized in the liquid detergent compositions herein. Polymeric materials which provide shear-thinning characteristics to the aqueous liquid matrix may also be employed. Suitable polymeric rheology modifiers include those of the polyacrylate, polysaccharide or polysaccharide derivative type. Polysaccharide derivatives typically used as rheology modifiers comprise polymeric gum materials. Such gums include pectine, alginate, arabinogalactan (gum Arabic), carrageenan, gellan gum, xanthan gum and guar gum. If polymeric rheology modifiers are employed herein, a preferred material of this type is gellan gum. Gellan gum is a heteropolysaccharide prepared by fermentation of Pseudomonaselodea ATCC 31461. Gellan gum is commercially marketed by C P Kelco U.S., Inc. under the KELCOGEL tradename.

A further alternative and suitable rheology modifier include a combination of a solvent and a polycarboxylate polymer. More specifically the solvent may be an alkylene glycol. In one aspect, the solvent may comprise dipropylene glycol. In one aspect, the polycarboxylate polymer may comprise a polyacrylate, polymethacrylate or mixtures thereof. In one aspect, solvent may be present, based on total composition weight, at a level of from 0.5% to 15%, or from 2% to 9% of the composition. In one aspect, polycarboxylate polymer may be present, based on total composition weight, at a level of from 0.1% to 10%, or from 2% to 5%. In one aspect, the solvent component may comprise mixture of dipropylene glycol and 1,2-propanediol. In one aspect, the ratio of dipropylene glycol to 1,2-propanediol may be 3:1 to 1:3, or even 1:1. In one aspect, the polyacrylate may comprise a copolymer of unsaturated mono- or di-carbonic acid and $C_1$-$C_{30}$ alkyl ester of the (meth)acrylic acid. In another aspect, the rheology modifier may comprise a polyacrylate of unsaturated mono- or di-carbonic acid and $C_1$-$C_{30}$ alkyl ester of the (meth)acrylic acid. Such copolymers are available from Noveon Inc under the tradename Carbopol Aqua 30®.

In the absence of rheology modifier and in order to impart the desired shear thinning characteristics to the liquid composition, the liquid composition can be internally structured through surfactant phase chemistry or gel phases.

Hueing Dye—The liquid laundry detergent composition may comprise a hueing dye.

The hueing dyes employed in the present laundry care compositions may comprise polymeric or non-polymeric dyes, organic or inorganic pigments, or mixtures thereof. Preferably the hueing dye comprises a polymeric dye, comprising a chromophore constituent and a polymeric constituent. The chromophore constituent is characterized in that it absorbs light in the wavelength range of blue, red, violet, purple, or combinations thereof upon exposure to light. In one aspect, the chromophore constituent exhibits an absorbance spectrum maximum from about 520 nanometers to about 640 nanometers in water and/or methanol, and in another aspect, from about 560 nanometers to about 610 nanometers in water and/or methanol.

Although any suitable chromophore may be used, the dye chromophore is preferably selected from benzodifuranes, methine, triphenylmethanes, napthalimides, pyrazole, napthoquinone, anthraquinone, azo, oxazine, azine, xanthene, triphenodioxazine and phthalocyanine dye chromophores. Mono and di-azo dye chromophores are may be preferred.

The hueing dye may comprise a dye polymer comprising a chromophore covalently bound to one or more of at least three consecutive repeat units. It should be understood that the repeat units themselves do not need to comprise a chromophore. The dye polymer may comprise at least 5, or at least 10, or even at least 20 consecutive repeat units. The repeat unit can be derived from an organic ester such as phenyl dicarboxylate in combination with an oxyalkyleneoxy and a polyoxyalkyleneoxy. Repeat units can be derived from alkenes, epoxides, aziridine, carbohydrate including the units that comprise modified celluloses such as hydroxyalkylcellulose; hydroxypropyl cellulose; hydroxypropyl methylcellulose; hydroxybutyl cellulose; and, hydroxybutyl methylcellulose or mixtures thereof. The repeat units may be derived from alkenes, or epoxides or mixtures thereof. The repeat units may be $C_2$-$C_4$ alkyleneoxy groups, sometimes called alkoxy groups, preferably derived from $C_2$-$C_4$ alkylene oxide. The repeat units may be $C_2$-$C_4$ alkoxy groups, preferably ethoxy groups. For the purposes of the present invention, the at least three consecutive repeat units form a polymeric constituent. The polymeric constituent may be covalently bound to the chromophore group, directly or indirectly via a linking group. Examples of suitable polymeric constituents include polyoxyalkylene chains having multiple repeating units. In one aspect, the polymeric constituents include polyoxyalkylene chains having from 2 to about 30 repeating units, from 2 to about 20 repeating units, from 2 to about 10 repeating units or even from about 3 or 4 to about 6 repeating units. Non-limiting examples of polyoxyalkylene chains include ethylene oxide, propylene oxide, glycidol oxide, butylene oxide and mixtures thereof.

Surfactants—The compositions according to the present invention may comprise a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof. The surfactant is typically present at a level of from about 0.1% to about 60%, from about 1% to about 50% or even from about 5% to about 40% by weight of the subject composition.

Chelating Agents—The compositions herein may contain a chelating agent. Suitable chelating agents include copper, iron and/or manganese chelating agents and mixtures thereof. When a chelating agent is used, the composition may comprise from about 0.1% to about 15% or even from about 3.0% to about 10% chelating agent by weight of the subject composition.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Disoersants—The compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Perfumes—The consumer product may comprise, either in neat form or via a delivery system, a perfume raw materials selected from the group consisting of perfumes such as 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, α-damascone, β-damascone, Δ-damascone, γ-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and β-dihydro ionone, linalool, ethyllinalool, tetrahydrolinalool, and dihydromyrcenol.

Additional Perfume Delivery Technologies—The compositions of the present invention may comprise one or more perfume delivery technologies that stabilize and enhance the deposition and release of perfume ingredients from treated substrate. Such perfume delivery technologies can also be used to increase the longevity of perfume release from the treated substrate. Perfume delivery technologies, methods of making certain perfume delivery technologies and the uses of such perfume delivery technologies are disclosed in US 2007/0275866 A1.

In one aspect, the compositions of the present invention may comprise from about 0.001% to about 20%, preferably from about 0.01% to about 10%, more preferably from about 0.05% to about 5%, most preferably from about 0.1% to about 0.5% by weight of the perfume delivery technology. In one aspect, said perfume delivery technologies may be selected from the group consisting of: pro-perfumes, polymer particles, functionalized silicones, polymer assisted delivery, molecule assisted delivery, fiber assisted delivery, amine assisted delivery, cyclodextrins, starch encapsulated accord, zeolite and inorganic carrier, additional perfume microcapsules, and mixtures thereof:

In one aspect, said perfume delivery technology may comprise an additional encapsulated perfume such as additional perfume microcapsules formed by at least partially surrounding a benefit agent with a wall material. Said benefit agent may include materials selected from the group consisting of perfumes such as 3-(4-t-butylphenyl)-2-methyl propanal, 3-(4-t-butylphenyl)-propanal, 3-(4-isopropylphenyl)-2-methylpropanal, 3-(3,4-methylenedioxy-phenyl)-2-methylpropanal, and 2,6-dimethyl-5-heptenal, α-damascone, β-damascone, Δ-damascone, γ-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and β-dihydro ionone, linalool, ethyllinalool, tetrahydrolinalool, and dihydromyrcenol. Suitable perfume materials can be obtained from Givaudan Corp. of Mount Olive, N.J., USA, International Flavors & Fragrances Corp. of South Brunswick, N.J., USA, or Quest Corp. of Naarden, Netherlands. In one aspect, the microcapsule wall material may comprise: melamine, polyacrylamide, silicones, silica, polystyrene, polyurea, polyurethanes, polyacrylate based materials, gelatin, styrene malic anhydride, polyamides, and mixtures thereof. In one aspect, said melamine wall material may comprise melamine crosslinked with formaldehyde, melamine-dimethoxyethanol crosslinked with formaldehyde, and mixtures thereof. In one aspect, said polystyrene wall material may comprise polyestyrene cross-linked with divinylbenzene. In one aspect, said polyurea wall material may comprise urea crosslinked with formaldehyde, urea crosslinked with gluteraldehyde, and mixtures thereof. In one aspect, said polyacrylate based materials may comprise polyacrylate formed from methyl-methacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof. In one aspect, the perfume microcapsule may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinytformaldehyde, polyvinylamine, polyethyleneimine, ethoxylated polyethyleneimine, polyvinylalcohol, polyacrylates, and combinations thereof. In one aspect, the microcapsule may be a perfume microcapsule. In one aspect, one or more types of microcapsules, for example two microcapsules types having different benefit agents may be used.

In one aspect, said perfume delivery technology may comprise an amine reaction product (ARP) or a thio reaction product. One may also use "reactive" polymeric amines and or polymeric thiols in which the amine and/or thiol functionality is pre-reacted with one or more PRMs to form a reaction product. Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Non-limiting examples of polymeric amines include polymers based on polyalkylimines, such as polyethyleneimine (PEI), or polyvinylamine (PVAm). Non-limiting examples of monomeric (non-polymeric) amines include hydroxyl amines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen and/or sulfur, for example oxygen, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in US 2005/0003980 A1 and U.S. Pat. No. 6,413,920 B1.

Suitable Fabric Softening Actives

The fluid fabric enhancer compositions disclosed herein comprise a fabric softening active ("FSA"). Suitable fabric softening actives, include, but are not limited to, materials selected from the group consisting of quaternary ammonium compounds, amines, fatty esters, sucrose esters, silicones, dispersible polyolefins, clays, polysaccharides, fatty acids, softening oils, polymer latexes and mixtures thereof.

Non-limiting examples of water insoluble fabric care benefit agents include dispersible polyethylene and polymer latexes. These agents can be in the form of emulsions, latexes, dispersions, suspensions, and the like. In one aspect, they are in the form of an emulsion or a latex. Dispersible polyethylenes and polymer latexes can have a wide range of particle size diameters ($\chi_{50}$) including but not limited to from about 1 nm to about 100 µm; alternatively from about 10 nm to about 10 µm. As such, the particle sizes of dispersible polyethylenes and polymer latexes are generally, but without limitation, smaller than silicones or other fatty oils.

Generally, any surfactant suitable for making polymer emulsions or emulsion polymerizations of polymer latexes can be used to make the water insoluble fabric care benefit agents of the present invention. Suitable surfactants consist of emulsifiers for polymer emulsions and latexes, dispersing agents for polymer dispersions and suspension agents for polymer suspensions. Suitable surfactants include anionic, cationic, and nonionic surfactants, or combinations thereof. In one aspect, such surfactants are nonionic and/or anionic surfactants. In one aspect, the ratio of surfactant to polymer in the water insoluble fabric care benefit agent is about 1:100 to about 1:2; alternatively from about 1:50 to about 1:5, respectively. Suitable water insoluble fabric care benefit agents include but are not limited to the examples described below.

Quats—Suitable quats include but are not limited to, materials selected from the group consisting of ester quats, amide quats, imidazoline quats, alkyl quats, amidoester quats and mixtures thereof. Suitable ester quats include but are not limited to, materials selected from the group consisting of monoester quats, diester quats, triester quats and mixtures thereof. In one aspect, a suitable ester quat is bis-(2-hydroxypropyl)-dimethylammonium methylsulfate fatty acid ester having a molar ratio of fatty acid moieties to amine moieties of from 1.85 to 1.99, an average chain length of the fatty acid moieties of from 16 to 18 carbon atoms and an iodine value of the fatty acid moieties, calculated for the free fatty acid, which has an Iodine Value of between 0-140, preferably 5-100, more preferably 10-80, even more preferably 15-70, even more preferably 18-55, most preferably 18-25. When a soft tallow quaternary ammonium compound softener is used, most preferably range is 25-60. In one aspect, the cis-trans-ratio of double bonds of unsaturated fatty acid moieties of the bis (2 hydroxypropyl)-dimethyl-ammonium methylsulfate fatty acid ester is from 55:45 to 75:25, respectively. Suitable amide quats include but are not limited to, materials selected from the group consisting of monoamide quats, diamide quats and mixtures thereof. Suitable alkyl quats include but are not limited to, materials selected from the group consisting of mono alkyl quats, dialkyl quats quats, trialkyl quats, tetraalkyl quats and mixtures thereof.

Amines—Suitable amines include but are not limited to, materials selected from the group consisting of amidoesteramines, amidoamines, imidazoline amines, alkyl amines, amidoester amines and mixtures thereof. Suitable ester amines include but are not limited to, materials selected from the group consisting of monoester amines, diester amines, triester amines and mixtures thereof. Suitable amido quats include but are not limited to, materials selected from the group consisting of monoamido amines, diamido amines and mixtures thereof. Suitable alkyl amines include but are not limited to, materials selected from the group consisting of mono alkylamines, dialkyl amines quats, trialkyl amines, and mixtures thereof.

Silicone—In one embodiment, the fabric softening composition comprises a silicone. Suitable levels of silicone may comprise from about 0.1% to about 70%, alternatively from about 0.3% to about 40%, alternatively from about 0.5% to about 30%, alternatively from about 1% to about 20% by weight of the composition. Useful silicones can be any silicone comprising compound. In one embodiment, the silicone polymer is selected from the group consisting of cyclic silicones, polydimethylsiloxanes, aminosilicones, cationic silicones, silicone polyethers, silicone resins, silicone urethanes, and mixtures thereof. In one embodiment, the silicone is a polydialkylsilicone, alternatively a polydimethyl silicone (polydimethyl siloxane or "PDMS"), or a derivative thereof. In another embodiment, the silicone is chosen from an aminofunctional silicone, amino-polyether silicone, alkyloxylated silicone, cationic silicone, ethoxylated silicone, propoxylated silicone, ethoxyated/propoxylated silicone, quaternary silicone, or combinations thereof.

In another embodiment, the silicone may be chosen from a random or blocky organosilicone polymer having the following formula:

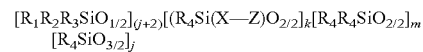
$$[R_1R_2R_3SiO_{1/2}]_{(j+2)}[(R_4Si(X-Z)O_{2/2}]_k[R_4R_4SiO_{2/2}]_m$$
$$[R_4SiO_{3/2}]_j$$

wherein:

j is an integer from 0 to about 98; in one aspect j is an integer from 0 to about 48; in one aspect, j is 0;

k is an integer from 0 to about 200, in one aspect k is an integer from 0 to about 50; when k=0, at least one of $R_1$, $R_2$ or $R_3$ is —X—Z;

m is an integer from 4 to about 5,000; in one aspect m is an integer from about 10 to about 4,000; in another aspect m is an integer from about 50 to about 2,000;

$R_1$, $R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy and X—Z;

each $R_4$ is independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_5$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy;

each X in said alkyl siloxane polymer comprises a substituted or unsubstituted divalent alkylene radical comprising 2-12 carbon atoms, in one aspect each divalent alkylene radical is independently selected from the group consisting of —$(CH_2)_s$— wherein s is an integer from about 2 to about 8, from about 2 to about 4; in one aspect, each X in said alkyl siloxane the group consisting of:

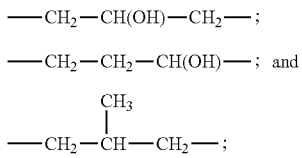

each Z is selected independently from the group consisting of

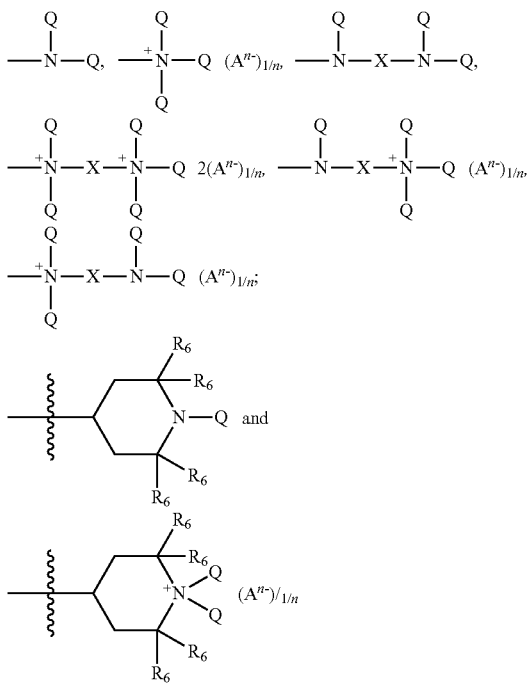

with the proviso that when Z is a quat, Q cannot be an amide, imine, or urea moiety and if Q is an amide, imine, or urea moiety, then any additional Q bonded to the same nitrogen as said amide, imine, or urea moiety must be H or a $C_1$-$C_6$ alkyl.

In one aspect, said additional Q is H. For Z, $A^{n-}$ is a suitable charge balancing anion. In one aspect $A^{n-}$ is selected from the group consisting of Cl$^-$, Br$^-$, I$^-$, methylsulfate, toluene sulfonate, carboxylate and phosphate; and at least one Q in said organosilicone is independently selected from

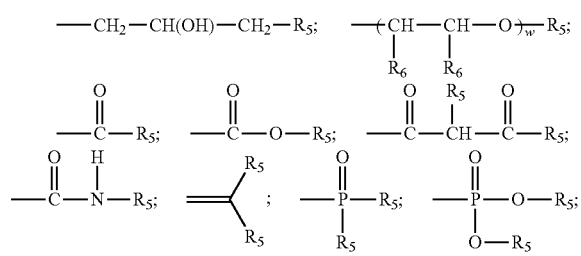

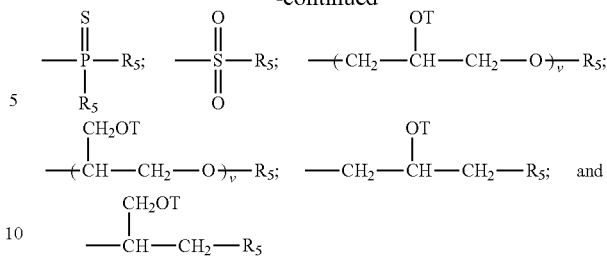

and each additional Q in said organosilicone is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, —CH$_2$—CH(OH)—CH$_2$—R$_5$;

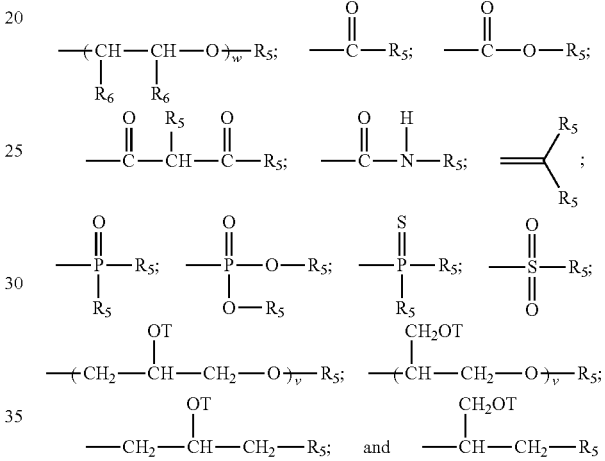

wherein each $R_5$ is independently selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, —(CHR$_6$—CHR$_6$—O—)$_w$-L and a siloxyl residue;

each $R_6$ is independently selected from H, $C_1$-$C_{18}$ alkyl each L is independently selected from —C(O)—R$_7$ or R$_7$;

w is an integer from 0 to about 500, in one aspect w is an integer from about 1 to about 200; in one aspect w is an integer from about 1 to about 50;

each $R_7$ is selected independently from the group consisting of H; $C_1$-$C_{32}$ alkyl; $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl; $C_6$-$C_{32}$ substituted alkylaryl and a siloxyl residue;

each T is independently selected from H, and

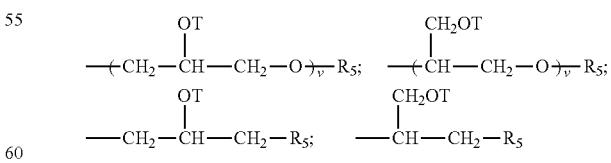

and wherein each v in said organosilicone is an integer from 1 to about 10, in one aspect, v is an integer from 1 to about 5 and the sum of all v indices in each Q in the said organosilicone is an integer from 1 to about 30 or from 1 to about 20 or even from 1 to about 10.

In another embodiment, the silicone may be chosen from a random or blocky organosilicone polymer having the following formula:

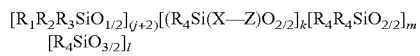

wherein
- j is an integer from 0 to about 98; in one aspect j is an integer from 0 to about 48; in one aspect, j is 0;
- k is an integer from 0 to about 200; when k=0, at least one of $R_1$, $R_2$ or $R_3$=—X—Z, in one aspect, k is an integer from 0 to about 50
- m is an integer from 4 to about 5.000; in one aspect m is an integer from about 10 to about 4,000; in another aspect m is an integer from about 50 to about 2,000;
- $R_1$, $R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_5$-$C_{32}$ substituted alkylaryl, $C_1$-$C_{32}$ alkoxy, $C_1$-$C_{32}$ substituted alkoxy and X—Z;
- each $R_4$ is independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy;
- each X comprises of a substituted or unsubstituted divalent alkylene radical comprising 2-12 carbon atoms; in one aspect each X is independently selected from the group consisting of

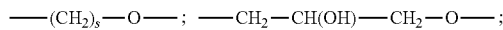

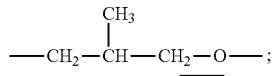

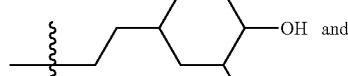

wherein each s independently is an integer from about 2 to about 8, in one aspect s is an integer from about 2 to about 4;

At least one Z in the said organosiloxane is selected from the group consisting of $R_5$;

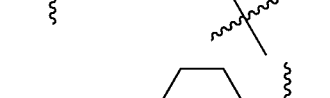

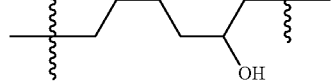

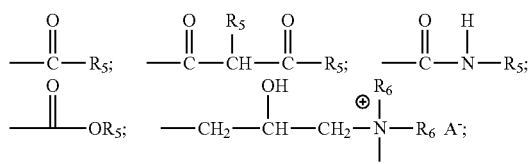

provided that when X is

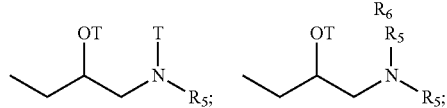

then Z = —$OR_5$ or wherein $A^-$ is a suitable charge balancing anion. In one aspect $A^-$ is selected from the group consisting of $Cl^-$, $Br^-$, $I^-$, methylsulfate, toluene sulfonate, carboxylate and phosphate and each additional Z in said organosilicone is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkyl, $C_6$-$C_{32}$ substituted alkylaryl, $R_5$,

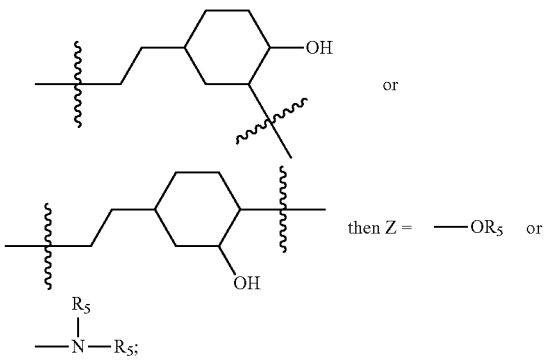

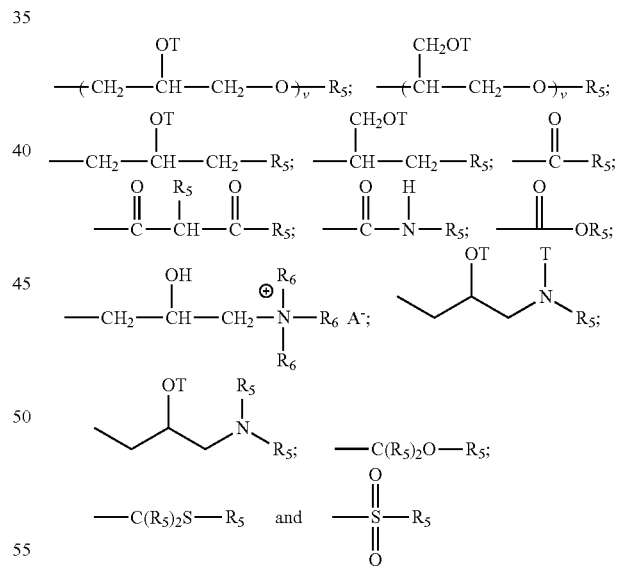

provided that when X is

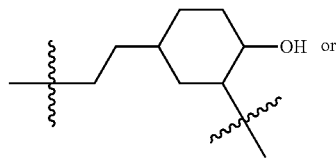

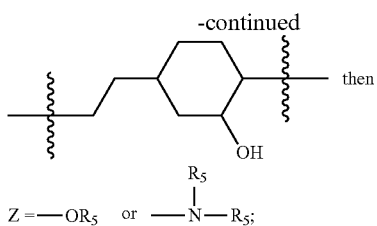

$Z = -OR_5$ or $-\overset{R_5}{\underset{|}{N}}-R_5;$ each $R_5$ is independently selected from the group consisting of H; $C_1$-$C_{32}$ alkyl; $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl or $C_6$-$C_{32}$ alkylaryl, or $C_6$-$C_{32}$ substituted alkylaryl, —(CHR$_6$—CHR$_6$—O—)$_w$—CHR$_6$—CHR$_6$-L and siloxyl residue wherein each L is independently selected from —O—C(O)—R$_7$ or —O—R$_7$;

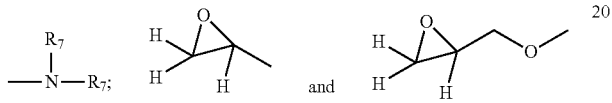

w is an integer from 0 to about 500, in one aspect w is an integer from 0 to about 200, one aspect w is an integer from 0 to about 50;

each $R_6$ is independently selected from H or $C_1$-$C_{18}$ alkyl;
each $R_7$ is independently selected from the group consisting of H; $C_1$-$C_{32}$ alkyl; $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted aryl, and a siloxyl residue;
each T is independently selected from H;

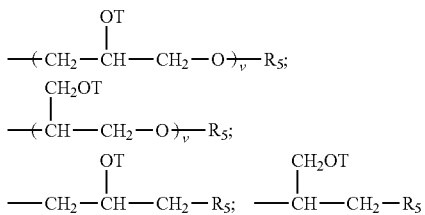

wherein each v in said organosilicone is an integer from 1 to about 10, in one aspect, v is an integer from 1 to about 5 and the sum of all v indices in each Z in the said organosilicone is an integer from 1 to about 30 or from 1 to about 20 or even from 1 to about 10.

In one embodiment, the silicone is one comprising a relatively high molecular weight. A suitable way to describe the molecular weight of a silicone includes describing its viscosity. A high molecular weight silicone is one having a viscosity of from about 10 cSt to about 3,000,000 cSt, or from about 100 cSt to about 1,000,000 cSt, or from about 1,000 cSt to about 600,000 cSt, or even from about 6,000 cSt to about 300,000 cSt.

In one embodiment, the silicone comprises a blocky cationic organopolysiloxane having the formula:

wherein:
M=[SiR$_1$R$_2$R$_3$O$_{1/2}$], [SiR$_1$R$_2$G$_1$O$_{1/2}$], [SiR$_1$G$_1$G$_2$O$_{1/2}$], [SiG$_1$G$_2$G$_3$O$_{1/2}$], or combinations thereof;
D=[SiR$_1$R$_2$O$_{2/2}$], [SiR$_1$G$_1$O$_{2/2}$], [SiG$_1$G$_2$O$_{2/2}$] or combinations thereof;
T=[SiR$_1$O$_{3/2}$], [SiG$_1$O$_{3/2}$] or combinations thereof;
Q=[SiO$_{4/2}$];
w=is an integer from 1 to (2+y+2z);
x=is an integer from 5 to 15,000;
y=is an integer from 0 to 98;
z=is an integer from 0 to 98;
$R_1$, $R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy, $C_1$-$C_{32}$ alkylamino, and $C_1$-$C_{32}$ substituted alkylamino;
at least one of M, D, or T incorporates at least one moiety $G_1$, $G_2$ or $G_3$; and $G_1$, $G_2$, and $G_3$ are each independently selected from the formula:

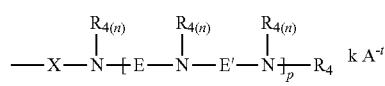

wherein:
X comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_5$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if X does not comprise a repeating alkylene oxide moiety then X can further comprise a heteroatom selected from the group consisting of P, N and O;
each $R_4$ comprises identical or different monovalent radicals selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl;
E comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide and ring-opened glycidyl, with the proviso that if E does not comprise a repeating alkylene oxide moiety then E can further comprise a heteroatom selected from the group consisting of P, N, and O;
E' comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide and ring-opened glycidyl, with the proviso that if E' does not comprise a repeating alkylene oxide moiety then E' can further comprise a heteroatom selected from the group consisting of P, N, and 0;
p is an integer independently selected from 1 to 50;
n is an integer independently selected from 1 or 2;
when at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$ or $G_3$; wherein t is an integer independently selected from 1, 2, or 3; and $k \leq (p*2/t)+1$; such that the total number of cationic charges balances the total number of anionic charges in the organopolysiloxane molecule;

and wherein at least one E does not comprise an ethylene moiety.

Particularly Preferred Adjuncts for Freshening Compositions

Buffering agent—The freshening composition of the present invention may include a buffering agent which may be a carboxylic acid, or a dicarboxylic acid like maleic acid, or a polybasic acid such as citric acid or polyacrylic acid. The acid may be sterically stable, and used in this composition for maintaining the desired pH. The buffering agent may also comprise a base such as triethanolamine, or the salt of an organic acid such as sodium citrate.

The freshening composition may have a pH from about 3 to about 8, alternatively from about 4 to about 7, alternatively from about 5 to about 8, alternatively from about 6 to about 8, alternatively about 6 to about 7, alternatively about 7, alternatively about 6.5. Carboxylic acids such as citric acid may act as metal ion chelants and can form metallic salts with low water solubility. As such, in some embodiments, the freshening composition is essentially free of citric acids. The buffer can be alkaline, acidic or neutral.

Other suitable buffering agents for freshening compositions of the present invention include biological buffering agents. Some examples are nitrogen-containing materials, sulfonic acid buffers like 3-(N-morpholino)propanesulfonic acid (MOPS) or N-(2-Acetamido)-2-aminoethanesulfonic acid (ACES), which have a near neutral 6.2 to 7.5 pKa and provide adequate buffering capacity at a neutral pH. Other examples are amino acids such as lysine or lower alcohol amines like mono-, di-, and tri-ethanolamine. Other nitrogen-containing buffering agents are tri(hydroxymethyl) amino methane (HOCH2)3CNH3 (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis(methylamine)-cyclohexane, 1,3-diamino-propanol N,N'-tetra-methyl-1,3-diamino-2-propanol, N,N-bis(2-hydroxyethyl)glycine (bicine) and N-tris(hydroxymethyl)methyl glycine (tricine). Mixtures of any of the above are also acceptable.

The freshening compositions may contain at least about 0%, alternatively at least about 0.001%, alternatively at least about 0.01%, by weight of the composition, of a buffering agent. The composition may also contain no more than about 1%, alternatively no more than about 0.75%, alternatively no more than about 0.5%, by weight of the composition, of a buffering agent.

Solubilizer—The freshening composition of the present invention may contain a solubilizing aid to solubilize any excess hydrophobic organic materials, particularly some malodor reduction materials of the current invention, perfume materials, and also optional ingredients (e.g., insect repelling agent, antioxidant, etc.) which can be added to the composition, that are not readily soluble in the composition, to form a clear translucent solution. A suitable solubilizing aid is a surfactant, such as a no-foaming or low-foaming surfactant. Suitable surfactants are nonionic surfactants, cationic surfactants, amphoteric surfactants, zwitterionic surfactants, and mixtures thereof.

In some embodiments, the freshening composition contains nonionic surfactants, cationic surfactants, and mixtures thereof. In one embodiment, the freshening composition contains ethoxylated hydrogenated castor oil. One type of suitable hydrogenated castor oil that may be used in the present composition is sold as Basophor™, available from BASF.

Freshening compositions containing anionic surfactants and/or detergent surfactants may make fabrics susceptible to soiling and/or leave unacceptable visible stains on fabrics as the solution evaporates off of the fabric. In some embodiments, the freshening composition is free of anionic surfactants and/or detergent surfactants.

When the solubilizing agent is present, it is typically present at a level of from about 0.01% to about 3%, alternatively from about 0.05% to about 1%, alternatively from about 0.01% to about 0.05%, by weight of the freshening composition.

Antimicrobial Compounds—The freshening composition of the present invention may include an effective amount of a compound for reducing microbes in the air or on inanimate surfaces. Antimicrobial compounds are effective on gram negative and gram positive bacteria and fungi typically found on indoor surfaces that have contacted human skin or pets such as couches, pillows, pet bedding, and carpets. Such microbial species include *Klebsiella pneumoniae, Staphylococcus aureus, Aspergillus niger Klebsiella pneumoniae, Streptococcus pyogenes, Salmonella choleraesuis, Escherichia coli, Trichophyton mentagrophytes*, and *Pseudomones aeruginosa*. In some embodiments, the antimicrobial compounds are also effective on viruses such H1-N1, Rhinovirus, Respiratory Syncytial, Poliovirus Type 1, Rotavirus, Influenza A, Herpes simplex types 1 & 2, Hepatitis A, and Human Coronavirus.

Antimicrobial compounds suitable in the freshening composition of the present invention can be any organic material which will not cause damage to fabric appearance (e.g., discoloration, coloration such as yellowing, bleaching). Water-soluble antimicrobial compounds include organic sulfur compounds, halogenated compounds, cyclic organic nitrogen compounds, low molecular weight aldehydes, quaternary compounds, dehydroacetic acid, phenyl and phenoxy compounds, or mixtures thereof.

In one embodiment, a quaternary compound is used. Examples of commercially available quaternary compounds suitable for use in the freshening composition are Barquat available from Lonza Corporation; and didecyl dimethyl ammonium chloride quat under the trade name Bardac® 2250 from Lonza Corporation.

The antimicrobial compound may be present in an amount from about 500 ppm to about 7000 ppm, alternatively about 1000 ppm to about 5000 ppm, alternatively about 1000 ppm to about 3000 ppm, alternatively about 1400 ppm to about 2500 ppm, by weight of the freshening composition.

Preservatives—The freshening composition of the present invention may include a preservative. The preservative is included in the present invention in an amount sufficient to prevent spoilage or prevent growth of inadvertently added microorganisms for a specific period of time, but not sufficient enough to contribute to the odor neutralizing performance of the freshening composition. In other words, the preservative is not being used as the antimicrobial compound to kill microorganisms on the surface onto which the composition is deposited in order to eliminate odors produced by microorganisms. Instead, it is being used to prevent spoilage of the freshening composition in order to increase the shelf-life of the composition.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof. Non-limiting examples of commercially available water-soluble preservatives for use in the present invention include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropene-1,3-diol, available under the trade name Bronopol®) from Inolex; 1,1'-hexamethylene bis(5-(p-chlorophenyl)biguanide), commonly known as chlorhexidine, and its salts, e.g., with acetic and digluconic acids: a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories. Inc.: N,N''-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-130 from Induchem, Germall 115® from Sutton Laboratories, Inc.; polymethoxy bicyclic oxazolidine, available under the trade name Nuosept® C from Hüls America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative are from about 0.0001% to about 0.5%, alternatively from about 0.0002% to about 0.2%, alternatively from about 0.0003% to about 0.1%, by weight of the freshening composition.

Wetting Agents—The freshening composition may include a wetting agent that provides a low surface tension that permits the composition to spread readily and more uniformly on hydrophobic surfaces like polyester and nylon. It has been found that the aqueous solution, without such a wetting agent will not spread satisfactorily. The spreading of the composition also allows it to dry faster, so that the treated material is ready to use sooner. Furthermore, a composition containing a wetting agent may penetrate hydrophobic, oily soil better for improved malodor neutralization. A composition containing a wetting agent may also provide improved "in-wear" electrostatic control. For concentrated compositions, the wetting agent facilitates the dispersion of many actives such as antimicrobial actives and perfumes in the concentrated aqueous compositions.

Non-limiting examples of wetting agents include block copolymers of ethylene oxide and propylene oxide. Suitable block polyoxyethylene-polyoxypropylene polymeric surfactants include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as C12-18 aliphatic alcohols, are not generally compatible with the cyclodextrin. Certain of the block polymer surfactant compounds designated Pluronic® and Tetronic® by the BASF-Wyandotte Corp., Wyandotte, Mich., are readily available. Nonlimiting examples of wetting agents of this type are described in U.S. Pat. No. 5,714,137 and include the Silwet® surfactants available from Momentive Performance Chemical, Albany, N.Y. Exemplary Silwet surfactants are as presented in Table 5 which may be used alone or in combinations of one another.

TABLE 5

| Name | L-7608 | L-7607 | L-77 | L-7605 | L-7604 | L-7600 | L-7657 | L-7602 |
|---|---|---|---|---|---|---|---|---|
| Average MW | 600 | 1000 | 600 | 6000 | 4000 | 4000 | 5000 | 3000 |

In another aspect of the invention freshening fabric is a restoration of the fabric such as its surface appearance (reduction of wrinkling, improved color appearance, improved or restored fabric shape). Adjunct ingredients that help restore fabric appearance are selected from: water soluble or miscible quaternary ammonium surfactants and water insoluble oil components together with surfactants, emulsifiers, and solvents needed to form a composition that is stable and does not separate. Some non-limiting preferred emulsifiers are sorbitan esters and sorbitan esters modified with alkylene oxides, such as Tween® 20 (polyoxyethylene (20)sorbitan monolaurate, branched surfactants, like Guerbet alcohols or alkylene oxide modified Guerget alcohols such as Lutensol® XL 70 (Oxirane, 2-methyl-, polymer with oxirane, mono(2-propylheptyl) ether, BASF). It is optional but preferred to have a wetting agent in this aspect of the invention. Wetting agents aid in spreading components and in reducing foaming of the composition during spraying. Some preferred wetting agents include the class of wetting agents known in the art as superwetters. Not to be bound by theory, superwetters pack very efficiently at surfaces resulting in an extremely low equilibrium surface tension. Non-limiting examples of such surfactants include Surfynols® like Surfynol® 465 and Surfynol® 104PG 50 (Dow Chemicals).

Water soluble or miscible quaternary ammonium surfactant:

Typically, minimum levels of the water soluble quat included in the compositions of the present invention are at least about 0.01%, preferably at least about 0.05%, more preferably at least about 0.1% even more preferably at least about 0.2% by weight, based on the total weight of the composition. Typically maximum levels of water soluble quaternary agent included in the composition are up to about 20%, preferably less than about 10%, and more preferably less than about 3% based on the total weight of the composition. Typically, the agent is present in the composition in an amount of about 0.2% to about 1.0%.

Specifically, the preferred water soluble quaternary compounds are dialkyl quaternary surfactant compounds. Suitable quaternary surfactants include, but are not limited to, quaternary ammonium surfactants having the formula:

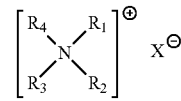

wherein $R_1$ and $R_2$ are individually selected from the group consisting of $C_1$-$C_4$ alkyl, $C_1$-$C_4$ hydroxy alkyl, benzyl, and —$(C_2H_4O)_xH$ where x has a value from about 2 to about 5; X is an anion; and (1) $R_3$ and $R_4$ are each a $C_6$-$C_{14}$ alkyl or (2) $R_3$ is a $C_6$-$C_{18}$ alkyl, and $R_4$ is selected from the group consisting of $C_1$-$C_{10}$ alkyl, $C_1$-$C_{10}$ hydroxy alkyl, benzyl, and —$(C_2H_4O)_xH$ where x has a value from 2 to 5. A preferred asymmetric quaternary compounds for this invention are compounds where R3 and R4 are not identical, and preferably one is branched and the other one is linear.

An example of a preferred asymmetric quaternary compound is ARQUAD HTL8-MS where X is a methyl sulfate ion, R1 and R2 are methyl groups, R3 is a hydrogenated tallow group with <5% mono unsaturation, and R4 is a 2-ethylhexyl group. ARQUAD HTL8-MS is available from Akzo Nobel Chemical of Arnhem, Netherlands.

An example of a suitable symmetric quaternary compound is UNIQUAT 22c50 where X is a carbonate and bicarbonate, R1 and R2 are methyl groups, R3 and R4 are C10 alkyl groups. UNIQUAT 22c50 is a registered trademark of Lonza and in North America is available thru Lonza Incorporated of Allendale, N.J.

Another example of a suitable water soluble quaternary compound is BARQUAT CME-35 which is N-Cetyl Ethyl Morpholinium Ethosulfate available from Lonza and having the following structure:

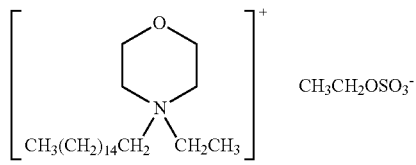

Oil Comoonent—

The oil component of the present invention represents a substantially water insoluble material that is incorporated into the composition by way of a microemulsion. The said oil component is a non-perfume raw material and a non-malodor reduction material. Typically the minimum levels of the oil component included in the composition are at least about 0.001%, preferably at least about 0.005%, more preferably at least about 0.01%, and typically maximum levels of oil components are up to about 5%, preferably less than about 3%, more preferably less than 1.5; with typical levels being in the range of about 0.05% to about 1%. The oil component can be a single component or a mixture and usually represents the incorporation of some benefit agent into the composition such as the nonlimiting example benefits softness or wrinkle reduction/release. Typically the oil component comprises substituted or unsubstituted hydrocarbon(s) and the like. For spray products it is preferred that the oil component or mix be a liquid at room temperature for ease of incorporation into the composition and less potential for nozzle clogging on drying.

The oil components of the present invention are substantially water insoluble and form a microemulsion. Substantially water insoluble means the log P of the ingredients are greater than about 1. A log P of about 1 indicates that the component would tend to partition into octanol about 10 times more than water. Some preferred, but non-limiting, components in the oil mixture are branched hydrocarbons and perfumes when perfumes are used.

Aqueous carrier—The freshening composition of the present invention may include an aqueous carrier. The aqueous carrier which is used may be distilled, deionized, or tap water. Water may be present in any amount for the composition to be an aqueous solution. In some embodiments, water may be present in an amount of about 85% to 99.5%, alternatively about 90% to about 99.5%, alternatively about 92% to about 99.5%, alternatively about 95%, by weight of said freshening composition. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the composition of the present invention due to the addition of these alcohols to such things as perfumes and as stabilizers for some preservatives, the level of monohydric alcohol may about 1% to about 5%, alternatively less than about 6%, alternatively less than about 3%, alternatively less than about 1%, by weight of the freshening composition.

Other ingredients—The freshening composition may include perfume raw materials that solely provide a hedonic benefit (i.e. that do not neutralize malodors yet provide a pleasant fragrance). Suitable perfumes are disclosed in U.S. Pat. No. 6,248,135, which is incorporated in its entirety by reference. For example, the freshening composition may include a mixture of volatile aldehydes for neutralizing a malodor and hedonic perfume aldehydes. Where perfumes, other than the volatile aldehydes in the malodor control component, are formulated into the freshening composition of the present invention, the total amount of perfumes and volatile aldehydes in the malodor control component may be from about 0.015% to about 1%, alternatively from about 0.01% to about 0.5%, alternatively from about 0.015% to about 0.3%, by weight of the freshening composition.

The freshening composition may also include diluents. Exemplary diluents include dipropylene glycol methyl ether, and 3-methoxy-3-methyl-1-butanol, and mixtures thereof.

Optionally, adjuvants can be added to the freshening composition herein for their known purposes. Such adjuvants include, but are not limited to, water soluble metallic salts, including zinc salts, copper salts, and mixtures thereof; antistatic agents; insect and moth repelling agents; colorants; antioxidants; aromatherapy agents and mixtures thereof.

The freshening composition may include other malodor reducing technologies in addition to the malodor reduction composition of the current invention. This may include, without limitation, amine functional polymers, metal ions, cyclodextrins, cyclodextrin derivatives, polyols, oxidizing agents, activated carbon, and combinations thereof.

Particularly Preferred Adjncts for Personal Care Compositions

While not essential for the purposes of the present invention, the non-limiting list of adjuncts illustrated hereinafter are suitable for use in the instant compositions and may be desirably incorporated in certain aspects of the invention, for example to assist or enhance performance.

A variety of optional ingredients can also be added to personal care compositions. Optional ingredients can include, but are not limited to, structurants, humectants, fatty acids, inorganic salts, and other antimicrobial agents or actives.

A personal care composition can also include hydrophilic structurants such as carbohydrate structurants and gums. Some suitable carbohydrate structurants include raw starch (corn, rice, potato, wheat, and the like) and pregelatinized starch. Some suitable gums include carregeenan and xanthan gum. A personal care composition can include from about 0.1% to about 30%, from about 2% to about 25%, or from about 4% to about 20%, by weight of the personal care composition, of a carbohydrate structurant.

A personal care composition can also include one or more humectants. Examples of such humectants can include polyhydric alcohols. Further, humectants such as glycerin can be included the personal care composition as a result of production or as an additional ingredient. For example, glycerin can be a by-product after saponification of the personal care composition. Including additional humectant can result in a number of benefits such as improvement in hardness of the personal care composition, decreased water activity of the personal care composition, and reduction of a weight loss rate of the personal care composition over time due to water evaporation.

A personal care composition can include inorganic salts. Inorganic salts can help to maintain a particular water content or level of the personal care composition and improve hardness of the personal care composition. The inorganic salts can also help to bind the water in the personal care composition to prevent water loss by evaporation or other means. A personal care composition can optionally include from about 0.01% to about 15%, from about 1% to about 12%, or from about 2.5% to about 10.5%, by weight of the personal care composition, of inorganic salt. Examples of suitable inorganic salts can include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and tetrasodium pyrophosphate.

A personal care composition can include one or more additional antibacterial agents that can serve to further enhance antimicrobial effectiveness of the personal care composition. A personal care composition can include, for example, from about 0.001% to about 2%, from about 0.01% to about 1.5%, or from about 0.1% to about 1%, by weight of the personal care composition, of additional antibacterial agent(s). Examples of suitable antibacterial agents can include carbanilides, triclocarban (also known as trichlorocarbanilide), triclosan, a halogenated diphenylether available as DP-300 from Ciba-Geigy, hexachlorophene, 3,4,5-tribromosalicylanilide, and salts of 2-pyridinethiol-1-oxide, salicylic acid, and other organic acids. Other suitable antibacterial agents are described in U.S. Pat. No. 6,488,943.

Scalp Active Material—In an embodiment of the present invention, the personal care composition may comprise a scalp active material, which may be an anti-dandruff active. In an embodiment, the anti-dandruff active is selected from the group consisting of: pyridinethione salts; zinc carbonate; azoles, such as ketoconazole, econazole, and elubiol; selenium sulfide; particulate sulfur; keratolytic agents such as salicylic acid; and mixtures thereof. In a further embodiment, the anti-dandruff active may be an anti-dandruff particulate. In an embodiment, the anti-dandruff particulate is a pyridinethione salt. Such anti-dandruff particulate should be physically and chemically compatible with the components of the composition, and should not otherwise unduly impair product stability, aesthetics or performance.

Pyridinethione particulates are suitable particulate anti-dandruff actives for use in composition of the present invention. In an embodiment, the anti-dandruff active is a 1-hydroxy-2-pyridinethione salt and is in particulate form. In an embodiment, the concentration of pyridinethione anti-dandruff particulate ranges from about 0.01% to about 5%, by weight of the composition, or from about 0.1% to about 3%, or from about 0.1% to about 2%. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"; zinc pyrithione), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulfide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulfide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. In an embodiment, the azole anti-microbial active is ketoconazole. In an embodiment, the sole anti-microbial active is ketoconazole.

The present invention may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the composition comprises an effective amount of a zinc-containing layered material. In an embodiment, the composition comprises from about 0.001% to about 10%, or from about 0.01% to about 7%, or from about 0.1% to about 5% of a zinc-containing layered material, by total weight of the composition. Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_x(OH)_2]^{x+}A^{m-}_{x/m} \cdot nH_2O$ wherein some or all of the divalent ions ($M^{2+}$) are zinc ions. Yet another class of ZLMs can be prepared called hydroxy double salts In an embodiment, the ZLM is a hydroxy double salt conforming to the formula $([M^{2+}_{1-x}M^{2+}_{1+x}(OH)_{3(1-y)}]^+ A^{n-}_{(1=3y)/n} \cdot nH_2O$ where the two metal ions ($M^{2+}$) may be the same or different. If they are the same and represented by zinc, the formula simplifies to $[Zn_{1+x}(OH)_2]^{2x+}2xA^- \cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In an embodiment, the composition comprises basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

Liquid Personal Care Compositions

Exemplary liquid rinse-off personal care compositions can include an aqueous carrier, which can be present at a level of from about 5% to about 95%, or from about 60% to about 85%. The aqueous carrier may comprise water, or a miscible mixture of water and organic solvent. Non-aqueous carrier materials can also be employed.

Such rinse-off personal care compositions can include one or more detersive surfactants. The detersive surfactant component can be included to provide cleaning performance to the product. The detersive surfactant component in turn comprises anionic detersive surfactant, zwitterionic or amphoteric detersive surfactant, or a combination thereof. A representative, non-limiting, list of anionic surfactants includes anionic detersive surfactants for use in the compositions can include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one example, the anionic surfactant can be sodium lauryl sulfate or sodium laureth sulfate. The concentration of the anionic surfactant component in the product can be sufficient to provide a desired cleaning and/or lather performance, and generally ranges from about 2% to about 50%.

Amphoteric detersive surfactants suitable for use in the rinse-off personal care compositions are well known in the art, and include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoactetate, disodium lauroamphoacetate disodium cocodiamphoacetate, and mixtures thereof. Amphoacetates and diamphoacetates can also be used.

Zwitterionic detersive surfactants suitable for use in the rinse-off personal care compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocoamidopropyl betaine.

The liquid rinse off personal care composition can comprise one or more phases. Such personal care compositions can include a cleansing phase and/or a benefit phase (i.e., a single- or multi-phase composition). Each of a cleansing phase or a benefit phase can include various components. The cleansing phase and the benefit phase can be blended, separate, or a combination thereof. The cleansing phase and the benefit phase can also be patterned (e.g. striped).

The cleansing phase of a personal care composition can include at least one surfactant. The cleansing phase can be an aqueous structured surfactant phase and constitute from about 5% to about 20%, by weight of the personal care composition. Such a structured surfactant phase can include sodium trideceth(n) sulfate, hereinafter STnS, wherein n can define average moles of ethoxylation. n can range, for example, from about 0 to about 3; from about 0.5 to about 2.7, from about 1.1 to about 2.5, from about 1.8 to about 2.2, or n can be about 2. When n can be less than 3, STnS can provide improved stability, improved compatibility of benefit agents within the personal care compositions, and increased mildness of the personal care compositions as disclosed in U.S. Patent Application Publication No. 2010/009285 A1.

The cleansing phase can also comprise at least one of an amphoteric surfactant and a zwitterionic surfactant. Suitable amphoteric or zwitterionic surfactants (in addition to those cited herein) can include, for example, those described in U.S. Pat. Nos. 5,104,646 and 5,106,609.

A cleansing phase can comprise a structuring system. A structuring system can comprise, optionally, a non-ionic emulsifier, optionally, from about 0.05% to about 5%, by weight of the personal care composition, of an associative polymer; and an electrolyte.

The personal care composition can optionally be free of sodium lauryl sulfate, hereinafter SLS, and can comprise at least a 70% lamellar structure. However, the cleansing phase could comprise at least one surfactant, wherein the at least one surfactant includes SLS. Suitable examples of SLS are described in U.S. Patent Application Publication No. 2010/0322878 A1.

Rinse-off personal care compositions can also include a benefit phase. The benefit phase can be hydrophobic and/or anhydrous. The benefit phase can also be substantially free of surfactant. A benefit phase can also include a benefit agent. In particular, a benefit phase can comprise from about 0.1% to about 50% benefit agent by weight of the personal care composition. The benefit phase can alternatively comprise less benefit agent, for example, from about 0.5% to about 20% benefit agent, by weight of the personal care composition. Examples of suitable benefit agents can include petrolatum, glyceryl monooleate, mineral oil, natural oils, and mixtures thereof. Additional examples of benefit agents can include water insoluble or hydrophobic benefit agents. Other suitable benefit agents are described in U.S. Patent Application Publication No. 2012/0009285 A1.

Non-limiting examples of glycerides suitable for use as hydrophobic skin benefit agents herein can include castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, and combinations thereof.

Non-limiting examples of alkyl esters suitable for use as hydrophobic skin benefit agents herein can include isopropyl esters of fatty acids and long chain esters of long chain (i.e. C10-C24) fatty acids, e.g., cetyl ricinoleate, non-limiting examples of which can include isopropyl palmitate, isopropyl myristate, cetyl riconoleate, and stearyl riconoleate. Other example can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of polyglycerin fatty acid esters suitable for use as hydrophobic skin benefit agents herein can include decaglyceryl distearate, decaglyceryl diisostearate, decaglyceryl monomyriate, decaglyceryl monolaurate, hexaglyceryl monooleate, and combinations thereof.

The rinse-off personal care composition can be applied by a variety of means, including by rubbing, wiping or dabbing with hands or fingers, or by means of an implement and/or delivery enhancement device. Non-limiting examples of implements include a sponge or sponge-tipped applicator, a mesh shower puff, a swab, a brush, a wipe (e.g., wash cloth), a loofah, and combinations thereof. Non-limiting examples of delivery enhancement devices include mechanical, electrical, ultrasonic and/or other energy devices. Employment of an implement or device can help delivery of the particulate antimicrobial agent to target regions, such as, for example, hair follicles and undulations that can exist in the underarm. The rinse-off care product can be sold together with such an implement or device. Alternatively, an implement or device can be sold separately but contain indicium to indicate usage with a rinse-off care product. Implements and delivery devices can employ replaceable portions (e.g., the skin interaction portions), which can be sold separately or sold together with the rinse-off care product in a kit.

Solid Personal Care Compositions

As noted herein, personal care compositions can take on numerous forms. One suitable form is that of a solid personal care composition. Solid compositions can take many forms like powder, pellets, bars, etc. These forms will generally be described herein as bar soap, but it should be understood that the solid composition could be in another form or shape. One example of a bar soap personal care composition can include from about 0.1% to about 35%, by weight of the personal care composition, of water, from about 45% to about 99%, by weight of the personal care composition, of soap, and from about 0.01% to about 5%, by weight of the personal care composition, of a particulate antimicrobial agent. Another suitable antimicrobial bar soap can include, for example, from about 0.1% to about 30%, by weight of the personal care composition, of water, from about 40% to about 99%, by weight of the personal care composition, of soap, and from about 0.25% to about 3%, by weight of the personal care composition, of a particulate antimicrobial agent.

Bar soap compositions can be referred to as conventional solid (i.e. non-flowing) bar soap compositions. Some bar soap composition can comprise convention soap, while others can contain synthetic surfactants, and still others can contain a mix of soap and synthetic surfactant. Bar compositions can include, for example, from about 0% to about 45% of a synthetic anionic surfactant. An example of a suitable conventional soap can include milled toilet bars that are unbuilt (i.e. include about 5% or less of a water-soluble surfactancy builder).

A personal care bar composition can include soap. By weight, the soap can be, for example, from about 45% to about 99%, or from about 50% to about 75%, by weight of the personal care composition. Such soaps can include a typical soap, i.e., an alkali metal or alkanol ammonium salt of an alkane- or alkene monocarboxylic acid. Sodium, magnesium, potassium, calcium, mono-, di- and tri-ethanol ammonium cations, or combinations thereof, can be suitable for a personal care composition. The soap included in a personal care composition can include sodium soaps or a combination of sodium soaps with from about 1% to about 25% ammonium, potassium, magnesium, calcium, or a mixture of these soaps. Additionally, the soap can be well-known alkali metal salts of alkanoic or alkenoic acids having from about 12 to about 22 carbon atoms or from about 12 to about 18 carbon atoms. Another suitable soap can be alkali metal carboxylates of alkyl or alkene hydrocarbons having from about 12 to about 22 carbon atoms. Additional suitable soap compositions are described in U.S. Patent Application Publication No. 2012/0219610 A1.

A personal care composition can also include soaps having a fatty acid. For example, one bar soap composition could contain from about 40% to about 95% of a soluble alkali metal soap of $C_8$-$C_{24}$ or $C_{10}$-$C_{20}$ fatty acids. The fatty acid can, for example, have a distribution of coconut oil that can provide a lower end of a broad molecular weight range or can have a fatty acid distribution of peanut or rapeseed oil, or their hydrogenated derivatives, which can provide an upper end of the broad molecular weight range. Other such compositions can include a fatty acid distribution of tallow and/or vegetable oil. The tallow can include fatty acid mixtures that can typically have an approximate carbon chain length distribution of 2.5% $C_{14}$, 29% $C_{16}$, 23% $C_{88}$, 2% palmitoleic, 41.5% oleic, and 3% linoleic. The tallow can also include other mixtures with a similar distribution, such as fatty acids derived from various animal tallows and/or lard. In one example, the tallow can also be hardened (i.e., hydrogenated) such that some or all unsaturated fatty acid moieties can be converted to saturated fatty acid moieties.

Suitable examples of vegetable oil include palm oil, coconut oil, palm kernel oil, palm oil stearine, soybean oil, and hydrogenated rice bran oil, or mixtures thereof, since such oils can be among more readily available fats. One example of a suitable coconut oil can include a proportion of fatty acids having at least 12 carbon atoms of about 85%. Such a proportion can be greater when mixtures of coconut oil and fats such as tallow, palm oil, or non-tropical nut oils or fats can be used where principle chain lengths can be $C_{16}$ and higher. The soap included in a personal care composition can be, for example, a sodium soap having a mixture of about 67-68% tallow, about 16-17% coconut oil, about 2% glycerin, and about 14% water.

Soap included in a personal care composition can also be unsaturated in accordance with commercially acceptable standards. For example, a soap included in a personal care composition can include from about 37% to about 45% unsaturated saponified material.

Soaps included in a personal care composition can be made, for example, by a classic kettle boiling process or modern continuous soap manufacturing processes wherein natural fats and oils such as tallow or coconut oil or their equivalents can be saponified with an alkali metal hydroxide using procedures well known to those skilled in the art. Soap can also be made by neutralizing fatty acids such as lauric ($C_{12}$), myristic ($C_{14}$), palmitic ($C_{16}$), or stearic ($C_{18}$) acids, with an alkali metal hydroxide or carbonate.

Soap included in a personal care composition could also be made by a continuous soap manufacturing process. The soap could be processed into soap noodles via a vacuum flash drying process. One example of a suitable soap noodle comprises about 67.2% tallow soap, about 16.8% coconut soap, about 2% glycerin, and about 14% water, by weight of the soap noodle. The soap noodles can then be utilized in a milling process to finalize a personal care composition.

Test Methods for the Commercial Products/Formulations

Viscosity Test Method

Viscosity is measured using an AR 550 rheometer/viscometer from TA instruments (New Castle, Del., USA), using parallel steel plates of 40 mm diameter and a gap size of 500 μm. The high shear viscosity at 20 $s^{-1}$ is obtained from a logarithmic shear rate sweep from 0.1 $s^{-1}$ to 25 $s^{-1}$ in 3 minutes time at 21° C.

Test Method for Determining the Logarithm of the Octanol/Water Partition Coefficient (log P)

The value of the log of the Octanol/Water Partition Coefficient (log P) is computed for each PRM in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Cleaning and/or Treatment Composition Examples

A series of cleaning and/or treatment compositions are prepared and evaluated as follows: the examples being designated with the letters CL followed by the sequence to distinguish from the microcapsule examples, noted above. In each example and table below, the amounts of each ingredient is presented as a wt %.

Example CL1—Light Cleaning/Additive Composition

A liquid composition for very light cleaning or additive to the laundry process is prepared with microcapsules of the present invention by combining the microcapsules with the additional ingredients presented in Table 6.

TABLE 6

| Ingredients | Amount |
|---|---|
| Nonionic Surfactant (1) | 0-10 |
| Emulsifier (2) | 0-10 |
| Cationic surfactant | 0-10 |
| Anti-bac | 0-5 |
| Free (Neat) Perfume | 0-10 |
| Microcapsules (3) | 0-10 |
| Structurant | 0-0.3 |
| Aesthetics Dye | 0.015 |
| Water | Balance |

(1) Alkyl ethoxylate with alkyl chain length between C8 and C18, preferably C12 to C16 and mixtures thereof with 3 to 12 ethoxylate groups, preferably 5 to 9.
(2) Emulsifier description, including Cremophor, Basophor, Spans and Tweens, etc.
(3) Microcapsules made in accordance with the examples of the present specification

Example CL2—Liquid Detergent Compositions

A HDL-Heavy Duty Liquid composition is prepared with microcapsules of the present invention by combining the microcapsules with the additional ingredients presented in Table 7. The exemplified space is meant to represent dilute to concentrated detergent products. The resulting detergent liquid product when used to wash articles of clothing is effective at freshening washed clothing.

TABLE 7

| Ingredient | % wt Active |
|---|---|
| Alkyl (ethoxy) sulfate (1) | 0-30 |
| Linear alkyl benzene sulfonic acid (2) | 0-30 |
| HSAS (3) | 0-30 |
| Nonionic Surfactant (4) | 0-15 |
| Amine Oxide | 0-8 |
| Citric Acid | 0-10 |
| Lactic Acid | 0-10 |
| $C_{12}$-$C_{18}$ Fatty Acid | 0-5 |
| Protease (55.3 mg/g) | 0-3 |
| Amylase (25.4 mg/g) | 0-2 |
| Borax | 0-5 |
| Calcium Formate | 0-0.5 |
| Polyethyleneimine 600, EO20 (5) | 0-5 |
| Polyethyleneimine 600, EO24, PO16 (6) | 0-5 |
| DTPA (7) | 0-5 |
| Optical Brightener (8) | 0-1 |
| NaOH | As needed |
| Na Cumene Sulfonate | 0-5 |
| Na Formate | 0-1 |
| MEA hydrogenated castor oil | 0-0.5 |
| Aesthetics Dye | 0-1.0 |
| Free (Neat) Perfume | 0-3.0 |
| Microcapsules (9) | 0-5 |
| Water and Solvent | To 100 |
| pH | 3.5-8.5 |

(1) Typically the alkyl group has about 12 to about 18 carbons and with 0 to about 3 ethoxylate groups.
(2) Typically the alkyl group has about 10 to about 16 carbons.
(3) HSAS is secondary alkyl sulfate, acid form
(4) Alkyl ethoxylate with about 12 to about 18 carbons and about 5 to about 9 moles ethoxylation.
(5) Polyethyleneimine at about 600 molecular weight reacted with about 20 moles of ethylene oxide.
(6) Polyethyleneimine at about 600 molecular weight reacted with about 24 moles of ethylene oxide and about 16 moles of propylene oxide.
(7) Select optical brighteners from one or more of the following. Brightener 14, Brightener 36, Brightener 49.
(8) Select chelant from one or a combination of the following non-limiting list DTPA di diethylene triamine pentaacetic acid, Tiron ® is 4,5-Dihydroxy-1,3-benzenedisulfonic acid disodium salt monohydrate, EDTA ethylene diamine tetra acetate, HEDP 1-Hydroxyethylidene-1,1-diphosphonic Acid, Octapirox 1-Hydroxy-4-methyl-6-(2,4,4-trimethylpentyl)-2(1H)-pyridone Ethanolamine, EDDS Ethylenediamine-N,N'-disuccinic acid.
(9) Microcapsules made in accordance with the examples of the present specification.

Example CL3—Liquid Fabric Enhancer Composition

Examples of liquid fabric enhancer compositions are prepared with microcapsules of the present invention by combining the microcapsules of the present invention with the additional ingredients as presented in Table 8.

TABLE 8

| Ingredient | A | B | C | D |
|---|---|---|---|---|
| FSA[1] | 12 | 21 | 18 | 14 |
| Low MW alcohol | 1.95 | 3.0 | 3.0 | 2.28 |
| Structurant | 1.25[2] | NIL | 0.2[3] | NIL |
| Free (Neat) Perfume | 1.50 | 1.8 | 2.0 | 1.50 |
| Microcapsules[4] | 4.0 | 1.85 | 1.85 | 3.7 |
| Calcium Chloride | 0.10 | 0.12 | 0.1 | 0.45 |
| DTPA[5] | 0.005 | 0.005 | 0.005 | 0.005 |
| Preservative (ppm)[7] | 5 | 5 | 5 | 5 |
| Antifoam[8] | 0.015 | 0.15 | 0.11 | 0.011 |
| Polyethylene imines[9] | 0.15 | 0.05 | NIL | 0.1 |
| PDMS emulsion[10] | NIL | 0.5 | 1 | 2.0 |
| Dispersant[11] | NIL | NIL | 0.5 | 0.2 |
| Organosiloxane[12] | 5 | NIL | NIL | NIL |
| Front-end Stability Aid | 0.06[13] | 0.63[14] | 0.36[13] | 0.14[14] |
| Dye (parts per million ppm) | 40 | 11 | 30 | 40 |
| Ammonium Chloride | 0-0.1 | 0-0.1 | 0-0.1 | 0.10 |
| Hydrochloric Acid | 0.010 | 0.01 | 0.10 | 0.010 |
| Water | Balance | Balance | Balance | Balance |

[1]N,N-di(tallowoyloxyethyl)-N,N-dimethylammonium chloride.
[2]Cationic high amylose maize starch-available from National Starch under the trade name HYLON VII ®.
[3]Cationic polymer available from BASF ® under the name Rheovis ® CDE.
[4]Microcapsules made in accordance with the examples of the present specification
[5]Diethylene triamine pentaacetic acid
6. 19% active aqueous solution of 1,2 Benzisothiazolin-3-one (BIT) in dipropylene glycol and water available from Dow Chemical under the trade name Koralone B-119
[7]Silicone antifoam agent available from Dow Corning ® under the trade name DC2310.
[8]Polyethylene imines available from BASF under the trade name Lupasol ®.
[9]Polydimethylsiloxane emulsion from Dow Corning ® under the trade name DC346.
[10]Non-ionic such as TWEEN 20 ™ or cationic surfactant as Berol 648 and Ethoquad ® C 25 from Akzo Nobel.
[11]Organosiloxane polymer condensate made by reacting hexamethylenediisocyanate (HDI), and a, w silicone diol and 1,3-propanediamine, N'-(3-(dimethylamino)propyl)-N, N-dimethyl- Jeffcat Z130) or N-(3-dimethylaminopropyl)-N,Ndiisopropanolamine (Jeffcat ZR50) commercially available from Wacker Silicones, Munich, Germany.
[12]Fineoxocol ® 180 from Nissan Chemical Co.
[13]Isofol ® 16 from Sasol.
**For example PGE Liquid fabric enhancer compositions in EXAMPLE CL3 are made by combining the molten fabric softener active with the front-end stability agent to form a first mixture. This first mixture is combined with water and hydrochloric acid using a high shear mixing device to form a second mixture. The adjunct ingredients are combined with the second mixture using low shear mixing to form the fabric enhancing formula.

Liquid fabric enhancer compositions in EXAMPLE CL3 are used by dosing 10 to 60 g of the formula into the rinse liquor for example via dispensing into a clothes washing machine. Clothes are dried on a line or in an automated clothes dryer. The fabrics treated with these formulas have improved feel and scent.

Example CL4—Liquid Fabric Enhancer Composition

Examples of liquid fabric enhancer compositions are prepared with microcapsules of the present invention by combining the microcapsules with the additional ingredients as presented in Table 9.

TABLE 9

| Ingredients | A | B | C | D | E | F | G | H | I |
|---|---|---|---|---|---|---|---|---|---|
| DEEDMAC[1] | 16 | 9 | 9 | 12 | 4 | NIL | NIL | NIL | NIL |
| Dialkyl esterdimethyl ammonium methyl sulfate[2] | NIL | NIL | NIL | NIL | NIL | 7 | 2.5 | 9 | 11 |
| HCl | 0.02 | 0.01 | 0.01 | 0.01 | NIL | 0.01 | NIL | 0.01 | 0.01 |
| Fromic Acid | 0.05 | 0.05 | 0.05 | 0.05 | 0.05 | 0.05 | 0.025 | 0.05 | 0.05 |
| Proxel ®[3] | 0.02 | 0.02 | 0.02 | 0.02 | 0.02 | 0.02 | 0.02 | 0.02 | 0.02 |
| CaCl2 | 1 | 0.3 | 0.3 | 0.4 | NIL | 0.3 | NIL | 0.1 | 0.1 |
| Antifoam MP10[4] | 0.2 | 0.1 | 0.1 | 0.1 | 0.1 | 0.1 | 0.1 | 0.1 | 0.1 |
| Rheovis CDE ®[5] | 0.1 | NIL | NIL | NIL | 0.4 | 0.1 | 0.2 | NIL | 0.2 |
| Flosoft ®[6] | NIL | 0.1 | 0.1 | 0.05 | NIL | NIL | NIL | 0.3 | NIL |
| Bardac 2250 ®[7] | NIL | NIL | 0.5 | NIL | NIL | NIL | NIL | NIL | 0.5 |
| NaHEDP[8] | 0.03 | 0.03 | 0.03 | 0.03 | 0.03 | 0.03 | 0.03 | 0.03 | 0.03 |
| Genapol T680 ®[9] | NIL | NIL | NIL | NIL | NIL | NIL | NIL | 0.6 | 0.8 |
| CAE10[10] | NIL | 0.6 | NIL | NIL | NIL | NIL | NIL | NIL | NIL |
| Glycerol | NIL | 10 | NIL | NIL | NIL | NIL | NIL | NIL | 5 |
| Perfume | 0-2 | 0-1 | 0-1.5 | 0-3 | 0-2.3 | 0-1.5 | 0-3 | 0-0.8 | 0-0.5 |
| Encapsulated perfume | 0-0.25 | 0-0.5 | 0-1 | 0-0.6 | 0-1.5 | 0-3 | 0-0.5 | 0-1 | 0-5 |
| Water | To 100 | To 100 | To 100 | To 100 | To 100 | To 100 | To 100 | To 100 | To 100 |

[1]91% activity, 9% isopropanol, supplied by Evonik
[2]Reaction product of triethanolamine and alkyl and/or fatty acids followed by methylation.
[3]Proxel GXL, 20% activity, supplied by Lonza
[4]MP10, 8% activity, supplied by Dow Corning
[5]Rheovis CDE, suppiled by BASF
[6]Flosoft 222, supplied by SNF
[7]Bardac 2250, 50% activity, supplied by Lonza
[8]20% activity
[9]Genapol T680, supplied by Clariant
[10]C12-14 ALCOHOL ETHOXYLATE AE 10 (24E10)

Example CL5—Soluble Uni-Dose Heavy Duty Liquid Composition

Examples of Soluble Uni-dose heavy duty liquid composition are prepared with microcapsules of the present invention by combining the microcapsules with the additional ingredients as presented in Table 10. The resulting Unidose pouch product when used to wash articles of clothing is effective at freshening garments.

TABLE 10

| | A | B | C | D | E | F 3 compartments pouched product | | |
|---|---|---|---|---|---|---|---|---|
| Form | liquid | liquid | liquid | liquid | gel | liq | liq | liq |
| Compartment # | 1 | 1 | 1 | 1 | 1 | 1 | 2 | 3 |
| Dosage (g) | 36.0 | 38.0 | 32.0 | 36.0 | 40.0 | 34.0 | 25 | 35 |
| Alkylbenzene sulfonic acid | 14.5 | 13.8 | 16.0 | 14.5 | 13.5 | 14.5 | 20.0 | NIL |
| $C_{12-14}$ alkyl ethoxy 3 sulfate | 8.5 | 16.4 | 10.0 | 8.5 | 15.0 | 8.5 | NIL | NIL |
| $C_{12-13}$ alkyl 3-ethoxylate | NIL | NIL | NIL | 13.0 | NIL | NIL | NIL | NIL |
| $C_{12-14}$ alkyl 7-ethoxylate | 12.5 | 9.0 | 14.0 | NIL | 4.0 | 12.5 | 17.0 | NIL |
| C12-18 Fatty acrd | 14.5 | 8.5 | 16.0 | 15.0 | 7.2 | 14.5 | 13.0 | NIL |
| Citric acid | NIL | NIL | NIL | 2.0 | 4.1 | NIL | NIL | NIL |
| Enzymes | 0-3 | 0-3 | 0-3 | NIL | 0-3 | 0-3 | 0-3 | NIL |
| PAP granule[1] | NIL | NIL | NIL | NIL | NIL | NIL | NIL | 50.0 |
| Ethoxysulfated Hexamethylene Diamine Dimethyl Quat | NIL | 3.0 | NIL | NIL | NIL | NIL | 2.2 | NIL |
| Ethoxylated Polyethylenimine | 4.0 | 1.0 | NIL | 4.0 | 3.0 | 2.0 | NIL | NIL |
| Hydroxyethane diphosphonic acid | 1.0 | 1.0 | NIL | NIL | 1.6 | 0.6 | 0.6 | NIL |
| Ethylene diamine tetra(methylene phosphonic) acid | NIL | NIL | NIL | 1.0 | NIL | NIL | NIL | NIL |
| Brightener | 0.2 | 0.2 | 0.3 | 0.3 | 0.2 | 0.2 | 0.2 | NIL |
| Polydimethyl Siloxane | NIL | NIL | 3.0 | NIL | NIL | NIL | NIL | NIL |
| Hueing dye[2] | NIL | NIL | NIL | NIL | NIL | NIL | 0.05 | NIL |
| Perfume | 0-3.0 | 0-3.0 | 0-3.0 | 0-3.0 | 0-3.0 | 0-3.0 | NIL | NIL |
| Microcapsules of the present invention | 0-5 | 0-5 | 0-5 | 0-5 | 0-5 | 0-5 | NIL | NIL |
| Water and minors | | | | | To 100% | | | |

TABLE 10-continued

|  | A | B | C | D | E | F<br>3 compartments<br>pouched product |
|---|---|---|---|---|---|---|
| Buffers (sodium carbonate, monoethanolamine) |  |  |  | To pH 8.0 |  |  |
| Solvents (1,2 propanediol, ethanol), Sulfate |  |  |  | To 100% |  |  |

[1] ε-Phthalimido-peroxy-hexanoic acid particles made by Solvay Chemicals international, Brussels Belgium.

Example CL6—Dish Cleaning Composition

Examples of Dish cleaning compositions are prepared with microcapsules of the present invention by combining the microcapsules with the additional ingredients presented in Table 11.

TABLE 11

| EXAMPLES | A | B | C | D | E | F | G |
|---|---|---|---|---|---|---|---|
| Alkyl $C_{10-14}$ Ethoxy Sulphate (AE0.6S) | 26.9 | NIL | NIL | 25.7 | NIL | 11.1 | 21.0 |
| Alkyl $C_{10-14}$ Ethoxy Sulphate (AE2S) | NIL | 18.7 | 26.9 | NIL | 18.7 | NIL | NIL |
| Sodium alkyl benzene sulfonate | NIL | 8.0 | NIL | NIL | NIL | NIL | NIL |
| Sodium paraffin sulfonate | NIL | NIL | NIL | NIL | 8.0 | NIL | NIL |
| C12-14 dimethyl amine oxide | 6.1 | NIL | NIL | 4.1 | NIL | 3.7 | 10.0 |
| Cocamido propyl betaine | NIL | 4.5 | 6.8 | 3.2 | 6.0 | NIL | NIL |
| C12-13 EO7 nonionic | NIL | NIL | NIL | NIL | NIL | 1.0 | 2.0 |
| Branched Nonionic; 3-propyl heptanol EO8 | 1.0 | 0.8 | NIL | NIL | NIL | NIL | 1.0 |
| PEI600-EO10-PO7 block polymer | NIL | NIL | 0.8 | NIL | NIL | 0.4 | 0.8 |
| Perfume | 0-2 | 0-2 | 0-2 | 0-2 | 0-2 | 0-2 | 0-2 |
| Perfume microcapsule of the present invention | 0.1 | 0-0.5 | 0-0.5 | 0-1.5 | 0-0.5 | 0-0.8 | 0-2 |
| Ethanol | 4.0 | 5.0 | 3.0 | 3.0 | 2.0 | NIL | 3.0 |
| Polypropylene glycol MW2000 | 1.1 | 0.8 | 1.1 | 1.1 | 1.1 | 0.5 | 1.1 |
| Sodium Chloride | 1.3 | 0.8 | 1.3 | 0.5 | 0.8 | 1.3 | 1.3 |
| Minors* and water | | | to balance up to 100% | | | | |

Example CL7—Compositions for Use in Cleaning in an Automatic Dishwashing Machine Automatic dish washing compositions are prepared with microcapsules of the present invention by combining the microcapsules with the additional ingredients presented in Table 12. Some aspects of the present invention have at least one water soluble compartment, preferably composed of Monosol 660 mm M8630K Water Soluble Film. In other aspects of the present invention the unit dose composition has more than one compartment and at least one of the compartments comprises powder as in EXAMPLE CL7 A.

TABLE 12

|  | % wt Active | | |
|---|---|---|---|
| Ingredients | A<br>POWDER | B<br>LIQUID | C<br>LIQUID |
| Sodium sulfate | 0-15 | 2-7 | NIL |
| Soda ash | 20-50 | NIL | NIL |
| Zinc carbonate | NIL | 0.1-0.2 | NIL |
| Zinc sulfate | NIL | NIL | 0.3-0-7 |
| Sodium silicate | 0-2 | 3-15 | 1-2 |
| Sodium bicarbonate | NIL | NIL | 15-25 |
| Glutamic acid-N,N-diacetic acid, tetra sodium salt. | NIL | NIL | 3-7 |
| Citric acid | NIL | NIL | 1-2 |
| NaOH (preferably low iron) | NIL | 0-1.5 |  |
| Carboxylate polymer, GT101 | 2.5-7 | NIL | 1.25 |
| Plurafac SLF 180 | 0.2-1.5 | NIL | 0.25-0.6 |
| MDGA | 5-15 | NIL | NIL |
| Polyacrylate thickener Polygel DKP | NIL | 0.7-2.3 | NIL |
| Acrylic/sulfonic dispersant Acusol 588 | 2-10 | NIL | NIL |
| Acrylic acid polymer Acusol 425 N | NIL | 1-3 | NIL |
| Sodium hypochlorite bleach | 0-30 | 0.3-1.5 | NIL |
| Ultimase | 0-2 | NIL | NIL |
| Stainzyme | 0-1 | NIL | NIL |
| Savinase Ultra 16XL | NIL | NIL | 0.2-0.5 |
| Termamyl Ultra 300 L | NIL | NIL | 0.1-0.15 |
| Calcium Chloride | NIL | NIL | 0.3-0.4 |
| Dipropylene Glycol | NIL | NIL | NIL |
| Nonionic Surfactant | NIL | 9-50 | NIL |
| Plurafac SLF 180 | NIL | 25-60 | NIL |
| Glycerine | NIL | 0-1 | NIL |
| Dye | NIL | 0-0.1 | NIL |
| Nitric acid | NIL | 0.005-0.05 | NIL |
| Preservative sodium benzoate | NIL | 0.25-0.8 | 0.2-0.8 |
| Perfume | 0-1 | 0-1 | 0-1 |

TABLE 12-continued

| Ingredients | % wt Active | | |
|---|---|---|---|
| | A POWDER | B LIQUID | C LIQUID |
| Microcapsules of the present invention | 0-2 | 0-2 | 0-2 |
| Balance Water | To 100 | To 100 | To 100 |

Fatty acid has C12 to C14 alkyl groups and mixtures thereof
Rheovis ® AT 120 is a methacrylate/acrylic acid copolymer.

Example CL8—Spray for Cleaning Hard Surfaces

A spray for cleaning hard surfaces is prepared with microcapsules of the present invention by combining the microcapsules with the additional ingredients presented in Table 13.

TABLE 13

| Ingredients | % wt Active |
|---|---|
| $C_{13-15}$ alkyl ethoxylate (30) | 0-0.5 |
| $C_{9-11}$ alkyl ethoxylate (8) | 0-0.5 |
| $C_{12/14}$ Amine-oxide | 0-3 |
| Barquat 4280-Z | 0-3 |
| Ethylene glycol monohexyl ether | 0-1 |
| Phenoxyethanol | 0-1 |
| Dense Soda ash | 0-0.3 |
| Pentasodium diethylene triamine (DTPA) | 0-0.4 |
| Tartaric acid | 0-0.1 |
| Dye | 0-1.2 |
| 1,2-Benzisothioazolin-3-one | 0-0.1 |
| Perfume | 0-1 |
| Microcapsules of the present invention | 0-0.5 |
| Balance Water | To 100 |

Solid Consumer Products Examples

Example CL9—Free Flowing Particles

Free flowing particles are prepared with microcapsules of the present invention by combining the microcapsules with the additional ingredients presented in Table 14.

TABLE 14

| Ingredients | % wt Active | | | |
|---|---|---|---|---|
| | A | B | C | D |
| Polyethylene glycol | 70-99 | 0-20 | 0-29 | 0-40 |
| Clay | 0-29 | 0-20 | 0-20 | 0-10 |
| NaCl | 0-29 | 50-99 | 0-29 | 0-40 |
| Na2SO4 | 0-10 | 0-10 | 0-10 | 0-5 |
| Urea | 0-29 | 0-29 | 0-99 | 0-40 |
| Polysaccharide | 0-29 | 0-29 | 0-29 | 0-5 |
| Zeolite | 0-29 | 0-29 | 0-29 | 0-5 |
| Plasticizers/Solvents | | | | |
| Starch/Zeolite | 0-29 | 0-29 | 0-29 | 0-5 |
| Silica | 0-5 | 0-5 | 0-5 | 0-5 |
| Metal oxide | 0-29 | 0-29 | 0-29 | 0-29 |
| Metal catalyst | 0.001-0.5 | 0.001-0.5 | 0.001-0.5 | 0.001-0.5 |
| Opacifier | 0-5 | 0-5 | 0-1 | 0-1 |
| Water | 0-2 | 0-2 | 0-5 | 0-5 |
| Perfume | 0-5 | 0-5 | 0-5 | 0-5 |
| Microcapsules made in accordance with the examples of the present specification | 0-10 | 0-4.5 | 0-3 | 0-7.5 |

Example CL10—Spray-Dried Laundry Detergent Powder Composition

Spray-Dried Laundry Detergent Powder compositions are prepared with microcapsules of the present invention by combining the microcapsules with the additional ingredients as presented in Table 15

TABLE 15

| Ingredients | wt % Active | | | |
|---|---|---|---|---|
| Slurry | A | B | C | D |
| Linear alkyl benzene sulfonate | 10.6 | 15.8 | 21.3 | 35.7 |
| Acrylate/maleate copolymer | 4.6 | 6.8 | 9.4 | 14.2 |
| Ethylenediame disuccinic acid and/or Hydroxyethane dimethylene phosphonic acid | 1.4 | 2.1 | 1.7 | 2.9 |
| Sodium carbonate | 19.4 | 28.5 | 18.8 | 29.9 |
| Sodium sulfate | 28.6 | 42.4 | — | — |
| Carboxy methyl cellulose polymer | — | — | 4.3 | 7.1 |
| Carboxy methyl cellulose polymer | — | — | 4.3 | 7.1 |
| Miscellaneous, such as magnesium sulfate, brightener and one or more stabilizers | 1.4 | 2.2 | 2.5 | 4.2 |
| Perfume | 0-3 | 0-2 | 0-2 | 0-3 |
| Microcapsules made in accordance with the examples of the present specification | 0-5 | 0-5 | 0-5 | 0-5 |
| Water | Balance | Balance | Balance | Balance |

A first spray-dried laundry detergent powder is formed from an aqueous slurry, slurry A from Table 15, which is prepared having a moisture content of 34.0%. Any ingredient added above in liquid form is heated to 70° C., such that the aqueous slurry is never at a temperature below 70° C. At the end of preparation, the aqueous slurry is heated to 80° C. and pumped under pressure ($5 \times 10^6$ $Nm^{-2}$) into a counter current spray-drying tower with an air inlet temperature of from 290° C. The aqueous slurry is atomized and the atomized slurry is dried to produce a solid mixture, which is then cooled and sieved to remove oversize material (>1.8 mm) to form a spray-dried powder, which is free-flowing. Fine material (<0.15 mm) is elutriated with the exhaust the exhaust air in the spray-drying tower and collected in a post tower containment system. The spray-dried powder has a moisture content of 2.0 wt %, a bulk density of 310 g/l and a particle size distribution such that greater than 90 wt % of the spray-dried powder has a particle size of from 150 to 710 micrometers. The composition of the spray-dried powder A is listed in the Table 15. Perfume and microcapsules are sprayed onto the composition following the spray dry procedure.

A second spray-dried laundry detergent powder is formed from an aqueous slurry, slurry B from Table 15, having a moisture content of 42.0%. Any ingredient added above in liquid form is heated to 70° C., such that the aqueous slurry is never at a temperature below 70° C. At the end of preparation, the aqueous slurry is heated to 85° C. and pumped under pressure (from $6.5 \times 10^6$ $Nm^{-2}$), into a counter current spray-drying tower with an air inlet temperature of from 275° C. The aqueous slurry is atomized and the atomized slurry is dried to produce a solid mixture, which is then cooled and sieved to remove oversize material (>1.8 mm) to form a spray-dried powder B, which is free-flowing. Fine material (<0.15 mm) is elutriated with the exhaust the exhaust air in the spray-drying tower and collected in a post tower containment system. The spray-dried powder has a moisture content of 3.0 wt %, a bulk density of 250 g/l and a particle size distribution such that greater than 90 wt % of the spray-dried powder has a particle size of from 150 to 710 micrometers. The composition of the spray-dried powder is given in Table 15. Perfume and microcapsules are sprayed onto the composition after the spray dry process.

Example CL11—Freshening Composition

Liquid fabric spray fabric freshening compositions are prepared with microcapsules of the present invention by combining the microcapsules with the additional ingredients as presented in Table 16 The resulting fabric refreshing spray product when used to treat fabric

TABLE 16

| Ingredient | A | B | C | D | E |
|---|---|---|---|---|---|
| Deionized Water | Balance | Balance | Balance | Balance | Balance |
| Ethanol | 3.0 | 3.0 | 3.0 | 3.0 | 3.0 |
| Lupasol HF[1] | NIL | NIL | NIL | NIL | NIL |
| Hydroxypropyl b-CD | NIL | NIL | NIL | NIL | NIL |
| Diethylene Glycol | NIL | NIL | NIL | NIL | NIL |
| Silwet L-7600 | 0.1 | 0.1 | 0.1 | 0.100 | 0.100 |
| Basophor EL60[2] | NIL | 0.05 | 0.05 | 0.05 | 0.05 |
| Maleic Acid and/or Citric Acid[3] | As needed | As needed | As needed | As needed | As needed |
| Koralone B-119 | 0.015 | 0.015 | 0.015 | 0.015 | 0.015 |
| Hydroxypropyl β-cyclodextrin | NIL | NIL | NIL | NIL | NIL |
| Sodium Hydroxide[3] | As needed | As needed | As needed | As needed | As needed |
| Microcapsules made in accordance with the examples of the present specification | 1 | 2 | 0.1 | 5 | 0.05 |
| Fragrance | 0 | 0 | 0 | 0 | 0 |
| Target pH | 6.8 | 6.8 | 6.8 | 6.8 | 6.8 |
| Total | 100 | 100 | 100 | 100 | 100 |

Example CL12—Dryer Added Fabric Softener Sheet Composition

A series of dryer added fabric softener sheet compositions are prepared with microcapsules of the present invention by combining the microcapsules with the additional ingredients as presented in Table 17. The compositions A-D of this example are mixed homogeneously and impregnated onto a non-woven polyester sheet having dimensions of about 6% in×12" (about 17.1 cm×30.5 cm) and weighing about 1 gram. The resulting dryer added fabric softener sheet product when added to an automatic dryer is effective at softening, freshening and reducing the static on clothing that contact the sheet.

TABLE 17

| Ingredient | A<br>Wt %<br>Active | B<br>Wt %<br>Active | C<br>Wt %<br>Active | D<br>Wt %<br>Active |
|---|---|---|---|---|
| DEQA[1] | 0-50 | 50 | — | — |
| DEQA[2] | 0-50 | — | — | 30 |
| DTDMAMS[3] | 0-50 | — | 50 | — |
| 7018FA[4] | 0-50 | — | 50 | — |
| TS-20[5] | 0-15 | — | — | 15 |
| SMS[6] | 0-15 | — | — | 15 |
| SDASA[7] | 0-19 | 25 | — | 19 |
| TPED[8] | — | 3 | — | — |
| Complex[9] | 0-16.5 | 16.5 | — | 8.0 |
| Clay[10] | Balance | Balance | Balance | Balance |
| Free (Neat) Perfume | 0-4 | 0-1.5 | 0-3 | 0-1.5 |
| Microcapsules[11] | 0-4 | 0-4 | 0-2 | 0-2 |
| Active Weight (g/sheet) | 2.4 | 2.4 | 1.9 | 2.4 |

[1]DEQA[1]: Di(soft tallowoyloxyethyl)dimethylammonium methyl sulfate with 25% > 7018 FA, as described below, as solvent
[2]DEQA[2]: Di(soft tallowoyloxyethyl)hydroxyethylmethylammoniun methyl sulfate with 18% partially hydrogenated tallow fatty acid solvent
[3]DTDMAMS: Di(hydrogenated tallowalkyl)dimethylammonium methyl sulfate
[4]7018FA: 70:30 Stearic Acid:Palmitic Acid (IV = 0) Industrene 7018 sold by Witco
[5]TS-20: Polyoxyethylene-20 Sorbitan Tristearate (Glycosperse TS-20, sold by Lonza
[6]SMS: Sorbitan Mono Stearate
[7]SDASA: 1:2 ratio of stearyl dimethyl amine:triple pressed stearic acid
[8]TPED: N,N,N',N'-Tetrakis(2-hydroxypropyl)ethylenediamine (Quadrol, sold by BASF)
[9]Complex: Beta-Cyclodextrin/Perfume Complex
[10]Clay: Calcium Bentonite Clay (Bentonite L sold by Southern Clay Products Free (Neat) Perfume
[11]Microcapsules made in accordance with the examples of the present specification Examples CL13-CL15—Absorbent Articles Example CL13—Pads for Menstrual Odor Control The microcapsules of the present invention are added into the core of an Always Ultra Thin Unscented menstrual pad. Optionally, a neat fragrance is preferably added beneath the core of the article.

Example CL14—Heavy Al Pants for Urine Odor Control

The microcapsules of the present invention are added into the core of an Always Discreet Adult Incontinence Underwear, moderate absorbency. Optionally, a neat fragrance is preferably added beneath the core of the article.

Example CL15—Diapers for Odor Control

The microcapsules of the present invention are added into the core of an Pampers Cruisers Baby Diaper. Optionally, a neat fragrance is preferably added beneath the core of the article.

Examples CL16-CL17—Personal Care Compositions

Example CL16—Body Wash

Body Wash compositions are prepared with microcapsules of the present invention by combining the microcapsules with the additional ingredients as presented in Table 18.

TABLE 18

| Body Wash | A | B | C |
|---|---|---|---|
| Sodium Laureth-3 Sulfate (as 28% active) | 27.85% | 27.85% | 27.85% |
| Water | Q.S. | Q.S. | Q.S. |
| Sodium Lauryl Sulfate (as 29% active) | 10.34 | 10.34 | 10.34 |
| Cocamidopropyl Betaine B (30% active) | 4.01 | 4.01 | 4.01 |
| Citric Acid | 0.18 | 0.18 | 0.18 |
| Sodium Benzoate | 0.3 | 0.3 | 0.3 |
| Disodium EDTA | 0.12 | 0.12 | 0.12 |
| Methylchloroisothiazolinone/Methylisothiazolinone | 0.04 | 0.04 | 0.04 |
| Sodium Chloride | 2.35 | 1.7 | 1.6 |
| Neat Perfume | 1.25 | 1 | 2 |
| Microcapsules made in accordance with the examples of the present specification | 0.25 | 0.175 | 0.25 |

QS - indicates that this material is used to bring the total to 100%

Example CL17—Shampoos

Shampoo compositions are prepared with microcapsules of the present invention by combining the microcapsules with the additional ingredients as presented in Table 19.

TABLE 19

| Ingredient | A | B | C | D | E | F |
|---|---|---|---|---|---|---|
| | | Wt % | | | | |
| Ammonium Laureth Sulfate[1] | 14.1 | 14.1 | 14.1 | 14.1 | 14.1 | 14.1 |
| Ammonium Lauryl Sulfate[2] | 3.1 | 3.1 | 3.1 | 3.1 | 3.1 | 3.1 |
| Ammonium Xylenesulfonate[3] | 0.45 | 0.45 | 0.45 | 0.45 | 0.45 | 0.45 |
| TWEEN 60[4] | 3.0 | 3.0 | 3.0 | 3.0 | 3.0 | 3.0 |
| Polyquaternium-10[5] | 0.35 | 0.35 | 0.35 | 0.35 | 0.35 | 0.35 |
| Cetrimonium Chloride[6] | 0.5 | 0.5 | 0.5 | 0.5 | 0.5 | 0.5 |
| Selenium Sulfide[7] | 1.0 | 1.0 | 1.0 | 1.0 | 0.2 | 0.2 |
| Dimethicone[8] | 0.60 | 0.60 | 0.60 | 0.60 | 0.60 | 0.60 |
| Ethylene Glycol Distearate[9] | 3.0 | 3.0 | 3.0 | 3.0 | 3.0 | 3.0 |
| Cocamide MEA[10] | 3.0 | 3.0 | 3.0 | 3.0 | 3.0 | 3.0 |
| Zinc Pyrithione[11] | — | 0.2 | 0.2 | — | 1.0 | 1.0 |
| Zinc Carbonate[12] | — | — | 1.61 | — | — | 1.61 |
| Neat Fragrance | 1.1 | 0.75 | 0.75 | 0.65 | 0.85 | 1.0 |
| Microcapsules made in accordance with the examples of the present specification | 0.25 | 0.25 | 0.175 | 0.175 | 0.175 | 0.175 |
| Cetyl Alcohol[13] | 0.42 | 0.42 | 0.42 | 0.42 | 0.42 | 0.42 |
| DMDM Hydantoin | 0.40 | 0.40 | 0.40 | 0.40 | 0.40 | 0.40 |
| Sodium Chloride | 0.30 | 0.30 | 0.30 | 0.30 | 0.30 | 0.30 |
| Stearyl Alcohol[14] | 0.20 | 0.20 | 0.20 | 0.20 | 0.20 | 0.20 |
| Hydroxypropyl Methylcellulose[15] | 0.02 | 0.02 | 0.02 | 0.02 | 0.02 | 0.02 |
| Water | Q.S. | Q.S. | Q.S. | Q.S. | Q.S. | Q.S. |

[1]Ammonium Laureth Sulfate at 25% active, supplier: P&G

[2]Ammonium Lauryl Sulfate at 25% active, supplier: P&G

[3]Ammonium Xylene Sulfonate 40% active, supplier: Stepan

[4]Polysorbate 60, upplier: Croda

[5]UCARE Polymer LR400, supplier - Dow Chemical

[6]cetrimonium chloride, supplier - Croda

[7]Selenium disulfide, supplier Eskay

[8]Viscasil 330M from Momentive Performance Materials with a viscosity of 330,000 cSt (centistokes).

[9]Ethylene Glycol Disterate, supplier: Stepan

[10]Ninol COMF from the Stepan Company

[11]Zinc Pyrithione, supplier Lonza

[12]Zinc Carbonate Basic, supplier Pan Continental Chemical

[13]Cetyl Alcohol, supplier P&G

[14]Stearyl Alcohol, supplier P&G

[15]Methocel, supplier Dow Chemical

Examples CL18-CL20—Antiperspirant and/or Deodorant Compositions

Example CL18—Deodorants

Deodorants are prepared with microcapsules of the present invention by combining the microcapsules with the additional ingredients as presented in Table 20.

TABLE 20

| Ingredient | A | B | C | D | E |
|---|---|---|---|---|---|
| Product Form | Solid Deodorant | Solid Deodorant | Solid Deodorant | Solid Deodorant | Aerosol Deodorant or Body Spray |
| dipropylene glycol | 48 | 48 | 20 | 30 | 20 |
| propylene glycol | 19.3 | 19.3 | 22 | — | — |
| tripopylene glycol | — | — | 25 | — | — |
| Glycerine | — | — | — | 10 | — |
| PEG -8 | — | — | — | 20 | — |
| Propylene Glycol 3 Myristyl Ether | 1.4 | 1.4 | — | — | — |
| ethanol | — | — | — | — | QS |
| Water | QS | QS | QS | QS | — |
| sodium stearate | 5.4 | 5.4 | 5.5 | 5.5 | — |
| tetra sodium EDTA | 0.5 | 0.5 | 0.05 | 0.05 | — |
| sodium hydroxide | — | — | 0.04 | 0.04 | — |
| triclosan | — | — | 0.3 | 0.3 | — |
| Neat Perfume | 2.8 | 2.8 | 2 | 1.5 | 1.5 |
| Microcapsules made in accordance with the examples of the present specification | 3 | 0.7 | 1.0 | 0.5 | 0.35 |
| Blue 1 | 0.0009 | 0.0009 | — | — | — |
| Propellant (1,1 difluoroethane) | — | — | — | — | 40 |

QS - Indicates that this material is used to bring the total to 100%.

Example CL19—Antiperspirants

Antiperspirant compositions are prepared with microcapsules of the present invention by combining the microcapsules with the additional ingredients as presented in Table 21.

TABLE 21

| | Form | | | | | |
|---|---|---|---|---|---|---|
| | Invisible Solid | Invisible Solid | Invisible Solid | Soft Solid | Soft Solid | Soft Solid |
| Ingredient | A | B | C | D | E | F |
| Aluminum Zirconium Trichlorohydrex Glycine Powder | 24 | 24 | 24 | 26.5 | 26.5 | 26.5 |
| Cyclopentasiloxane | Q.S. | Q.S. | Q.S. | Q.S. | Q.S. | Q.S. |
| Demethicone | — | — | — | 5 | 5 | 5 |
| CO-1897 Stearyl Alcohol NF | 14 | 14 | 14 | — | — | — |
| Hydrogenated Castor Oil MP80 Deodorized | 3.85 | 3.85 | 3.85 | — | — | — |
| Behenyl Alcohol | 0.2 | 0.2 | 0.2 | — | — | — |
| Tribehenin | — | — | — | 4.5 | 4.5 | 4.5 |
| C 18-36 acid triglyceride | — | — | — | 1.125 | 1.125 | 1.125 |
| C12-15 Alkyl Benzoate | 9.5 | 9.5 | 5 | — | — | — |
| PPG-14 Butyl Ether | 6.5 | 6.5 | — | 0.5 | 0.5 | 0.5 |
| Phenyl Trimethicone | 3 | — | 3 | — | — | — |
| White Petrolatum | 3 | — | — | 3 | 3 | 3 |
| Mineral Oil | 1.0 | 1.0 | 1.0 | — | — | — |
| Free (Neat) Perfume | 1.0 | 0.75 | 2.0 | 0.75 | 1.0 | 1.25 |
| Microcapsules made in accordance with the examples of the present specification | 0.25 | 3 | 0.35 | 0.175 | 0.25 | 0.1 |
| Beta-Cyclodextrin complexed with Malodor reducing composition | — | 3.0 | — | — | — | 3.0 |
| Talc Imperial 250 USP | 3.0 | 3.0 | 3.0 | — | — | — |

QS - indicates that this material is used to bring the total to 100%.

Example CL20—Clear Gel Antiperspirant

Clear gel antiperspirants are prepared with microcapsules of the present invention by combining the microcapsules with the additional ingredients as presented in Table 22.

TABLE 22

|  | 3.1 Clear Gel Antiperspirant | 3.2 Clear Gel Antiperspirant | 3.3 Clear Gel Antiperspirant | 3.4 Clear Gel Antiperspirant | 3.5 Clear Gel Antiperspirant |
|---|---|---|---|---|---|
| Aluminum Zirconium Octachlorohydrex Gly | 20 | 18.5 | 20 | 18 | 10 |
| Water | Q.S | Q.S. | Q.S. | Q.S. | Q.S. |
| Ethanol | 5.5 | 8 | 6 | 6.5 | 5 |
| Propylene Glycol | 5.3 | 5 | 7 | 5.5 | 8 |
| DC 5225c - Cyclopentasiloxane & PEG/PPG-18/18 Dimethicone | 7.8 | 9 | 6.5 | 7 | 8 |
| Dimethicone | 5.6 | 4.5 | 5.8 | 5 | 4.1 |
| Cyclopentasiloxane | 2.6 | 3 | 1 | 3 | 2.5 |
| Free (Neat) Perfume | 1.0 | 0.75 | 2.0 | 0.75 | 1.0 |
| Microcapsules made in accordance with the examples of the present specification | 0.25 | — | 0.35 | 0.175 | 0.25 |

QS - indicates that this material is used to bring the total to 100%.

For avoidance of doubt and to preclude any unintentional omission of an embodiment, it is to be appreciated that the present teaching also pertains to and by this reference incorporates any and all consumer products and methods of making consumer products containing or made using, respectively, the microcapsules embraced by the appended claims as well as the microcapsules resulting from the methods of the appended claims in combination with at least one consumer product ingredient. In general, these compositions and methods will contain or employ, as appropriate, a sufficient amount of said microcapsules to provide, based on the total consumer product weight, said consumer product with from 0.001% about to about 25%, preferably from about 0.01% to about 10%, more preferably from about 0.05% to about 5%, most preferably from about 0.1% to about 0.5% of said microcapsules.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

Although the process and prepared microcapsules of the present specification as well as various commercial and consumer products containing/comprising the same have been described with respect to specific embodiments and examples, it should be appreciated that the present teachings are not limited thereto and other embodiments utilizing the concepts expressed herein are intended and contemplated without departing from the scope of the present teaching as intended in the true spirit and scope of the invention. It is therefore intended any and all modifications, variations, or equivalents that fall within the spirit and scope of the underlying principles are within the scope of this invention and are covered by the appended claims.

The invention claimed is:

1. A method of making microcapsules comprising a high strength capsule wall having an inner surface and an outer surface and an encapsulated hydrophobic core material, said method comprising:
   (a) forming a dispersion of (i) an oil phase composition comprising a hydrophobic core material, one or more polymerizable ethylenically unsaturated core monomer(s) that are at least partially soluble in the hydrophobic core material, and at least one initiator for effecting or initiating polymerization of the core monomer(s), in (ii) a water or water-based continuous phase, further referred to as the water phase composition, comprising water, at least one ethylenically unsaturated polymerizable water phase monomer(s) that is poor to moderately hydrophilic, and at least one initiator for effecting or initiating polymerization of the water phase monomer;
   (b) initiating polymerization of the water phase monomer(s) and the core monomer(s);
   (c) continuing polymerization of the monomers to form the capsule wall; and
   (d) optionally, thereafter isolating the formed microcapsules from the continuous phase; and
   wherein the poor to moderately hydrophilic water phase monomer(s) are characterized as having a solubility of less than about 50 g/L in deionized water at 20° C.; and the core monomer(s) are sufficiently soluble in the hydrophobic core material such that the oil phase composition contains 5 to 25 wt % of the core monomer(s), based on the total weight of the oil phase composition.

2. The method of claim 1 wherein prior to or concurrent with step (a), either the oil phase composition, the water phase composition, or both is subjected to such conditions as will induce oligomerization/prepolymerization of at least some of the core monomers, the water phase monomers or both.

3. The method of claim 2, wherein each phase composition to be subjected to the oligomerization/prepolymerization step contains at least two initiators, at least one of which (a) is activated by conditions that are different from the conditions that are necessary to activate the other(s) in the same phase and (b) initiates said oligomerization/prepolymerization.

4. The method of claim 2 wherein the core monomers are subjected to said oligomerization/prepolymerization.

5. The method of claim 2 wherein both the core monomers and the water phase monomers are subjected to said oligomerization/prepolymerization.

6. The method of claim 1 wherein step (b) comprises a two or more step polymerization process wherein in a first step (i) the dispersion is subjected to conditions that initiate or effectuate the oligomerization or prepolymerization of at least some of the core monomer(s), the water phase monomer(s), or both the core monomer(s) and the water phase monomer(s), and in a second or subsequent step (ii) the dispersion is subjected to one or more conditions that initiates or effectuates the full polymerization of the polymerizable monomers including the oligomers/prepolymers and any remaining monomer of the oligomerization/prepolymerization step (i).

7. The method of claim 6 wherein each phase composition to be subjected to the oligomerization/prepolymerization step contains at least two initiators, at least one of which (a) is activated by conditions that are different from the conditions that are necessary to activate the other(s) in the same phase and (b) initiates said oligomerization/prepolymerization.

8. The method of claim 6 wherein the dispersion is subjected to conditions that induce or promote the movement of the so formed oligomers/prepolymers to the interface of the oil phase composition and the water phase composition concurrent with or subsequent to the oligomerization/prepolymerization step.

9. The method of claim 6 wherein the core monomers are subjected to conditions that effectuate the oligomerization or prepolymerization thereof.

10. The method of claim 6 wherein both the core monomers and the water phase monomers are subjected to conditions that effectuate the oligomerization or prepolymerization thereof.

11. The method of claim 10 wherein the conditions which effect oligomerization and/or prepolymerization of the monomers of each phase composition is the same and said oligomerization or prepolymerization occurs concurrently in each phase.

12. The method of claim 10 wherein the conditions which effect oligomerization and/or prepolymerization are different and occur in sequence.

13. The method of claim 6 wherein following completion of the oligomerization/prepolymenzation step (i), the dispersion is subjected to such conditions as will initiate or effectuate the full polymerization of the monomers, including the already formed oligomers and prepolymers, and building of the microcapsule wall or shell at the interface of the oil phase composition and the water phase composition.

14. The method of claim 13 wherein full polymerization is concurrently initiated in both the oil phase and the water phase.

15. The method of claim 13 wherein the timing of the polymerization of the monomers and/or oligomers/prepolymers of one phase relative to the other is delayed.

16. The method of claim 15 wherein the duration of the delay is such that the capsule wall is only partially formed prior to initiation of polymerization of the monomers and/or oligomers/prepolymers of the other phase.

17. The method of claim 15 wherein the duration of the delay is such that a seed capsule is formed of the monomer and/or oligomer/prepolymer whose polymerization is to be initiated first, which seed capsule is characterized as a partially formed capsule wherein areas of the oil phase/water phase interface remain, before the polymerization of the wall forming materials of the other phase.

18. The method of claim 15 wherein the duration of the delay is such that a full capsule wall is formed of the monomer and/or oligomer/prepolymer whose polymerization is to be initiated first, said full capsule wall being characterized as one whereby the oil phase composition is isolated from the water phase composition, before the polymerization of the wall forming materials of the other phase.

19. The method of claim 1 wherein during step (b) the dispersion is subjected to conditions that induce or promote the movement of the polymerizing monomers to the interface of the oil phase composition and the water phase composition.

20. The method of claim 1 wherein the microcapsules are formed in a sequential manner with at least one of the core monomer and water phase monomer undergoing a two-step polymerization whereby oligomerization/prepolymerization of the at least one monomer material is initiated and maintained for a period of time in its respective phase after which polymerization of all wall forming materials is effected to form the microcapsule.

21. The method of claim 20 wherein the monomers of both phases are subject to a two-step polymerization whereby initiation of the oligomerization/prepolymerization of the monomers of each phase occurs concurrently.

22. The method of claim 20 wherein initiation of polymerization of the oligomers/prepolymers and the other monomer or any residual monomer, as appropriate, of each phase occurs concurrently.

23. The method of claim 20 wherein the timing of the initiation of polymerization of the oligomers/prepolymers and the other monomer or any residual monomer of each phase is delayed.

24. The method of claim 23 wherein the duration of the delay is such that the capsule wall is only partially formed prior to initiation of polymerization of the monomers and/or oligomers/prepolymers of the other phase.

25. The method of claim 23 wherein the duration of the delay is such that a seed capsule is formed of the monomer and/or oligomer/prepolymer whose polymerization is to be initiated first, which seed capsule is characterized as a partially formed capsule wherein areas of oil phase/water phase interface remain, prior to initiation of polymerization of the monomers and/or oligomers/prepolymers of the other phase.

26. The method of claim 23 wherein the duration of the delay is such that a full capsule wall is formed of the monomer and/or oligomer/prepolymer whose polymerization is to be initiated first, said full capsule wall being characterized one whereby the oil phase composition is isolated from the water phase composition, prior to initiation of polymerization of the monomers and/or oligomers/prepolymers of the other phase.

27. The method of claim 20 wherein both phases are subjected to the initial oligomerization/prepolymerization step and each phase composition contains at least two initiators, at least one of which (a) is activated by conditions that are different from the conditions that are necessary to activate the other initiator(s) of that phase and (b) initiates said oligomerization/prepolymerization.

28. The method of claim 20, wherein four initiators are employed, two in each phase, each initiator in each phase being activated by different conditions and/or having a different rate of activation under the same conditions than the other initiator in that phase; and wherein the first of each pair of initiators is activated to commence formation of the oligomers/prepolymers of each wall forming monomer(s), and after a period of time allowing the formation of said oligomers/prepolymers the second initiator in each phase is activated to cause the full polymerization of said oligomers/prepolymers and rapid wall formation.

29. The method of claim 28 wherein the first of each pair of initiators in each phase is activated by the same or similar conditions and each of second of each pair of initiators in each phase is activated by the same or similar conditions.

30. The method of claim 1 wherein the core material is selected from UV absorbers, UV reflectors, pigments, dyes, colorants, scale inhibitors, corrosion inhibitors, antioxidants, pour point depressants, waxes, deposition inhibitors, dispersants, flame retardants, biocides, active dye tracer materials, odor control agents, natural oils, flavor and perfumes oils, crop protection agents, and phase change materials.

31. The method of claim 1 wherein the core material is a phase change material.

32. The method of claim 1, wherein the water phase composition comprises 1-100 wt % of at least one poor to moderately hydrophilic ethylenically unsaturated polymerizable water phase monomer; 0-99 wt % of at least one polyfunctional ethylenically unsaturated monomer; and 0-60 wt % of other mono-functional monomers; and wherein the oil phase composition comprises at least one mono-, di-and/or poly-functional ethylenically unsaturated core monomer(s), provided at least 50 mole % of the core monomer(s) is a difunctional monomer having a water solubility of not more than about 1 g/L in deionized water at 20° C.

33. The method of claim 32 wherein at least 50 mole % of the water phase monomers are difunctional monomers having poor to moderately hydrophilic properties.

34. The method of claim 32 wherein the core monomer(s) and the water phase monomers are all free radically polymerizable.

35. The method of claim 32 wherein oligomers/-prepolymers of the core monomer(s) are less hydrophobic, less lipophilic, or both less hydrophobic and less lipophilic than the core monomer(s) themselves and the oligomers/prepolymers of the water phase monomers are less hydrophilic and/or more lipophilic than the water phase monomers themselves.

36. The method of claim 32, wherein the water phase monomer(s) is present in the water phase composition in an amount of from about 0.5 to 20 wt % based on the total weight of the water phase composition.

37. The method of claim 36 wherein the weight ratio of the water phase monomer to the core monomer(s) is from about 1:3 to about 1:50.

38. The method of claim 1 wherein the water phase monomers and the core monomer(s) are characterized as having at least one or more acrylate, methacrylate, amino, urethane, alcohol or ether groups.

39. The method of claim 38 wherein the water phase monomers have a hydrophobic or non-hydrophilic hydrocarbon or hetero-hydrocarbon portion whereby as the water phase monomer oligomerizes/prepolymerizes, the so formed oligomer/prepolymer manifests at least one of the following properties as compared to the water phase monomers themselves: becomes less soluble in the water phase composition, tends to manifest less hydrophilicity, tends to increase in hydrophobicity, or tends to increase in lipophilicity and wherein the core monomer(s) are such that as they oligomerize/prepolymerize, the so formed oligomer/prepolymer manifests at least one of the following properties as compared to the core monomer(s) themselves: becomes less soluble in the core material, become less hydrophobic, become more hydrophilic, become less lipophilic, tend to show less affinity for the core material, or tend to show greater affinity for the water phase composition.

40. The method of claim 38 wherein the same monomer may be in both the core phase composition and the water phase composition provided that (a) at least one of the core phase composition and the water phase composition includes a second monomer which is not present in the other phase or (b) at least one phase is subjected to a multi-step process wherein the monomer or monomer mixture of that one phase is oligomerized/prepolymerized before being fully polymerized.

41. The method of claim 1 wherein the core monomer(s) or the water phase monomers or both are selected such that as the monomers of each phase oligomerize/prepolymerize, the oligomers/prepolymers of the respective monomers lose affinity for the phase in which they are present or increase affinity for the other phase.

42. The method of claim 1 wherein the poor to moderately hydrophilic water phase monomers have a solubility of from about 0.01 g/L to about 50 g/L as measured in deionized water at 20° C. and the hydrophobic core monomers have a solubility not more than about 25 g/L as measured in deionized water at 20° C.

* * * * *